(12) United States Patent
Yao et al.

(10) Patent No.: US 7,604,959 B2
(45) Date of Patent: Oct. 20, 2009

(54) CELL-BASED ASSAYS EMPLOYING VOLTAGE AND CALCIUM DYES

(75) Inventors: Yong Yao, North Potomac, MD (US); Liang Cao, Bethesda, MD (US); Jianming Lu, Potomac, MD (US); Isabel Llorente, Adamstown, MD (US)

(73) Assignee: Atto BioScience Inc., Rockville, MD (US)

( * ) Notice: Subject to any disclaimer, the term of this patent is extended or adjusted under 35 U.S.C. 154(b) by 147 days.

(21) Appl. No.: 11/783,884

(22) Filed: Apr. 12, 2007

(65) Prior Publication Data

US 2008/0166803 A1 Jul. 10, 2008

Related U.S. Application Data

(63) Continuation-in-part of application No. 10/087,217, filed on Mar. 4, 2002, now Pat. No. 7,115,377.

(60) Provisional application No. 60/515,442, filed on Oct. 30, 2003, provisional application No. 60/589,012, filed on Jul. 20, 2004, provisional application No. 60/330,663, filed on Oct. 26, 2001.

(51) Int. Cl.
  *C12N 15/12* (2006.01)
  *C07K 14/705* (2006.01)
(52) U.S. Cl. .................. 435/69.1; 435/7.1; 435/7.2; 435/252.3; 435/320.1; 536/23.5
(58) Field of Classification Search .................. None
See application file for complete search history.

(56) References Cited

U.S. PATENT DOCUMENTS 7,166,463 B2 * 1/2007 Karpen et al. ............... 435/325

7,341,836 B2 * 3/2008 Karpen et al. .................. 435/6
2003/0157571 A1 8/2003 Karpen et al.

FOREIGN PATENT DOCUMENTS

WO 03038039 A2 5/2003

OTHER PUBLICATIONS

Zong et al. Three amino acids in the C-linker are major determinants of gating in cyclic nucleotide-gated channels. 1998,The EMBO Journal 17(2):353-362.*
Liu et al. Clacium-calmodulin modulation of the olfactory cyclic nucleotide-gated cation channel, Nov. 25, 1994, Science 266:1348-1354.*
Rich et al. In vivo assessment of local phosphodiesterase activity using taylored cyclic nucleotode-gated channels as cAMP sensors, Jul. 2001, Journal of General Physiology 118:63-77.*
Rich et al. Cyclic nucleotide-gated channels colocalize with adenylate cyclase in regions of restricted cAMP diffusion. Jul. 17, 2000, Journal of General Physiology 116:147-161.*
Gavazzo et al., "A point mutation in the pore region alters gatings CA2+ blockage, and permeation of olfactory cyclic nucleotide-gated channels"; Journal of General Physiology, 116(3) pp. 311-325 (Sep. 2000).

* cited by examiner

*Primary Examiner*—John D Ulm
(74) *Attorney, Agent, or Firm*—David C. Scherer; Bozicevic, Field & Francis LLP

(57) ABSTRACT

Disclosed are novel compositions and methods employing cyclic nucleotide-gated channels and fluorescence dyes and other indicators in detecting changes of intracellular cAMP levels, for instance in response to the stimulation of G-protein-coupled receptors. CNG mutants comprising one or more pore mutations that enhance sensitivity to cAMP and decrease divalent cation-mediated blockage are used in a variety of assays, including detection of the G-protein-coupled receptor activity. Also disclosed are novel dye quencher formulations that are particularly suited for cell-based assays of protein interactions.

18 Claims, 38 Drawing Sheets

HEK293H parental cells, RFU: -3000 to 24000
1 μM Isoproterenol          Buffer

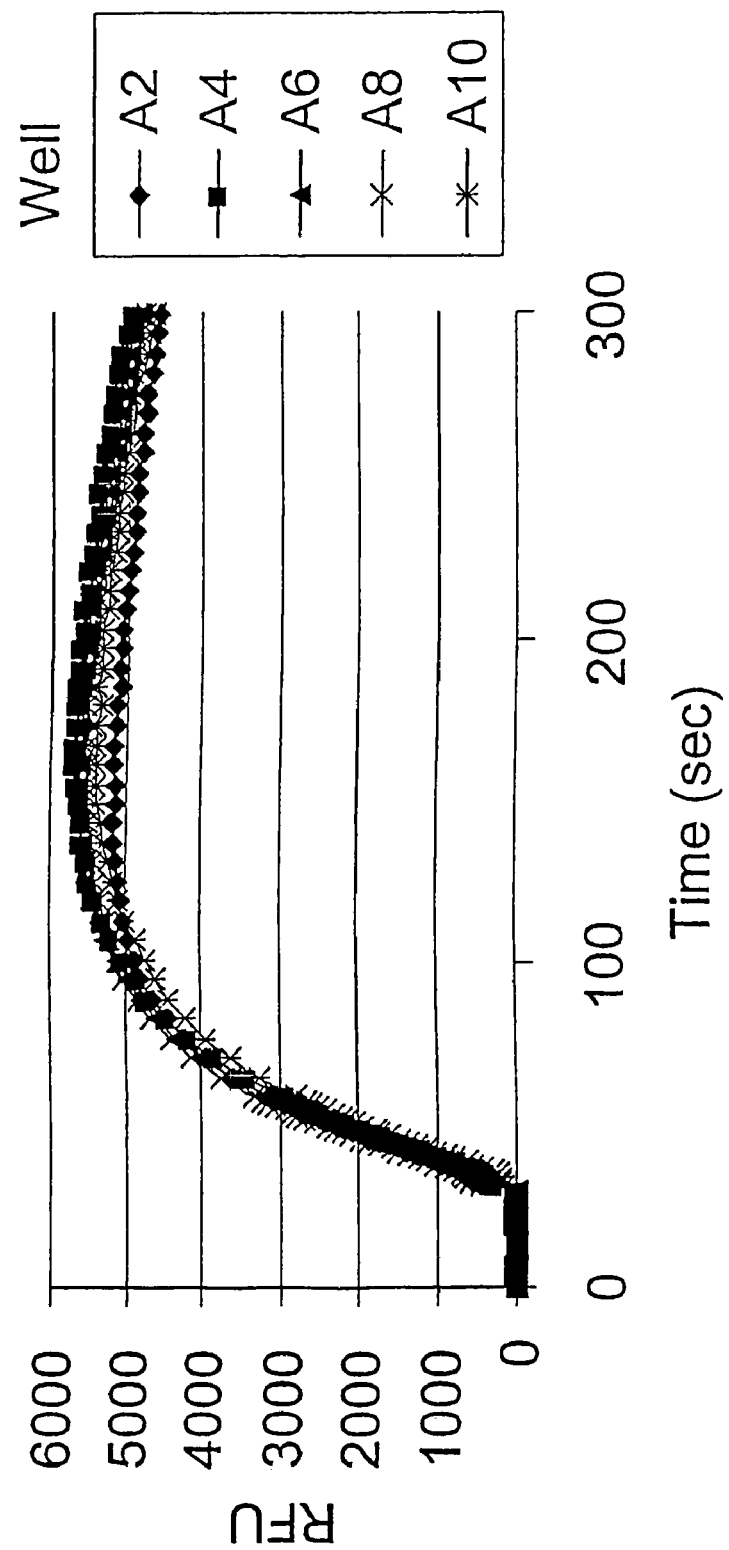

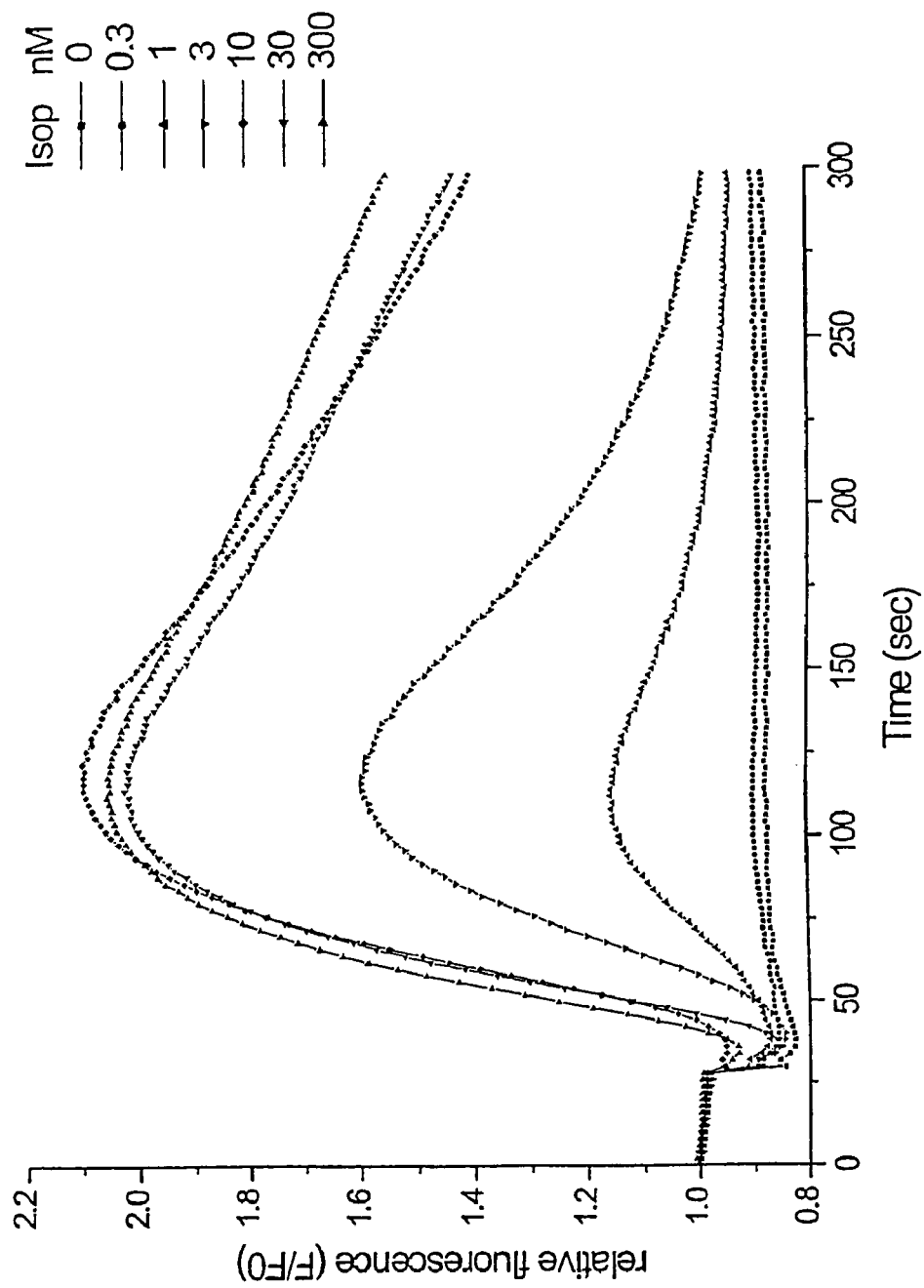
Fig. 11. A kinetic assay with calcium-sensitive dye

Fig. 12
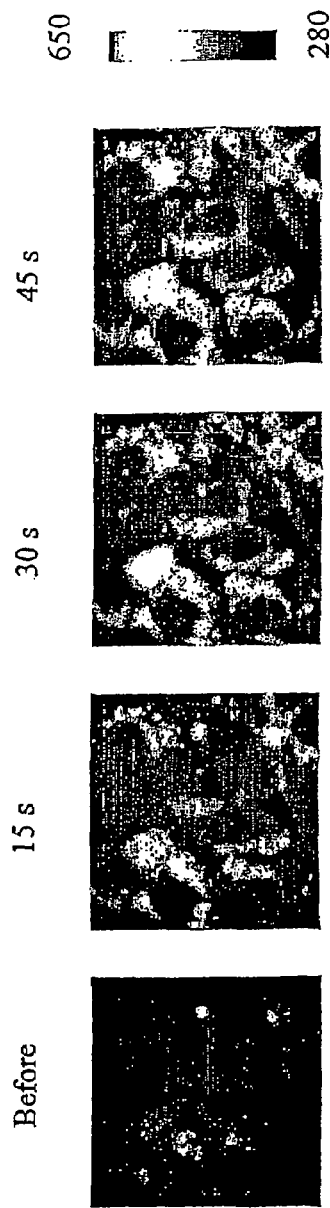
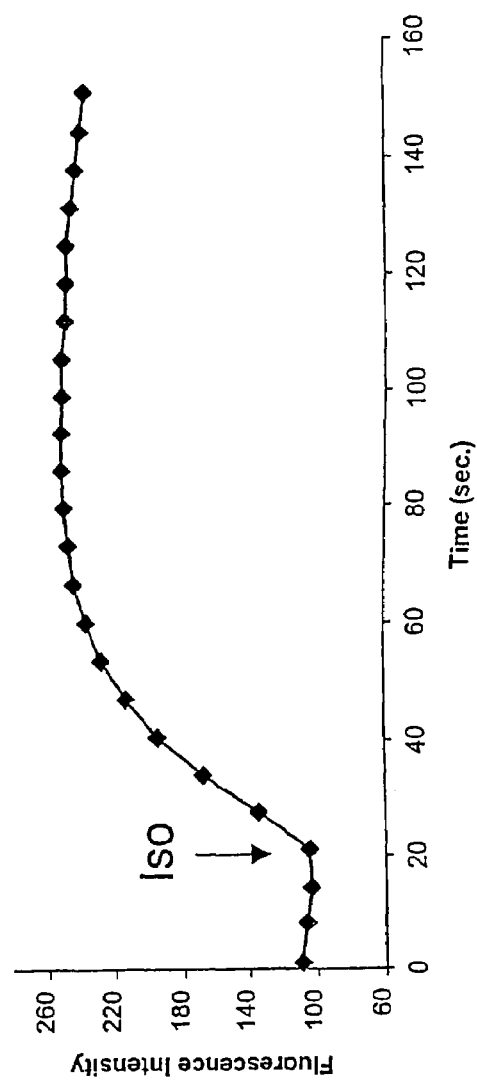
A
B

FIG. 15 Dose response curves obtained with CNG-assay

FIG. 17A  β2-Adrenoceptor Agonists and Antagonists Detection

Adrenergic compound-plate from BIOMOL

| | 1 | 2 | 3 | 4 |
|---|---|---|---|---|
| A | 2-[[beta-(4-HYDROXYPHENYL)ETHYL]AMINO-ETHYL]-1-TETRALONE<br>Alpha 1 adrenergic antagonist | GUANABENZ ACETATE<br>Alpha 2 adrenergic agonist | NICERGOLINE<br>Alpha adrenergic antagonist | CGP 12177 HCl<br>Beta 3 adrenergic agonist; beta 1 & 2 adrenergic antagonist |
| B | 5-METHYLURAPIDIL<br>Alpha 1A adrenergic antagonist | CGP 20712A METHANESULFONATE<br>Beta 1 adrenergic antagonist | CHLOROETHYL-CLONIDINE 2HCl<br>Alpha 1B adrenergic alkylating agent | (±)-ISOPROTERENOL HCl<br>Beta adrenergic agonist |
| C | IFENPRODIL<br>Alpha 1 adrenergic agonist | 2-[[4-(2-METHOXYPHENYL)PIPERAZIN-1-YL]METHYL]-6-METHYL-2,3-DIHYDROIMIDAZO[1,2C]QUINAZOLIN-5(6H)-ONE<br>Alpha 1 adrenergic antagonist | NAFTOPIDIL 2HCl<br>Alpha 1 adrenergic antagonist | 2-[(4-PHENYLPIPERAZIN-1-YL)METHYL]-2,3-DIHYDROIMIDAZO[1,2-C]QUINAZOLIN-5(6H)-ONE<br>Alpha 1 adrenergic antagonist |
| D | RILMENIDINE HEMIFUMARATE<br>Alpha 2 adrenergic agonist | UK 14,304<br>Alpha 2 adrenergic agonist | ARC 239 2HCl<br>Alpha 2B adrenergic antagonist | BRL 44408 MALEATE<br>Alpha 2A adrenergic antagonist |
| E | (±)-ATENOLOL<br>Beta adrenergic antagonist | R-(+)-ATENOLOL<br>Inactive isomer | S-(-)-ATENOLOL<br>Beta adrenergic antagonist | BETAXOLOL HCl<br>Beta 1 adrenergic antagonist |
| F | ICI 215,001 HCl<br>Active metabolite of ZD 7114 | ZD 7114 HCl<br>Beta 3 adrenergic agonist | PINDOLOL<br>Beta 3 adrenergic partial agonist | (S)-(-)-PINDOLOL<br>Beta 3 adrenergic partial agonist |
| G | PROPRANOLOL GLYCOL<br>Metabolite of propranolol | SOTALOL HCl<br>Beta adrenergic antagonist | MAPROTILINE HCl<br>Norepinephrine uptake inhibitor | NISOXETINE HCl<br>Norepinephrine uptake inhibitor |
| H | TIZANIDINE HCl<br>Alpha 2 adrenergic agonist | AH 11110A<br>Alpha 1B adrenoceptor ligand | EFAROXAN<br>Alpha 2 adrenergic antagonist | IDAZOXAN<br>Alpha 2 adrenergic antagonist |

NOTES:
1. Iso: ISOPROTERENOL
2. All compound concentration is 5 uM

*FIG. 17B*    To FIG. 17C →

Adrenergic compound-plate from BIOMOL

| 5 | 6 | 7 | 8 |
|---|---|---|---|
| R-(+)-PROPRANOLOL<br>Propranolol enantiomer (less active) | RAUWOLSCINE HCl<br>Alpha 2 adrenergic antagonist | AMOXAPINE<br>Norepinephrine uptake inhibitor | Blank |
| PHENTOLAMINE MESYLATE<br>Alpha adrenergic antagonist | A 61603 HBr<br>Alpha 1A adrenergic agonist | CIRAZOLINE HCl<br>Alpha 1 adrenergic agonist | M-6434<br>Alpha 1 adrenergic agonist |
| PRAZOSIN HCl<br>Alpha 1 adrenergic antagonist | RS 17053 HCl<br>Alpha 1A adrenergic antagonist | WB 4101 HCl<br>Alpha 1A adrenergic antagonist | 3-[2-[4-(2-CHLOROPHENYL)PIPERAZIN-1-YL]ETHYL]PYRIMIDO[5,4-B]INDOLE-2,4-DIONE<br>Alpha 1 adrenergic ligand |
| IMILOXAN HCl<br>Alpha 2 adrenergic antagonist | RS 79948 HCl<br>Alpha 2 adrenergic antagonist | SPIROXATRINE<br>Alpha 2 adrenergic ligand | YOHIMBINE HCl<br>Alpha 2 adrenergic antagonist |
| PRACTOLOL<br>Beta adrenergic antagonist; weak partial agonist | (S)-TIMOLOL MALEATE<br>Beta 1 adrenergic antagonist | XAMOTEROL HEMIFUMARATE<br>Beta 1 adrenergic partial agonist | CLENBUTEROL<br>Beta 2 adrenergic agonist. |
| CIMATEROL<br>Beta 1 adrenergic agonist | N-DESISOPROPYL-PROPRANOLOL HCl<br>Metabolite of propranolol | DOBUTAMINE HCl<br>Beta 1 adrenergic agonist | ICI 89406<br>Beta adrenergic antagonist |
| BOPINDOLOL MALONATE<br>Beta 1 adrenergic antagonist | (-)-CYANOPINDOLOL HEMIFUMARATE<br>Beta adrenergic antagonist | GUANFACINE HCl<br>Alpha 2 adrenergic agonist | ICI-118,551<br>Beta 2 adrenergic antagonist |
| SPIPERONE<br>Alpha 1 beta adrenergic antagonist | L-(-)-EPINEPHRINE-(+)-BITARTRATE<br>Endogenous alpha, beta adrenergic agonist | XYLAZINE HCl<br>Alpha 2 adrenergic agonist | L-(-)-NOREPINEPHRINE-(+)-BITARTRATE<br>Endogenous alpha, beta adrenergic agonist |

← FROM FIG. 17B

Adrenergic compund-plate from BIOMOL

| | 9 | 10 | 11 | 12 |
|---|---|---|---|---|
| | Blank | Blank | Blank | Iso |
| | OXYMETAZOLINE HCl<br>Alpha 2A adrenergic partial agonist; alpha 1A agonist | BMY 7378 2HCl<br>Alpha 1D adrenergic antagonist | CORYNANTHINE HCl<br>Alpha 1 adrenergic antagonist | Iso |
| | 3-[2-[4-(2-METHOXYPHENYL) PIPERAZIN-1-YL]ETHYL]-1,5-DIMETHYLPYRIMIDO [5,4-B]INDOLE-2,4-DIONE<br>Alpha 1 adrenergic ligand | 3-[2-[4-(2-METHOXYPHENYL) PIPERAZIN-1-YL]ETHYL] PYRIMIDO[5,4-B]INDOLE-2,4-DIONE<br>Alpha 1 adrenergic ligand | CLONIDINE HCl<br>Alpha 2 adrenergic agonist | Iso |
| | AGMATINE SULFATE<br>Endogenous Alpha 2 receptor agonist | DIHYDROERGOCRISTINE MESYLATE<br>Alpha adrenergic partial agonist | DIHYDROERGOTAMINE MESYLATE<br>Alpha adrenergic partial agonist | Iso |
| | PROCATEROL HCl<br>Beta 2 adrenergic agonist. | SALBUTAMOL SULFATE<br>Beta 2 adrenergic agonist. | BRL 37344 SODIUM SALT<br>Beta 3 adrenergic agonist. | Iso |
| | 1- NAPHTHOXYACETIC<br>Metabolite of propranolol | 1-NAPHTHOXYLACTIC<br>Metabolite of propranolol | PRONETHALOL HCl<br>Beta adrenergic antagonist | Iso |
| | PHENOXYBENZAMINE HCl<br>Alpha adrenergic antagonist | PROPRANOLOL HCl<br>Beta adrenergic antagonist | S(-)-PROPRANOLOL HCl<br>Beta adrenergic antagonist | Iso |
| | NYLIDRIN HCl<br>Beta adrenergic agonist | ALPRENOLOL HCl<br>Beta adrenergic antagonist | IMIPRAMINE HCl<br>Norepinephrine uptake inhibitor | Iso |

← FROM FIG. 17B (Cont'd)

*FIG. 17B (Cont'd)*

Adrenergic compound-plate from BIOMOL

| 5 | 6 | 7 | 8 |
|---|---|---|---|
| | | | Blank |
| R-(+)-PROPRANOLOL  Propranolol enantiomer (less active) | RAUWOLSCINE HCl  Alpha 2 adrenergic antagonist | AMOXAPINE  Norepinephrine uptake inhibitor | |
| PHENTOLAMINE MESYLATE  Alpha adrenergic antagonist | A 61603 HBr  Alpha 1A adrenergic agonist | CIRAZOLINE HCl  Alpha 1 adrenergic agonist | M-6434  Alpha 1 adrenergic agonist |
| PRAZOSIN HCl  Alpha 1 adrenergic antagonist | RS 17053 HCl  Alpha 1A adrenergic antagonist | WB 4101 HCl  Alpha 1A adrenergic antagonist | 3-[2-[4-(2-CHLOROPHENYL)PIPERAZIN-1-YL)ETHYL]PYRIMIDO[5,4-B]INDOLE-2,4-DIONE  Alpha 1 adrenergic ligand |
| IMILOXAN HCl  Alpha 2 adrenergic antagonist | RS 79948 HCl  Alpha 2 adrenergic antagonist | SPIROXATRINE  Alpha 2 adrenergic ligand | YOHIMBINE HCl  Alpha 2 adrenergic antagonist |
| PRACTOLOL  Beta 1 adrenergic antagonist; weak partial agonist | (S)-TIMOLOL MALEATE  Beta 1 adrenergic antagonist | XAMOTEROL HEMIFUMARATE  Beta 1 adrenergic partial agonist | CLENBUTEROL  Beta 2 adrenergic agonist. |
| CIMATEROL  Beta adrenergic agonist | N-DESISOPROPYL-PROPRANOLOL HCl  Metabolite of propranolol | DOBUTAMINE HCl  Beta 1 adrenergic agonist | ICI 89406  Beta adrenergic antagonist |
| BOPINDOLOL MALONATE  Beta 1 adrenergic antagonist | (-)-CYANOPINDOLOL HEMIFUMARATE  Beta adrenergic antagonist | GUANFACINE HCl  Alpha 2 adrenergic agonist | ICI-118,551  Beta 2 adrenergic antagonist |
| SPIPERONE  Alpha 1 beta adrenergic antagonist | L-(-)-EPINEPHRINE-(+)-BITARTRATE  Endogenous alpha, beta adrenergic agonist | XYLAZINE HCl  Alpha 2 adrenergic agonist | L-(-)-NOREPINEPHRINE-(+)-BITARTRATE  Endogenous alpha, beta adrenergic agonist |

← From FIG. 17B      To FIG. 17D →

FIG. 17C

Adrenergic compund-plate from BIOMOL

| | 9 | 10 | 11 | 12 |
|---|---|---|---|---|
| | Blank | Blank | Blank | Iso |
| | OXYMETAZOLINE HCl<br>*Alpha 2A adrenergic partial agonist; alpha 1A agonist* | BMY 7378 2HCl<br>*Alpha 1D adrenergic antagonist* | CORYNANTHINE HCl<br>*Alpha 1 adrenergic antagonist* | Iso |
| | 3-[2-[4-(2-METHOXYPHENYL) PIPERAZIN-1-YL]ETHYL]-1,5-DIMETHYLPYRIMIDO [5,4-B]INDOLE-2,4-DIONE<br>*Alpha 1 adrenergic ligand* | 3-[2-[4-(2-METHOXYPHENYL) PIPERAZIN-1-YL]ETHYL] PYRIMIDO[5,4-B]INDOLE-2,4-DIONE<br>*Alpha 1 adrenergic ligand* | CLONIDINE HCl<br>*Alpha 2 adrenergic agonist* | Iso |
| | AGMATINE SULFATE<br>*Endogenous Alpha 2 receptor agonist* | DIHYDROERGOCRISTINE MESYLATE<br>*Alpha adrenergic partial agonist* | DIHYDROERGOTAMINE MESYLATE<br>*Alpha adrenergic partial agonist* | Iso |
| | PROCATEROL HCl<br>*Beta 2 adrenergic agonist.* | SALBUTAMOL SULFATE<br>*Beta 2 adrenergic agonist.* | BRL 37344 SODIUM SALT<br>*Beta 3 adrenergic agonist.* | Iso |
| | 1- NAPHTHOXYACETIC<br>*Metabolite of propranolol* | 1-NAPHTHOXYLACTIC<br>*Metabolite of propranolol* | PRONETHALOL HCl<br>*Beta adrenergic antagonist* | Iso |
| | PHENOXYBENZAMINE HCl<br>*Alpha adrenergic antagonist* | PROPRANOLOL HCl<br>*Beta adrenergic antagonist* | S(-)-PROPRANOLOL HCl<br>*Beta adrenergic antagonist* | Iso |
| | NYLIDRIN HCl<br>*Beta adrenergic agonist* | ALPRENOLOL HCl<br>*Beta adrenergic antagonist* | IMIPRAMINE HCl<br>*Norepinephrine uptake inhibitor* | Iso |

*FIG. 17D*

← From FIG. 17C

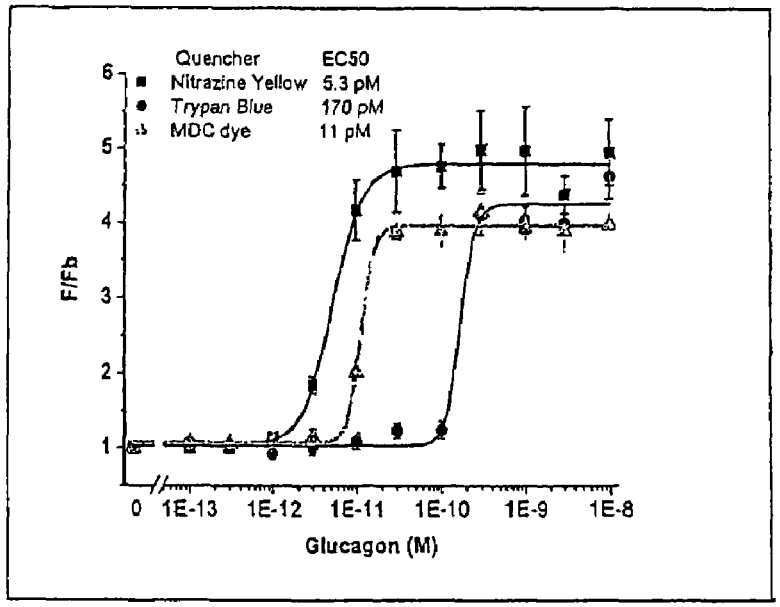
FIG. 22
FIG. 23
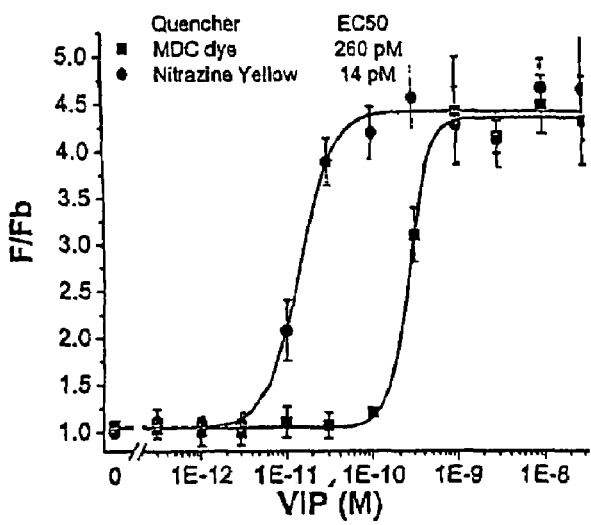

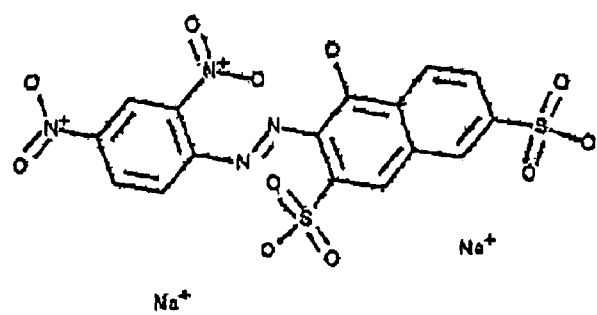
Fig. 25. Nitrazine Yellow

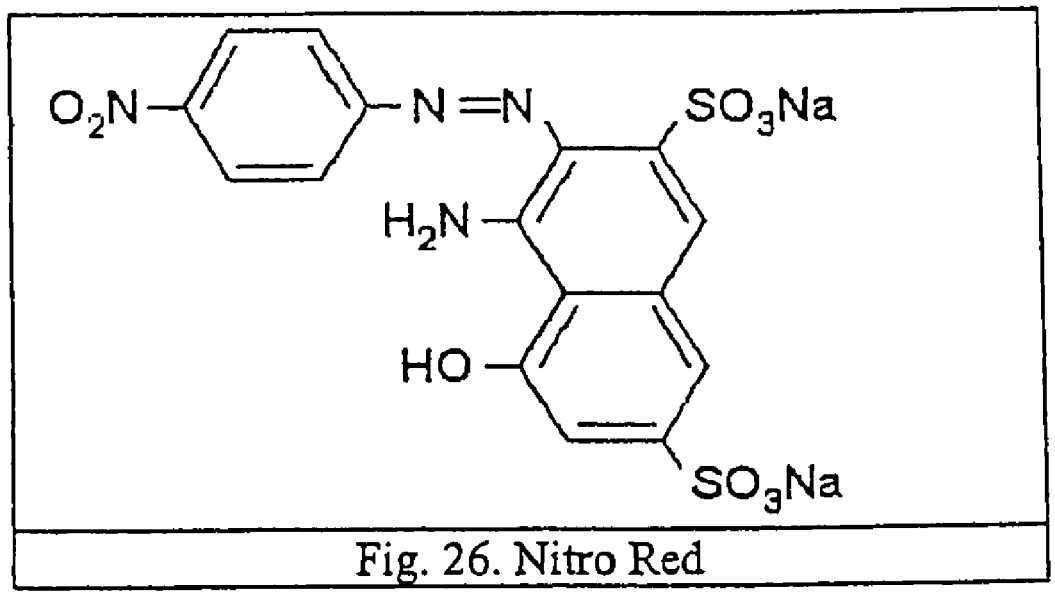
Fig. 26. Nitro Red

SEQUENCE LISTING

<160> NUMBER OF SEQ ID NOS: 23

<210> SEQ ID NO 1
<211> LENGTH: 1995
<212> TYPE: DNA
<213> ORGANISM: Rattus norvegicus
<220> FEATURE:
<221> NAME/KEY: CDS
<222> LOCATION: (1)..(1992)
<223> OTHER INFORMATION:

<400> SEQUENCE: 1

```
atg atg acc gaa aaa tcc aat ggt gtg aaa agc tct cca gct aat aac      48
Met Met Thr Glu Lys Ser Asn Gly Val Lys Ser Ser Pro Ala Asn Asn
1               5                   10                  15 cat aac cat cat cct cct cct tct atc aag gcc aat ggc aaa gat gac      96
His Asn His His Pro Pro Pro Ser Ile Lys Ala Asn Gly Lys Asp Asp
                20                  25                  30 cac agg gca gga agc aga cca cag tct gtg gca gct gat gat gac act     144
His Arg Ala Gly Ser Arg Pro Gln Ser Val Ala Ala Asp Asp Asp Thr
            35                  40                  45 tct cca gaa cta caa agg ctg gca gag atg gat acc cct cgg agg ggg     192
Ser Pro Glu Leu Gln Arg Leu Ala Glu Met Asp Thr Pro Arg Arg Gly
        50                  55                  60 agg ggt ggc ttc caa agg att gtt cgc ctg gtg ggg gtc atc agg gac     240
Arg Gly Gly Phe Gln Arg Ile Val Arg Leu Val Gly Val Ile Arg Asp
65                  70                  75                  80 tgg gcc aac aag aat ttc cgt gaa gag gaa cca agg cct gac tcc ttc     288
Trp Ala Asn Lys Asn Phe Arg Glu Glu Glu Pro Arg Pro Asp Ser Phe
                85                  90                  95 cta gag cgt ttc cgt ggg cca gaa ctc cag act gtg aca acc cat cag     336
Leu Glu Arg Phe Arg Gly Pro Glu Leu Gln Thr Val Thr Thr His Gln
                100                 105                 110 ggg gat gac aaa ggc ggc aag gac ggc gag gga aag ggc acc aaa aag     384
Gly Asp Asp Lys Gly Gly Lys Asp Gly Glu Gly Lys Gly Thr Lys Lys
            115                 120                 125 aaa ttt gaa ctg ttt gtt ttg gac cca gcc gga gac tgg tat tac cgt     432
Lys Phe Glu Leu Phe Val Leu Asp Pro Ala Gly Asp Trp Tyr Tyr Arg
        130                 135                 140 tgg ttg ttt gtc att gcc atg cct gtt ctt tac aac tgg tgc ctg ttg     480
Trp Leu Phe Val Ile Ala Met Pro Val Leu Tyr Asn Trp Cys Leu Leu
```

```
                                           -continued
145                 150                 155                 160 gtg gcc aga gcc tgc ttc agt gat cta cag aga aac tat ttt gtg gta    528
Val Ala Arg Ala Cys Phe Ser Asp Leu Gln Arg Asn Tyr Phe Val Val
                165                 170                 175 tgg ctg gtg ctg gac tac ttc tca gac act gtc tat atc gca gac ctc    576
Trp Leu Val Leu Asp Tyr Phe Ser Asp Thr Val Tyr Ile Ala Asp Leu
            180                 185                 190 atc att cgg ctg cgc aca ggc ttc cta gaa cag ggc ctc ttg gtc aaa    624
Ile Ile Arg Leu Arg Thr Gly Phe Leu Glu Gln Gly Leu Leu Val Lys
        195                 200                 205 gat ccc aag aaa ttg cga gac aac tat att cac act ttg cag ttc aaa    672
Asp Pro Lys Lys Leu Arg Asp Asn Tyr Ile His Thr Leu Gln Phe Lys
    210                 215                 220 ttg gat gtg gct tct atc att ccc act gac ctt atc tat ttt gct gtg    720
Leu Asp Val Ala Ser Ile Ile Pro Thr Asp Leu Ile Tyr Phe Ala Val
225                 230                 235                 240 ggt atc cac agc cct gag gta cgc ttc aac cgt cta tta cac ttt gcc    768
Gly Ile His Ser Pro Glu Val Arg Phe Asn Arg Leu Leu His Phe Ala
                245                 250                 255 cgt atg ttt gag ttc ttt gac cgc act gag aca cgc acc agc tac ccc    816
Arg Met Phe Glu Phe Phe Asp Arg Thr Glu Thr Arg Thr Ser Tyr Pro
            260                 265                 270 aac atc ttc cga atc agc aat ctg gtc ctt tac atc ttg gtc atc atc    864
Asn Ile Phe Arg Ile Ser Asn Leu Val Leu Tyr Ile Leu Val Ile Ile
        275                 280                 285 cac tgg aat gct tgt att tat tat gtt att tct aag tcc att ggc ttt    912
His Trp Asn Ala Cys Ile Tyr Tyr Val Ile Ser Lys Ser Ile Gly Phe
    290                 295                 300 gga gtt gac acc tgg gtt tac ccc aac att act gac cct gaa tat ggc    960
Gly Val Asp Thr Trp Val Tyr Pro Asn Ile Thr Asp Pro Glu Tyr Gly
305                 310                 315                 320 tac ctg gct aga gag tac att tac tgt ctt tac tgg tcc aca ctg acc   1008
Tyr Leu Ala Arg Glu Tyr Ile Tyr Cys Leu Tyr Trp Ser Thr Leu Thr
                325                 330                 335 ctc acc acc att gga gag aca cca ccc cct gta aag gat gag gag tac   1056
Leu Thr Thr Ile Gly Glu Thr Pro Pro Pro Val Lys Asp Glu Glu Tyr
            340                 345                 350 cta ttt gtc atc ttt gac ttc ttg att ggt gtc ctc atc ttt gcc act   1104
Leu Phe Val Ile Phe Asp Phe Leu Ile Gly Val Leu Ile Phe Ala Thr
        355                 360                 365 att gtg gga aat gtg ggc tcc atg atc tcc aac atg aat gcc aca cga   1152
Ile Val Gly Asn Val Gly Ser Met Ile Ser Asn Met Asn Ala Thr Arg
    370                 375                 380 gca gag ttc cag gcc aag att gat gct gtc aaa cac tac atg cag ttc   1200
Ala Glu Phe Gln Ala Lys Ile Asp Ala Val Lys His Tyr Met Gln Phe
385                 390                 395                 400 cga aag gtc agc aaa gac atg gaa gcc aag gtc atc aaa tgg ttt gac   1248
Arg Lys Val Ser Lys Asp Met Glu Ala Lys Val Ile Lys Trp Phe Asp
                405                 410                 415 tac ttg tgg acc aat aag aag aca gta gat gaa cga gaa gtc ctc aag   1296
Tyr Leu Trp Thr Asn Lys Lys Thr Val Asp Glu Arg Glu Val Leu Lys
            420                 425                 430 aac ctg cca gca aag ctc agg gct gag ata gcc att aat gtt cac ttg   1344
Asn Leu Pro Ala Lys Leu Arg Ala Glu Ile Ala Ile Asn Val His Leu
        435                 440                 445 tcc act ctg aag aaa gtg cgc ata ttc cag gat tgt gaa gct ggc cta   1392
Ser Thr Leu Lys Lys Val Arg Ile Phe Gln Asp Cys Glu Ala Gly Leu
    450                 455                 460 ctg gtg gaa ctg gta ctg aag ctt cgt cct cag gtc ttt agt cct gga   1440
```

```
Leu Val Glu Leu Val Leu Lys Leu Arg Pro Gln Val Phe Ser Pro Gly
465                 470                 475                 480 gat tat att tgc cgt aag ggg gac att ggc aag gaa atg tac atc atc    1488
Asp Tyr Ile Cys Arg Lys Gly Asp Ile Gly Lys Glu Met Tyr Ile Ile
                485                 490                 495 aag gag ggc aag ttg gca gtg gta gct gat gat ggc gtg act cag tat    1536
Lys Glu Gly Lys Leu Ala Val Val Ala Asp Asp Gly Val Thr Gln Tyr
            500                 505                 510 gcc ttg ctc tca gct ggg agc tgc ttt ggt gag att agt atc ctt aac    1584
Ala Leu Leu Ser Ala Gly Ser Cys Phe Gly Glu Ile Ser Ile Leu Asn
        515                 520                 525 att aag ggt agc aaa atg ggc aat cga cgt act gct aat atc cgt agc    1632
Ile Lys Gly Ser Lys Met Gly Asn Arg Arg Thr Ala Asn Ile Arg Ser
    530                 535                 540 ctg ggc tac tca gat ctc ttc tgc ttg tcc aag gac gat ctt atg gaa    1680
Leu Gly Tyr Ser Asp Leu Phe Cys Leu Ser Lys Asp Asp Leu Met Glu
545                 550                 555                 560 gct gta act gag tat cct gat gcc aag aag gtc ctg gag gaa cgg ggt    1728
Ala Val Thr Glu Tyr Pro Asp Ala Lys Lys Val Leu Glu Glu Arg Gly
                565                 570                 575 agg gag atc ctg atg aag gaa ggt cta ctg gat gag aat gaa gtg gca    1776
Arg Glu Ile Leu Met Lys Glu Gly Leu Leu Asp Glu Asn Glu Val Ala
            580                 585                 590 gct agt atg gag gta gat gtt cag gag aag ctg gaa cag ttg gag aca    1824
Ala Ser Met Glu Val Asp Val Gln Glu Lys Leu Glu Gln Leu Glu Thr
        595                 600                 605 aac atg gat acc ttg tac act cgc ttt gcc cgc ctg ctg gct gag tac    1872
Asn Met Asp Thr Leu Tyr Thr Arg Phe Ala Arg Leu Leu Ala Glu Tyr
    610                 615                 620 act ggg gcc cag cag aag ctc aag caa cgc atc aca gtg cta gag acc    1920
Thr Gly Ala Gln Gln Lys Leu Lys Gln Arg Ile Thr Val Leu Glu Thr
625                 630                 635                 640 aag atg aaa cag aac cat gag gat gat tat cta tca gat ggg ata aac    1968
Lys Met Lys Gln Asn His Glu Asp Asp Tyr Leu Ser Asp Gly Ile Asn
                645                 650                 655 act cct gag cca act gct gct gaa taa                                1995
Thr Pro Glu Pro Thr Ala Ala Glu
            660

<210> SEQ ID NO 2
<211> LENGTH: 664
<212> TYPE: PRT
<213> ORGANISM: Rattus norvegicus

<400> SEQUENCE: 2

Met Met Thr Glu Lys Ser Asn Gly Val Lys Ser Ser Pro Ala Asn Asn
1               5                   10                  15

His Asn His His Pro Pro Ser Ile Lys Ala Asn Gly Lys Asp Asp
                20                  25                  30

His Arg Ala Gly Ser Arg Pro Gln Ser Val Ala Ala Asp Asp Thr
            35                  40                  45

Ser Pro Glu Leu Gln Arg Leu Ala Glu Met Asp Thr Pro Arg Arg Gly
    50                  55                  60

Arg Gly Gly Phe Gln Arg Ile Val Arg Leu Val Gly Val Ile Arg Asp
65                  70                  75                  80

Trp Ala Asn Lys Asn Phe Arg Glu Glu Pro Arg Pro Asp Ser Phe
                85                  90                  95

Leu Glu Arg Phe Arg Gly Pro Glu Leu Gln Thr Val Thr Thr His Gln
            100                 105                 110
```

-continued

Gly Asp Asp Lys Gly Lys Asp Gly Glu Gly Lys Gly Thr Lys Lys
            115                 120                 125

Lys Phe Glu Leu Phe Val Leu Asp Pro Ala Gly Asp Trp Tyr Tyr Arg
            130                 135                 140

Trp Leu Phe Val Ile Ala Met Pro Val Leu Tyr Asn Trp Cys Leu Leu
145                 150                 155                 160

Val Ala Arg Ala Cys Phe Ser Asp Leu Gln Arg Asn Tyr Phe Val Val
                165                 170                 175

Trp Leu Val Leu Asp Tyr Phe Ser Asp Thr Val Tyr Ile Ala Asp Leu
            180                 185                 190

Ile Ile Arg Leu Arg Thr Gly Phe Leu Glu Gln Gly Leu Leu Val Lys
            195                 200                 205

Asp Pro Lys Lys Leu Arg Asp Asn Tyr Ile His Thr Leu Gln Phe Lys
            210                 215                 220

Leu Asp Val Ala Ser Ile Ile Pro Thr Asp Leu Ile Tyr Phe Ala Val
225                 230                 235                 240

Gly Ile His Ser Pro Glu Val Arg Phe Asn Arg Leu Leu His Phe Ala
                245                 250                 255

Arg Met Phe Glu Phe Phe Asp Arg Thr Glu Thr Arg Thr Ser Tyr Pro
                260                 265                 270

Asn Ile Phe Arg Ile Ser Asn Leu Val Leu Tyr Ile Leu Val Ile Ile
            275                 280                 285

His Trp Asn Ala Cys Ile Tyr Tyr Val Ile Ser Lys Ser Ile Gly Phe
            290                 295                 300

Gly Val Asp Thr Trp Val Tyr Pro Asn Ile Thr Asp Pro Glu Tyr Gly
305                 310                 315                 320

Tyr Leu Ala Arg Glu Tyr Ile Tyr Cys Leu Tyr Trp Ser Thr Leu Thr
                325                 330                 335

Leu Thr Thr Ile Gly Glu Thr Pro Pro Pro Val Lys Asp Glu Glu Tyr
            340                 345                 350

Leu Phe Val Ile Phe Asp Phe Leu Ile Gly Val Leu Ile Phe Ala Thr
            355                 360                 365

Ile Val Gly Asn Val Gly Ser Met Ile Ser Asn Met Asn Ala Thr Arg
370                 375                 380

Ala Glu Phe Gln Ala Lys Ile Asp Ala Val Lys His Tyr Met Gln Phe
385                 390                 395                 400

Arg Lys Val Ser Lys Asp Met Glu Ala Lys Val Ile Lys Trp Phe Asp
                405                 410                 415

Tyr Leu Trp Thr Asn Lys Lys Thr Val Asp Glu Arg Glu Val Leu Lys
            420                 425                 430

Asn Leu Pro Ala Lys Leu Arg Ala Glu Ile Ala Ile Asn Val His Leu
            435                 440                 445

Ser Thr Leu Lys Lys Val Arg Ile Phe Gln Asp Cys Glu Ala Gly Leu
            450                 455                 460

Leu Val Glu Leu Val Leu Lys Leu Arg Pro Gln Val Phe Ser Pro Gly
465                 470                 475                 480

Asp Tyr Ile Cys Arg Lys Gly Asp Ile Gly Lys Glu Met Tyr Ile Ile
                485                 490                 495

Lys Glu Gly Lys Leu Ala Val Val Ala Asp Asp Gly Val Thr Gln Tyr
            500                 505                 510

Ala Leu Leu Ser Ala Gly Ser Cys Phe Gly Glu Ile Ser Ile Leu Asn
            515                 520                 525

```
Ile Lys Gly Ser Lys Met Gly Asn Arg Arg Thr Ala Asn Ile Arg Ser
    530                 535                 540

Leu Gly Tyr Ser Asp Leu Phe Cys Leu Ser Lys Asp Asp Leu Met Glu
545                 550                 555                 560

Ala Val Thr Glu Tyr Pro Asp Ala Lys Lys Val Leu Glu Glu Arg Gly
                565                 570                 575

Arg Glu Ile Leu Met Lys Glu Gly Leu Leu Asp Glu Asn Glu Val Ala
                580                 585                 590

Ala Ser Met Glu Val Asp Val Gln Glu Lys Leu Glu Gln Leu Glu Thr
        595                 600                 605

Asn Met Asp Thr Leu Tyr Thr Arg Phe Ala Arg Leu Leu Ala Glu Tyr
    610                 615                 620

Thr Gly Ala Gln Gln Lys Leu Lys Gln Arg Ile Thr Val Leu Glu Thr
625                 630                 635                 640

Lys Met Lys Gln Asn His Glu Asp Asp Tyr Leu Ser Asp Gly Ile Asn
                645                 650                 655

Thr Pro Glu Pro Thr Ala Ala Glu
            660

<210> SEQ ID NO 3
<211> LENGTH: 1995
<212> TYPE: DNA
<213> ORGANISM: Rattus norvegicus
<220> FEATURE:
<221> NAME/KEY: CDS
<222> LOCATION: (1)..(1992)
<223> OTHER INFORMATION:

<400> SEQUENCE: 3 atg atg acc gaa aaa tcc aat ggt gtg aaa agc tct cca gct aat aac      48
Met Met Thr Glu Lys Ser Asn Gly Val Lys Ser Ser Pro Ala Asn Asn
1               5                   10                  15 cat aac cat cat cct cct cct tct atc aag gcc aat ggc aaa gat gac      96
His Asn His His Pro Pro Pro Ser Ile Lys Ala Asn Gly Lys Asp Asp
                20                  25                  30 cac agg gca gga agc aga cca cag tct gtg gca gct gat gat gac act     144
His Arg Ala Gly Ser Arg Pro Gln Ser Val Ala Ala Asp Asp Asp Thr
            35                  40                  45 tct cca gaa cta caa agg ctg gca gag atg gat acc cct cgg agg ggg     192
Ser Pro Glu Leu Gln Arg Leu Ala Glu Met Asp Thr Pro Arg Arg Gly
        50                  55                  60 agg ggt ggc ttc caa agg att gtt cgc ctg gtg ggg gtc atc agg gac     240
Arg Gly Gly Phe Gln Arg Ile Val Arg Leu Val Gly Val Ile Arg Asp
65                  70                  75                  80 tgg gcc aac aag aat ttc cgt gaa gag gaa cca agg cct gac tcc ttc     288
Trp Ala Asn Lys Asn Phe Arg Glu Glu Glu Pro Arg Pro Asp Ser Phe
                85                  90                  95 cta gag cgt ttc cgt ggg cca gaa ctc cag act gtg aca acc cat cag     336
Leu Glu Arg Phe Arg Gly Pro Glu Leu Gln Thr Val Thr Thr His Gln
                100                 105                 110 ggg gat gac aaa ggc ggc aag gac ggc gag gga aag ggc acc aaa aag     384
Gly Asp Asp Lys Gly Gly Lys Asp Gly Glu Gly Lys Gly Thr Lys Lys
            115                 120                 125 aaa ttt gaa ctg ttt gtt ttg gac cca gcc gga gac tgg tat tac cgt     432
Lys Phe Glu Leu Phe Val Leu Asp Pro Ala Gly Asp Trp Tyr Tyr Arg
        130                 135                 140 tgg ttg ttt gtc att gcc atg cct gtt ctt tac aac tgg tgc ctg ttg     480
Trp Leu Phe Val Ile Ala Met Pro Val Leu Tyr Asn Trp Cys Leu Leu
145                 150                 155                 160
```

-continued

| | |
|---|---|
| gtg gcc aga gcc tgc ttc agt gat cta cag aga aac tat ttt gtg gta<br>Val Ala Arg Ala Cys Phe Ser Asp Leu Gln Arg Asn Tyr Phe Val Val<br>              165                      170                 175 | 528 |
| tgg ctg gtg ctg gac tac ttc tca gac act gtc tat atc gca gac ctc<br>Trp Leu Val Leu Asp Tyr Phe Ser Asp Thr Val Tyr Ile Ala Asp Leu<br>180                     185                    190 | 576 |
| atc att cgg ctg cgc aca ggc ttc cta gaa cag ggg ctc ttg gtc aaa<br>Ile Ile Arg Leu Arg Thr Gly Phe Leu Glu Gln Gly Leu Leu Val Lys<br>        195                    200 | 624 |
| gat ccc aag aaa ttg cga gac aac tat att cac act ttg cag ttc aaa<br>Asp Pro Lys Lys Leu Arg Asp Asn Tyr Ile His Thr Leu Gln Phe Lys<br>210                     215                    220 | 672 |
| ttg gat gtg gct tct atc att ccc act gac ctt atc tat ttt gct gtg<br>Leu Asp Val Ala Ser Ile Ile Pro Thr Asp Leu Ile Tyr Phe Ala Val<br>225                     230                    235                 240 | 720 |
| ggt atc cac agc cct gag gta cgc ttc aac cgt cta tta cac ttt gcc<br>Gly Ile His Ser Pro Glu Val Arg Phe Asn Arg Leu Leu His Phe Ala<br>                     245                    250                    255 | 768 |
| cgt atg ttt gag ttc ttt gac cgc act gag aca cgc acc agc tac ccc<br>Arg Met Phe Glu Phe Phe Asp Arg Thr Glu Thr Arg Thr Ser Tyr Pro<br>                260                      265                 270 | 816 |
| aac atc ttc cga atc agc aat ctg gtc ctt tac atc ttg gtc atc atc<br>Asn Ile Phe Arg Ile Ser Asn Leu Val Leu Tyr Ile Leu Val Ile Ile<br>275                     280                    285 | 864 |
| cac tgg aat gct tgt att tat tat gtt att tct aag tcc att ggc ttt<br>His Trp Asn Ala Cys Ile Tyr Tyr Val Ile Ser Lys Ser Ile Gly Phe<br>        290                    295                    300 | 912 |
| gga gtt gac acc tgg gtt tac ccc aac att act gac cct gaa tat ggc<br>Gly Val Asp Thr Trp Val Tyr Pro Asn Ile Thr Asp Pro Glu Tyr Gly<br>305                     310                    315                 320 | 960 |
| tac ctg gct aga gag tac att tac tgt ctt tac tgg tcc aca ctg acc<br>Tyr Leu Ala Arg Glu Tyr Ile Tyr Cys Leu Tyr Trp Ser Thr Leu Thr<br>                     325                    330                 335 | 1008 |
| ctc acc acc att gga gag aca cca ccc cct gta aag gat gag gag tac<br>Leu Thr Thr Ile Gly Glu Thr Pro Pro Pro Val Lys Asp Glu Glu Tyr<br>                    340                    345                 350 | 1056 |
| cta ttt gtc atc ttt gac ttc ttg att ggt gtc ctc atc ttt gcc act<br>Leu Phe Val Ile Phe Asp Phe Leu Ile Gly Val Leu Ile Phe Ala Thr<br>355                     360                    365 | 1104 |
| att gtg gga aat gtg ggc tcc atg atc tcc aac atg aat gcc aca cga<br>Ile Val Gly Asn Val Gly Ser Met Ile Ser Asn Met Asn Ala Thr Arg<br>        370                    375                    380 | 1152 |
| gca gag ttc cag gcc aag att gat gct gtc aaa cac tac atg cag ttc<br>Ala Glu Phe Gln Ala Lys Ile Asp Ala Val Lys His Tyr Met Gln Phe<br>385                     390                    395                 400 | 1200 |
| cga aag gtc agc aaa gac atg gaa gcc aag gtc atc aaa tgg ttt gac<br>Arg Lys Val Ser Lys Asp Met Glu Ala Lys Val Ile Lys Trp Phe Asp<br>                     405                    410                 415 | 1248 |
| tac ttg tgg acc aat aag aag aca gta gat gaa cga gaa gtc ctc aag<br>Tyr Leu Trp Thr Asn Lys Lys Thr Val Asp Glu Arg Glu Val Leu Lys<br>                420                      425                 430 | 1296 |
| aac ctg cca gca aag ctc agg gct gag ata gcc att aat gtt cac ttg<br>Asn Leu Pro Ala Lys Leu Arg Ala Glu Ile Ala Ile Asn Val His Leu<br>435                     440                    445 | 1344 |
| tcc act ctg aag aaa gtg cgc ata ttc cag gat tgt gaa gct ggc cta<br>Ser Thr Leu Lys Lys Val Arg Ile Phe Gln Asp Cys Glu Ala Gly Leu<br>        450                    455                    460 | 1392 |
| ctg gtg gaa ctg gta ctg aag ctt cgt cct cag gtc ttt agt cct gga<br>Leu Val Glu Leu Val Leu Lys Leu Arg Pro Gln Val Phe Ser Pro Gly<br>465                     470                    475                 480 | 1440 |

| | | | | | | | | | | | | | | |
|---|---|---|---|---|---|---|---|---|---|---|---|---|---|---|
| gat | tat | att | tgc | cgt | aag | ggg | gac | att | ggc | aag | gaa | atg | tac | atc | atc | 1488 |
| Asp | Tyr | Ile | Cys | Arg | Lys | Gly | Asp | Ile | Gly | Lys | Glu | Met | Tyr | Ile | Ile | |
| | | | | 485 | | | | | 490 | | | | | 495 | | | aag gag ggc aag ttg gca gtg gta gct gat gat ggc gtg act cag tat    1536
Lys Glu Gly Lys Leu Ala Val Val Ala Asp Asp Gly Val Thr Gln Tyr
            500                 505                 510 gcc ttg ctc tca gct ggg agc tgc ttt ggt gag att agt atc ctt aac    1584
Ala Leu Leu Ser Ala Gly Ser Cys Phe Gly Glu Ile Ser Ile Leu Asn
        515                 520                 525 att aag ggt agc aaa atg ggc aat cga cgt act gct aat atc cgt agc    1632
Ile Lys Gly Ser Lys Met Gly Asn Arg Arg Thr Ala Asn Ile Arg Ser
530                 535                 540 ctg ggc tac tca gat ctc ttc tgc ttg tcc aag gac gat ctt atg gaa    1680
Leu Gly Tyr Ser Asp Leu Phe Cys Leu Ser Lys Asp Asp Leu Met Glu
545                 550                 555                 560 gct gta act gag gct cct gat gcc aag aag gtc ctg gag gaa cgg ggt    1728
Ala Val Thr Glu Ala Pro Asp Ala Lys Lys Val Leu Glu Glu Arg Gly
                565                 570                 575 agg gag atc ctg atg aag gaa ggt cta ctg gat gag aat gaa gtg gca    1776
Arg Glu Ile Leu Met Lys Glu Gly Leu Leu Asp Glu Asn Glu Val Ala
            580                 585                 590 gct agt atg gag gta gat gtt cag gag aag ctg gaa cag ttg gag aca    1824
Ala Ser Met Glu Val Asp Val Gln Glu Lys Leu Glu Gln Leu Glu Thr
        595                 600                 605 aac atg gat acc ttg tac act cgc ttt gcc cgc ctg ctg gct gag tac    1872
Asn Met Asp Thr Leu Tyr Thr Arg Phe Ala Arg Leu Leu Ala Glu Tyr
610                 615                 620 act ggg gcc cag cag aag ctc aag caa cgc atc aca gtg cta gag acc    1920
Thr Gly Ala Gln Gln Lys Leu Lys Gln Arg Ile Thr Val Leu Glu Thr
625                 630                 635                 640 aag atg aaa cag aac cat gag gat gat tat cta tca gat ggg ata aac    1968
Lys Met Lys Gln Asn His Glu Asp Asp Tyr Leu Ser Asp Gly Ile Asn
                645                 650                 655 act cct gag cca act gct gct gaa taa    1995
Thr Pro Glu Pro Thr Ala Ala Glu
            660

<210> SEQ ID NO 4
<211> LENGTH: 664
<212> TYPE: PRT
<213> ORGANISM: Rattus norvegicus

<400> SEQUENCE: 4

Met Met Thr Glu Lys Ser Asn Gly Val Lys Ser Ser Pro Ala Asn Asn
1               5                   10                  15

His Asn His His Pro Pro Ser Ile Lys Ala Asn Gly Lys Asp Asp
            20                  25                  30

His Arg Ala Gly Ser Arg Pro Gln Ser Val Ala Ala Asp Asp Thr
        35                  40                  45

Ser Pro Glu Leu Gln Arg Leu Ala Glu Met Asp Thr Pro Arg Arg Gly
    50                  55                  60

Arg Gly Gly Phe Gln Arg Ile Val Arg Leu Gly Val Ile Arg Asp
65                  70                  75                  80

Trp Ala Asn Lys Asn Phe Arg Glu Glu Pro Arg Pro Asp Ser Phe
                85                  90                  95

Leu Glu Arg Phe Arg Gly Pro Glu Leu Gln Thr Val Thr Thr His Gln
            100                 105                 110

Gly Asp Asp Lys Gly Gly Lys Asp Gly Glu Gly Lys Gly Thr Lys Lys

-continued

```
                115                 120                 125
Lys Phe Glu Leu Phe Val Leu Asp Pro Ala Gly Asp Trp Tyr Tyr Arg
    130                 135                 140

Trp Leu Phe Val Ile Ala Met Pro Val Leu Tyr Asn Trp Cys Leu Leu
145                 150                 155                 160

Val Ala Arg Ala Cys Phe Ser Asp Leu Gln Arg Asn Tyr Phe Val Val
                165                 170                 175

Trp Leu Val Leu Asp Tyr Phe Ser Asp Thr Val Tyr Ile Ala Asp Leu
                180                 185                 190

Ile Ile Arg Leu Arg Thr Gly Phe Leu Glu Gln Gly Leu Leu Val Lys
            195                 200                 205

Asp Pro Lys Lys Leu Arg Asp Asn Tyr Ile His Thr Leu Gln Phe Lys
    210                 215                 220

Leu Asp Val Ala Ser Ile Ile Pro Thr Asp Leu Ile Tyr Phe Ala Val
225                 230                 235                 240

Gly Ile His Ser Pro Glu Val Arg Phe Asn Arg Leu Leu His Phe Ala
                245                 250                 255

Arg Met Phe Glu Phe Phe Asp Arg Thr Glu Thr Arg Thr Ser Tyr Pro
                260                 265                 270

Asn Ile Phe Arg Ile Ser Asn Leu Val Leu Tyr Ile Leu Val Ile Ile
            275                 280                 285

His Trp Asn Ala Cys Ile Tyr Tyr Val Ile Ser Lys Ser Ile Gly Phe
    290                 295                 300

Gly Val Asp Thr Trp Val Tyr Pro Asn Ile Thr Asp Pro Glu Tyr Gly
305                 310                 315                 320

Tyr Leu Ala Arg Glu Tyr Ile Tyr Cys Leu Tyr Trp Ser Thr Leu Thr
                325                 330                 335

Leu Thr Thr Ile Gly Glu Thr Pro Pro Pro Val Lys Asp Glu Glu Tyr
                340                 345                 350

Leu Phe Val Ile Phe Asp Phe Leu Ile Gly Val Leu Ile Phe Ala Thr
            355                 360                 365

Ile Val Gly Asn Val Gly Ser Met Ile Ser Asn Met Asn Ala Thr Arg
    370                 375                 380

Ala Glu Phe Gln Ala Lys Ile Asp Ala Val Lys His Tyr Met Gln Phe
385                 390                 395                 400

Arg Lys Val Ser Lys Asp Met Glu Ala Lys Val Ile Lys Trp Phe Asp
                405                 410                 415

Tyr Leu Trp Thr Asn Lys Lys Thr Val Asp Glu Arg Glu Val Leu Lys
                420                 425                 430

Asn Leu Pro Ala Lys Leu Arg Ala Glu Ile Ala Ile Asn Val His Leu
            435                 440                 445

Ser Thr Leu Lys Lys Val Arg Ile Phe Gln Asp Cys Glu Ala Gly Leu
    450                 455                 460

Leu Val Glu Leu Val Leu Lys Leu Arg Pro Gln Val Phe Ser Pro Gly
465                 470                 475                 480

Asp Tyr Ile Cys Arg Lys Gly Asp Ile Gly Lys Glu Met Tyr Ile Ile
                485                 490                 495

Lys Glu Gly Lys Leu Ala Val Val Ala Asp Asp Gly Val Thr Gln Tyr
                500                 505                 510

Ala Leu Leu Ser Ala Gly Ser Cys Phe Gly Glu Ile Ser Ile Leu Asn
            515                 520                 525

Ile Lys Gly Ser Lys Met Gly Asn Arg Arg Thr Ala Asn Ile Arg Ser
    530                 535                 540
```

```
Leu Gly Tyr Ser Asp Leu Phe Cys Leu Ser Lys Asp Asp Leu Met Glu
545                 550                 555                 560

Ala Val Thr Glu Ala Pro Asp Ala Lys Lys Val Leu Glu Glu Arg Gly
                565                 570                 575

Arg Glu Ile Leu Met Lys Glu Gly Leu Leu Asp Glu Asn Glu Val Ala
            580                 585                 590

Ala Ser Met Glu Val Asp Val Gln Glu Lys Leu Glu Gln Leu Glu Thr
        595                 600                 605

Asn Met Asp Thr Leu Tyr Thr Arg Phe Ala Arg Leu Leu Ala Glu Tyr
    610                 615                 620

Thr Gly Ala Gln Gln Lys Leu Lys Gln Arg Ile Thr Val Leu Glu Thr
625                 630                 635                 640

Lys Met Lys Gln Asn His Glu Asp Asp Tyr Leu Ser Asp Gly Ile Asn
                645                 650                 655

Thr Pro Glu Pro Thr Ala Ala Glu
                660
```

<210> SEQ ID NO 5
<211> LENGTH: 1995
<212> TYPE: DNA
<213> ORGANISM: Rattus norvegicus
<220> FEATURE:
<221> NAME/KEY: CDS
<222> LOCATION: (1)..(1992)
<223> OTHER INFORMATION:

<400> SEQUENCE: 5

```
atg atg acc gaa aaa tcc aat ggt gtg aaa agc tct cca gct aat aac      48
Met Met Thr Glu Lys Ser Asn Gly Val Lys Ser Ser Pro Ala Asn Asn
1               5                   10                  15 cat aac cat cat cct cct cct tct atc aag gcc aat ggc aaa gat gac      96
His Asn His His Pro Pro Pro Ser Ile Lys Ala Asn Gly Lys Asp Asp
                20                  25                  30 cac agg gca gga agc aga cca cag tct gtg gca gct gat gat gac act     144
His Arg Ala Gly Ser Arg Pro Gln Ser Val Ala Ala Asp Asp Asp Thr
            35                  40                  45 tct cca gaa cta caa agg ctg gca gag atg gat acc cct cgg agg ggg     192
Ser Pro Glu Leu Gln Arg Leu Ala Glu Met Asp Thr Pro Arg Arg Gly
        50                  55                  60 agg ggt ggc ttc caa agg att gtt cgc ctg gtg ggg gtc atc agg gac     240
Arg Gly Gly Phe Gln Arg Ile Val Arg Leu Val Gly Val Ile Arg Asp
65                  70                  75                  80 tgg gcc aac aag aat ttc cgt gaa gag gaa cca agg cct gac tcc ttc     288
Trp Ala Asn Lys Asn Phe Arg Glu Glu Glu Pro Arg Pro Asp Ser Phe
                85                  90                  95 cta gag cgt ttc cgt ggg cca gaa ctc cag act gtg aca acc cat cag     336
Leu Glu Arg Phe Arg Gly Pro Glu Leu Gln Thr Val Thr Thr His Gln
            100                 105                 110 ggg gat gac aaa ggc ggc aag gac ggc gag gga aag ggc acc aaa aag     384
Gly Asp Asp Lys Gly Gly Lys Asp Gly Glu Gly Lys Gly Thr Lys Lys
        115                 120                 125 aaa ttt gaa ctg ttt gtt ttg gac cca gcc gga gac tgg tat tac cgt     432
Lys Phe Glu Leu Phe Val Leu Asp Pro Ala Gly Asp Trp Tyr Tyr Arg
130                 135                 140 tgg ttg ttt gtc att gcc atg cct gtt ctt tac aac tgg tgc ctg ttg     480
Trp Leu Phe Val Ile Ala Met Pro Val Leu Tyr Asn Trp Cys Leu Leu
145                 150                 155                 160 gtg gcc aga gcc tgc ttc agt gat cta cag aga aac tat ttt gtg gta     528
Val Ala Arg Ala Cys Phe Ser Asp Leu Gln Arg Asn Tyr Phe Val Val
```

-continued

|  |  |
|---|---|
| tgg ctg gtg ctg gac tac ttc tca gac act gtc tat atc gca gac ctc<br>Trp Leu Val Leu Asp Tyr Phe Ser Asp Thr Val Tyr Ile Ala Asp Leu<br>                180                            185                              190 | 576 |
| atc att cgg ctg cgc aca ggc ttc cta gaa cag ggg ctc ttg gtc aaa<br>Ile Ile Arg Leu Arg Thr Gly Phe Leu Glu Gln Gly Leu Leu Val Lys<br>195                              200                            205 | 624 |
| gat ccc aag aaa ttg cga gac aac tat att cac act ttg cag ttc aaa<br>Asp Pro Lys Lys Leu Arg Asp Asn Tyr Ile His Thr Leu Gln Phe Lys<br>        210                            215                            220 | 672 |
| ttg gat gtg gct tct atc att ccc act gac ctt atc tat ttt gct gtg<br>Leu Asp Val Ala Ser Ile Ile Pro Thr Asp Leu Ile Tyr Phe Ala Val<br>225                              230                            235                            240 | 720 |
| ggt atc cac agc cct gag gta cgc ttc aac cgt cta tta cac ttt gcc<br>Gly Ile His Ser Pro Glu Val Arg Phe Asn Arg Leu Leu His Phe Ala<br>                      245                            250                            255 | 768 |
| cgt atg ttt gag ttc ttt gac cgc act gag aca cgc acc agc tac ccc<br>Arg Met Phe Glu Phe Phe Asp Arg Thr Glu Thr Arg Thr Ser Tyr Pro<br>                260                            265                            270 | 816 |
| aac atc ttc cga atc agc aat ctg gtc ctt tac atc ttg gtc atc atc<br>Asn Ile Phe Arg Ile Ser Asn Leu Val Leu Tyr Ile Leu Val Ile Ile<br>        275                            280                            285 | 864 |
| cac tgg aat gct tgt att tat tat gtt att tct aag tcc att ggc ttt<br>His Trp Asn Ala Cys Ile Tyr Tyr Val Ile Ser Lys Ser Ile Gly Phe<br>290                              295                            300 | 912 |
| gga gtt gac acc tgg gtt tac ccc aac att act gac cct gaa tat ggc<br>Gly Val Asp Thr Trp Val Tyr Pro Asn Ile Thr Asp Pro Glu Tyr Gly<br>305                              310                            315                            320 | 960 |
| tac ctg gct aga gag tac att tac tgt ctt tac tgg tcc aca ctg acc<br>Tyr Leu Ala Arg Glu Tyr Ile Tyr Cys Leu Tyr Trp Ser Thr Leu Thr<br>                      325                            330                            335 | 1008 |
| ctc acc acc att gga gag aca cca ccc cct gta aag gat gag gag tac<br>Leu Thr Thr Ile Gly Glu Thr Pro Pro Pro Val Lys Asp Glu Glu Tyr<br>                340                            345                            350 | 1056 |
| cta ttt gtc atc ttt gac ttc ttg att ggt gtc ctc atc ttt gcc act<br>Leu Phe Val Ile Phe Asp Phe Leu Ile Gly Val Leu Ile Phe Ala Thr<br>        355                            360                            365 | 1104 |
| att gtg gga aat gtg ggc tcc atg atc tcc aac atg aat gcc aca cga<br>Ile Val Gly Asn Val Gly Ser Met Ile Ser Asn Met Asn Ala Thr Arg<br>370                              375                            380 | 1152 |
| gca gag ttc cag gcc aag att gat gct gtc aaa cac tac atg cag ttc<br>Ala Glu Phe Gln Ala Lys Ile Asp Ala Val Lys His Tyr Met Gln Phe<br>385                              390                            395                            400 | 1200 |
| cga aag gtc agc aaa gac atg gaa gcc aag gtc atc aaa tgg ttt gac<br>Arg Lys Val Ser Lys Asp Met Glu Ala Lys Val Ile Lys Trp Phe Asp<br>                      405                            410                            415 | 1248 |
| tac ttg tgg acc aat aag aag aca gta gat gaa cga gaa gtc ctc aag<br>Tyr Leu Trp Thr Asn Lys Lys Thr Val Asp Glu Arg Glu Val Leu Lys<br>                420                            425                            430 | 1296 |
| aac ctg cca gca aag ctc agg gct gag ata gcc att aat gtt cac ttg<br>Asn Leu Pro Ala Lys Leu Arg Ala Glu Ile Ala Ile Asn Val His Leu<br>                      435                            440                            445 | 1344 |
| tcc act ctg aag aaa gtg cgc ata ttc cag gat tgg gaa gct ggc cta<br>Ser Thr Leu Lys Lys Val Arg Ile Phe Gln Asp Trp Glu Ala Gly Leu<br>450                              455                            460 | 1392 |
| ctg gtg gaa ctg gta ctg aag ctt cgt cct cag gtc ttt agt cct gga<br>Leu Val Glu Leu Val Leu Lys Leu Arg Pro Gln Val Phe Ser Pro Gly<br>465                              470                            475                            480 | 1440 |
| gat tat att tgc cgt aag ggg gac att ggc aag gaa atg tac atc atc | 1488 |

```
Asp Tyr Ile Cys Arg Lys Gly Asp Ile Gly Lys Glu Met Tyr Ile Ile
                485                 490                 495 aag gag ggc aag ttg gca gtg gta gct gat gat ggc gtg act cag tat     1536
Lys Glu Gly Lys Leu Ala Val Val Ala Asp Asp Gly Val Thr Gln Tyr
            500                 505                 510 gcc ttg ctc tca gct ggg agc tgc ttt ggt gag att agt atc ctt aac     1584
Ala Leu Leu Ser Ala Gly Ser Cys Phe Gly Glu Ile Ser Ile Leu Asn
        515                 520                 525 att aag ggt agc aaa atg ggc aat cga cgt act gct aat atc cgt agc     1632
Ile Lys Gly Ser Lys Met Gly Asn Arg Arg Thr Ala Asn Ile Arg Ser
    530                 535                 540 ctg ggc tac tca gat ctc ttc tgc ttg tcc aag gac gat ctt atg gaa     1680
Leu Gly Tyr Ser Asp Leu Phe Cys Leu Ser Lys Asp Asp Leu Met Glu
545                 550                 555                 560 gct gta act gag tat cct gat gcc aag aag gtc ctg gag gaa cgg ggt     1728
Ala Val Thr Glu Tyr Pro Asp Ala Lys Lys Val Leu Glu Glu Arg Gly
                565                 570                 575 agg gag atc ctg atg aag atg ggt cta ctg gat gag aat gaa gtg gca     1776
Arg Glu Ile Leu Met Lys Met Gly Leu Leu Asp Glu Asn Glu Val Ala
            580                 585                 590 gct agt atg gag gta gat gtt cag gag aag ctg gaa cag ttg gag aca     1824
Ala Ser Met Glu Val Asp Val Gln Glu Lys Leu Glu Gln Leu Glu Thr
        595                 600                 605 aac atg gat acc ttg tac act cgc ttt gcc cgc ctg ctg gct gag tac     1872
Asn Met Asp Thr Leu Tyr Thr Arg Phe Ala Arg Leu Leu Ala Glu Tyr
    610                 615                 620 act ggg gcc cag cag aag ctc aag caa cgc atc aca gtg cta gag acc     1920
Thr Gly Ala Gln Gln Lys Leu Lys Gln Arg Ile Thr Val Leu Glu Thr
625                 630                 635                 640 aag atg aaa cag aac cat gag gat gat tat cta tca gat ggg ata aac     1968
Lys Met Lys Gln Asn His Glu Asp Asp Tyr Leu Ser Asp Gly Ile Asn
                645                 650                 655 act cct gag cca act gct gct gaa taa                                 1995
Thr Pro Glu Pro Thr Ala Ala Glu
            660

<210> SEQ ID NO 6
<211> LENGTH: 664
<212> TYPE: PRT
<213> ORGANISM: Rattus norvegicus

<400> SEQUENCE: 6

Met Met Thr Glu Lys Ser Asn Gly Val Lys Ser Ser Pro Ala Asn Asn
1               5                   10                  15

His Asn His His Pro Pro Ser Ile Lys Ala Asn Gly Lys Asp Asp
            20                  25                  30

His Arg Ala Gly Ser Arg Pro Gln Ser Val Ala Ala Asp Asp Thr
        35                  40                  45

Ser Pro Glu Leu Gln Arg Leu Ala Glu Met Asp Thr Pro Arg Arg Gly
    50                  55                  60

Arg Gly Gly Phe Gln Arg Ile Val Arg Leu Val Gly Val Ile Arg Asp
65                  70                  75                  80

Trp Ala Asn Lys Asn Phe Arg Glu Glu Pro Arg Pro Asp Ser Phe
                85                  90                  95

Leu Glu Arg Phe Arg Gly Pro Glu Leu Gln Thr Val Thr Thr His Gln
            100                 105                 110

Gly Asp Asp Lys Gly Gly Lys Asp Gly Glu Gly Lys Gly Thr Lys Lys
        115                 120                 125
```

-continued

```
Lys Phe Glu Leu Phe Val Leu Asp Pro Ala Gly Asp Trp Tyr Tyr Arg
    130                 135                 140

Trp Leu Phe Val Ile Ala Met Pro Val Leu Tyr Asn Trp Cys Leu Leu
145                 150                 155                 160

Val Ala Arg Ala Cys Phe Ser Asp Leu Gln Arg Asn Tyr Phe Val Val
                165                 170                 175

Trp Leu Val Leu Asp Tyr Phe Ser Asp Thr Val Tyr Ile Ala Asp Leu
            180                 185                 190

Ile Ile Arg Leu Arg Thr Gly Phe Leu Glu Gln Gly Leu Leu Val Lys
        195                 200                 205

Asp Pro Lys Lys Leu Arg Asp Asn Tyr Ile His Thr Leu Gln Phe Lys
    210                 215                 220

Leu Asp Val Ala Ser Ile Ile Pro Thr Asp Leu Ile Tyr Phe Ala Val
225                 230                 235                 240

Gly Ile His Ser Pro Glu Val Arg Phe Asn Arg Leu Leu His Phe Ala
                245                 250                 255

Arg Met Phe Glu Phe Phe Asp Arg Thr Glu Thr Arg Thr Ser Tyr Pro
            260                 265                 270

Asn Ile Phe Arg Ile Ser Asn Leu Val Leu Tyr Ile Leu Val Ile Ile
        275                 280                 285

His Trp Asn Ala Cys Ile Tyr Tyr Val Ile Ser Lys Ser Ile Gly Phe
    290                 295                 300

Gly Val Asp Thr Trp Val Tyr Pro Asn Ile Thr Asp Pro Glu Tyr Gly
305                 310                 315                 320

Tyr Leu Ala Arg Glu Tyr Ile Tyr Cys Leu Tyr Trp Ser Thr Leu Thr
                325                 330                 335

Leu Thr Thr Ile Gly Glu Thr Pro Pro Pro Val Lys Asp Glu Glu Tyr
            340                 345                 350

Leu Phe Val Ile Phe Asp Phe Leu Ile Gly Val Leu Ile Phe Ala Thr
        355                 360                 365

Ile Val Gly Asn Val Gly Ser Met Ile Ser Asn Met Asn Ala Thr Arg
    370                 375                 380

Ala Glu Phe Gln Ala Lys Ile Asp Ala Val Lys His Tyr Met Gln Phe
385                 390                 395                 400

Arg Lys Val Ser Lys Asp Met Glu Ala Lys Val Ile Lys Trp Phe Asp
                405                 410                 415

Tyr Leu Trp Thr Asn Lys Lys Thr Val Asp Glu Arg Glu Val Leu Lys
            420                 425                 430

Asn Leu Pro Ala Lys Leu Arg Ala Glu Ile Ala Ile Asn Val His Leu
        435                 440                 445

Ser Thr Leu Lys Lys Val Arg Ile Phe Gln Asp Trp Glu Ala Gly Leu
    450                 455                 460

Leu Val Glu Leu Val Leu Lys Leu Arg Pro Gln Val Phe Ser Pro Gly
465                 470                 475                 480

Asp Tyr Ile Cys Arg Lys Gly Asp Ile Gly Lys Glu Met Tyr Ile Ile
                485                 490                 495

Lys Glu Gly Lys Leu Ala Val Val Ala Asp Asp Gly Val Thr Gln Tyr
            500                 505                 510

Ala Leu Leu Ser Ala Gly Ser Cys Phe Gly Glu Ile Ser Ile Leu Asn
        515                 520                 525

Ile Lys Gly Ser Lys Met Gly Asn Arg Arg Thr Ala Asn Ile Arg Ser
    530                 535                 540

Leu Gly Tyr Ser Asp Leu Phe Cys Leu Ser Lys Asp Asp Leu Met Glu
```

```
                 545                 550                 555                 560
Ala Val Thr Glu Tyr Pro Asp Ala Lys Lys Val Leu Glu Glu Arg Gly
                565                 570                 575

Arg Glu Ile Leu Met Lys Met Gly Leu Leu Asp Glu Asn Glu Val Ala
            580                 585                 590

Ala Ser Met Glu Val Asp Val Gln Glu Lys Leu Glu Gln Leu Glu Thr
            595                 600                 605

Asn Met Asp Thr Leu Tyr Thr Arg Phe Ala Arg Leu Leu Ala Glu Tyr
            610                 615                 620

Thr Gly Ala Gln Gln Lys Leu Lys Gln Arg Ile Thr Val Leu Glu Thr
625                 630                 635                 640

Lys Met Lys Gln Asn His Glu Asp Asp Tyr Leu Ser Asp Gly Ile Asn
                645                 650                 655

Thr Pro Glu Pro Thr Ala Ala Glu
                660

<210> SEQ ID NO 7
<211> LENGTH: 1995
<212> TYPE: DNA
<213> ORGANISM: Rattus norvegicus
<220> FEATURE:
<221> NAME/KEY: CDS
<222> LOCATION: (1)..(1992)
<223> OTHER INFORMATION:

<400> SEQUENCE: 7 atg atg acc gaa aaa tcc aat ggt gtg aaa agc tct cca gct aat aac      48
Met Met Thr Glu Lys Ser Asn Gly Val Lys Ser Ser Pro Ala Asn Asn
1               5                   10                  15 cat aac cat cat cct cct cct tct atc aag gcc aat ggc aaa gat gac      96
His Asn His His Pro Pro Pro Ser Ile Lys Ala Asn Gly Lys Asp Asp
            20                  25                  30 cac agg gca gga agc aga cca cag tct gtg gca gct gat gat gac act     144
His Arg Ala Gly Ser Arg Pro Gln Ser Val Ala Ala Asp Asp Asp Thr
        35                  40                  45 tct cca gaa cta caa agg ctg gca gag atg gat acc cct cgg agg ggg     192
Ser Pro Glu Leu Gln Arg Leu Ala Glu Met Asp Thr Pro Arg Arg Gly
    50                  55                  60 agg ggt ggc ttc caa agg att gtt cgc ctg gtg ggg gtc atc agg gac     240
Arg Gly Gly Phe Gln Arg Ile Val Arg Leu Val Gly Val Ile Arg Asp
65                  70                  75                  80 tgg gcc aac aag aat ttc cgt gaa gag gaa cca agg cct gac tcc ttc     288
Trp Ala Asn Lys Asn Phe Arg Glu Glu Glu Pro Arg Pro Asp Ser Phe
                85                  90                  95 cta gag cgt ttc cgt ggg cca gaa ctc cag act gtg aca acc cat cag     336
Leu Glu Arg Phe Arg Gly Pro Glu Leu Gln Thr Val Thr Thr His Gln
            100                 105                 110 ggg gat gac aaa ggc ggc aag gac ggc gag gga aag ggc acc aaa aag     384
Gly Asp Asp Lys Gly Gly Lys Asp Gly Glu Gly Lys Gly Thr Lys Lys
        115                 120                 125 aaa ttt gaa ctg ttt gtt ttg gac cca gcc gga gac tgg tat tac cgt     432
Lys Phe Glu Leu Phe Val Leu Asp Pro Ala Gly Asp Trp Tyr Tyr Arg
    130                 135                 140 tgg ttg ttt gtc att gcc atg cct gtt ctt tac aac tgg tgc ctg ttg     480
Trp Leu Phe Val Ile Ala Met Pro Val Leu Tyr Asn Trp Cys Leu Leu
145                 150                 155                 160 gtg gcc aga gcc tgc ttc agt gat cta cag aga aac tat ttt gtg gta     528
Val Ala Arg Ala Cys Phe Ser Asp Leu Gln Arg Asn Tyr Phe Val Val
                165                 170                 175
```

-continued

| | | |
|---|---|---|
| tgg ctg gtg ctg gac tac ttc tca gac act gtc tat atc gca gac ctc<br>Trp Leu Val Leu Asp Tyr Phe Ser Asp Thr Val Tyr Ile Ala Asp Leu<br>           180                    185                  190 | | 576 |
| atc att cgg ctg cgc aca ggc ttc cta gaa cag ggg ctc ttg gtc aaa<br>Ile Ile Arg Leu Arg Thr Gly Phe Leu Glu Gln Gly Leu Leu Val Lys<br>           195                    200 | | 624 |
| gat ccc aag aaa ttg cga gac aac tat att cac act ttg cag ttc aaa<br>Asp Pro Lys Lys Leu Arg Asp Asn Tyr Ile His Thr Leu Gln Phe Lys<br>210                    215                    220 | | 672 |
| ttg gat gtg gct tct atc att ccc act gac ctt atc tat ttt gct gtg<br>Leu Asp Val Ala Ser Ile Ile Pro Thr Asp Leu Ile Tyr Phe Ala Val<br>225                  230                235              240 | | 720 |
| ggt atc cac agc cct gag gta cgc ttc aac cgt cta tta cac ttt gcc<br>Gly Ile His Ser Pro Glu Val Arg Phe Asn Arg Leu Leu His Phe Ala<br>                 245                  250              255 | | 768 |
| cgt atg ttt gag ttc ttt gac cgc act gag aca cgc acc agc tac ccc<br>Arg Met Phe Glu Phe Phe Asp Arg Thr Glu Thr Arg Thr Ser Tyr Pro<br>           260                    265              270 | | 816 |
| aac atc ttc cga atc agc aat ctg gtc ctt tac atc ttg gtc atc atc<br>Asn Ile Phe Arg Ile Ser Asn Leu Val Leu Tyr Ile Leu Val Ile Ile<br>       275                    280                285 | | 864 |
| cac tgg aat gct tgt att tat tat gtt att tct aag tcc att ggc ttt<br>His Trp Asn Ala Cys Ile Tyr Tyr Val Ile Ser Lys Ser Ile Gly Phe<br>290                  295                300 | | 912 |
| gga gtt gac acc tgg gtt tac ccc aac att act gac cct gaa tat ggc<br>Gly Val Asp Thr Trp Val Tyr Pro Asn Ile Thr Asp Pro Glu Tyr Gly<br>305                  310                315              320 | | 960 |
| tac ctg gct aga gag tac att tac tgt ctt tac tgg tcc aca ctg acc<br>Tyr Leu Ala Arg Glu Tyr Ile Tyr Cys Leu Tyr Trp Ser Thr Leu Thr<br>                 325                  330              335 | | 1008 |
| ctc acc acc att gga gag aca cca ccc cct gta aag gat gag gag tac<br>Leu Thr Thr Ile Gly Glu Thr Pro Pro Pro Val Lys Asp Glu Glu Tyr<br>           340                    345              350 | | 1056 |
| cta ttt gtc atc ttt gac ttc ttg att ggt gtc ctc atc ttt gcc act<br>Leu Phe Val Ile Phe Asp Phe Leu Ile Gly Val Leu Ile Phe Ala Thr<br>       355                    360                365 | | 1104 |
| att gtg gga aat gtg ggc tcc atg atc tcc aac atg aat gcc aca cga<br>Ile Val Gly Asn Val Gly Ser Met Ile Ser Asn Met Asn Ala Thr Arg<br>370                  375                380 | | 1152 |
| gca gag ttc cag gcc aag att gat gct gtc aaa cac tac atg cag ttc<br>Ala Glu Phe Gln Ala Lys Ile Asp Ala Val Lys His Tyr Met Gln Phe<br>385                  390                395              400 | | 1200 |
| cga aag gtc agc aaa gac atg gaa gcc aag gtc atc aaa tgg ttt gac<br>Arg Lys Val Ser Lys Asp Met Glu Ala Lys Val Ile Lys Trp Phe Asp<br>                 405                  410              415 | | 1248 |
| tac ttg tgg acc aat aag aag aca gta gat gaa cga gaa gtc ctc aag<br>Tyr Leu Trp Thr Asn Lys Lys Thr Val Asp Glu Arg Glu Val Leu Lys<br>           420                    425              430 | | 1296 |
| aac ctg cca gca aag ctc agg gct gag ata gcc att aat gtt cac ttg<br>Asn Leu Pro Ala Lys Leu Arg Ala Glu Ile Ala Ile Asn Val His Leu<br>       435                    440              445 | | 1344 |
| tcc act ctg aag aaa gtg cgc ata ttc cag gat tgg gaa gct ggc cta<br>Ser Thr Leu Lys Lys Val Arg Ile Phe Gln Asp Trp Glu Ala Gly Leu<br>450                  455                460 | | 1392 |
| ctg gtg gaa ctg gta ctg aag ctt cgt cct cag gtc ttt agt cct gga<br>Leu Val Glu Leu Val Leu Lys Leu Arg Pro Gln Val Phe Ser Pro Gly<br>465                  470                475              480 | | 1440 |
| gat tat att tgc cgt aag ggg gac att ggc aag gaa atg tac atc atc<br>Asp Tyr Ile Cys Arg Lys Gly Asp Ile Gly Lys Glu Met Tyr Ile Ile<br>                 485                  490              495 | | 1488 |

```
aag gag ggc aag ttg gca gtg gta gct gat gat ggc gtg act cag tat    1536
Lys Glu Gly Lys Leu Ala Val Val Ala Asp Asp Gly Val Thr Gln Tyr
            500                 505                 510 gcc ttg ctc tca gct ggg agc tgc ttt ggt gag att agt atc ctt aac    1584
Ala Leu Leu Ser Ala Gly Ser Cys Phe Gly Glu Ile Ser Ile Leu Asn
        515                 520                 525 att aag ggt agc aaa atg ggc aat cga cgt act gct aat atc cgt agc    1632
Ile Lys Gly Ser Lys Met Gly Asn Arg Arg Thr Ala Asn Ile Arg Ser
    530                 535                 540 ctg ggc tac tca gat ctc ttc tgc ttg tcc aag gac gat ctt atg gaa    1680
Leu Gly Tyr Ser Asp Leu Phe Cys Leu Ser Lys Asp Asp Leu Met Glu
545                 550                 555                 560 gct gta act gag gct cct gat gcc aag aag gtc ctg gag gaa cgg ggt    1728
Ala Val Thr Glu Ala Pro Asp Ala Lys Lys Val Leu Glu Glu Arg Gly
                565                 570                 575 agg gag atc ctg atg aag atg ggt cta ctg gat gag aat gaa gtg gca    1776
Arg Glu Ile Leu Met Lys Met Gly Leu Leu Asp Glu Asn Glu Val Ala
            580                 585                 590 gct agt atg gag gta gat gtt cag gag aag ctg gaa cag ttg gag aca    1824
Ala Ser Met Glu Val Asp Val Gln Glu Lys Leu Glu Gln Leu Glu Thr
        595                 600                 605 aac atg gat acc ttg tac act cgc ttt gcc cgc ctg ctg gct gag tac    1872
Asn Met Asp Thr Leu Tyr Thr Arg Phe Ala Arg Leu Leu Ala Glu Tyr
    610                 615                 620 act ggg gcc cag cag aag ctc aag caa cgc atc aca gtg cta gag acc    1920
Thr Gly Ala Gln Gln Lys Leu Lys Gln Arg Ile Thr Val Leu Glu Thr
625                 630                 635                 640 aag atg aaa cag aac cat gag gat gat tat cta tca gat ggg ata aac    1968
Lys Met Lys Gln Asn His Glu Asp Asp Tyr Leu Ser Asp Gly Ile Asn
                645                 650                 655 act cct gag cca act gct gct gaa taa                                1995
Thr Pro Glu Pro Thr Ala Ala Glu
            660

<210> SEQ ID NO 8
<211> LENGTH: 664
<212> TYPE: PRT
<213> ORGANISM: Rattus norvegicus

<400> SEQUENCE: 8

Met Met Thr Glu Lys Ser Asn Gly Val Lys Ser Ser Pro Ala Asn Asn
1               5                   10                  15

His Asn His Pro Pro Ser Ile Lys Ala Asn Gly Lys Asp Asp
            20                  25                  30

His Arg Ala Gly Ser Arg Pro Gln Ser Val Ala Ala Asp Asp Thr
        35                  40                  45

Ser Pro Glu Leu Gln Arg Leu Ala Glu Met Asp Thr Pro Arg Arg Gly
    50                  55                  60

Arg Gly Gly Phe Gln Arg Ile Val Arg Leu Val Gly Val Ile Arg Asp
65                  70                  75                  80

Trp Ala Asn Lys Asn Phe Arg Glu Glu Pro Arg Pro Asp Ser Phe
                85                  90                  95

Leu Glu Arg Phe Arg Gly Pro Glu Leu Gln Thr Val Thr Thr His Gln
            100                 105                 110

Gly Asp Asp Lys Gly Gly Lys Asp Gly Glu Gly Lys Gly Thr Lys Lys
        115                 120                 125

Lys Phe Glu Leu Phe Val Leu Asp Pro Ala Gly Asp Trp Tyr Tyr Arg
    130                 135                 140
```

```
Trp Leu Phe Val Ile Ala Met Pro Val Leu Tyr Asn Trp Cys Leu Leu
145                 150                 155                 160

Val Ala Arg Ala Cys Phe Ser Asp Leu Gln Arg Asn Tyr Phe Val Val
                165                 170                 175

Trp Leu Val Leu Asp Tyr Phe Ser Asp Thr Val Tyr Ile Ala Asp Leu
            180                 185                 190

Ile Ile Arg Leu Arg Thr Gly Phe Leu Glu Gln Gly Leu Leu Val Lys
        195                 200                 205

Asp Pro Lys Lys Leu Arg Asp Asn Tyr Ile His Thr Leu Gln Phe Lys
210                 215                 220

Leu Asp Val Ala Ser Ile Ile Pro Thr Asp Leu Ile Tyr Phe Ala Val
225                 230                 235                 240

Gly Ile His Ser Pro Glu Val Arg Phe Asn Arg Leu Leu His Phe Ala
                245                 250                 255

Arg Met Phe Glu Phe Phe Asp Arg Thr Glu Thr Arg Thr Ser Tyr Pro
                260                 265                 270

Asn Ile Phe Arg Ile Ser Asn Leu Val Leu Tyr Ile Leu Val Ile Ile
            275                 280                 285

His Trp Asn Ala Cys Ile Tyr Tyr Val Ile Ser Lys Ser Ile Gly Phe
        290                 295                 300

Gly Val Asp Thr Trp Val Tyr Pro Asn Ile Thr Asp Pro Glu Tyr Gly
305                 310                 315                 320

Tyr Leu Ala Arg Glu Tyr Ile Tyr Cys Leu Tyr Trp Ser Thr Leu Thr
                325                 330                 335

Leu Thr Thr Ile Gly Glu Thr Pro Pro Pro Val Lys Asp Glu Glu Tyr
            340                 345                 350

Leu Phe Val Ile Phe Asp Phe Leu Ile Gly Val Leu Ile Phe Ala Thr
        355                 360                 365

Ile Val Gly Asn Val Gly Ser Met Ile Ser Asn Met Asn Ala Thr Arg
370                 375                 380

Ala Glu Phe Gln Ala Lys Ile Asp Ala Val Lys His Tyr Met Gln Phe
385                 390                 395                 400

Arg Lys Val Ser Lys Asp Met Glu Ala Lys Val Ile Lys Trp Phe Asp
                405                 410                 415

Tyr Leu Trp Thr Asn Lys Lys Thr Val Asp Glu Arg Glu Val Leu Lys
            420                 425                 430

Asn Leu Pro Ala Lys Leu Arg Ala Glu Ile Ala Ile Asn Val His Leu
        435                 440                 445

Ser Thr Leu Lys Lys Val Arg Ile Phe Gln Asp Trp Glu Ala Gly Leu
450                 455                 460

Leu Val Glu Leu Val Leu Lys Leu Arg Pro Gln Val Phe Ser Pro Gly
465                 470                 475                 480

Asp Tyr Ile Cys Arg Lys Gly Asp Ile Gly Lys Glu Met Tyr Ile Ile
                485                 490                 495

Lys Glu Gly Lys Leu Ala Val Val Ala Asp Asp Gly Val Thr Gln Tyr
            500                 505                 510

Ala Leu Leu Ser Ala Gly Ser Cys Phe Gly Glu Ile Ser Ile Leu Asn
        515                 520                 525

Ile Lys Gly Ser Lys Met Gly Asn Arg Arg Thr Ala Asn Ile Arg Ser
530                 535                 540

Leu Gly Tyr Ser Asp Leu Phe Cys Leu Ser Lys Asp Asp Leu Met Glu
545                 550                 555                 560
```

```
Ala Val Thr Glu Ala Pro Asp Ala Lys Lys Val Leu Glu Glu Arg Gly
                565                 570                 575

Arg Glu Ile Leu Met Lys Met Gly Leu Leu Asp Glu Asn Glu Val Ala
            580                 585                 590

Ala Ser Met Glu Val Asp Val Gln Glu Lys Leu Glu Gln Leu Glu Thr
        595                 600                 605

Asn Met Asp Thr Leu Tyr Thr Arg Phe Ala Arg Leu Leu Ala Glu Tyr
    610                 615                 620

Thr Gly Ala Gln Gln Lys Leu Lys Gln Arg Ile Thr Val Leu Glu Thr
625                 630                 635                 640

Lys Met Lys Gln Asn His Glu Asp Asp Tyr Leu Ser Asp Gly Ile Asn
                645                 650                 655

Thr Pro Glu Pro Thr Ala Ala Glu
                660

<210> SEQ ID NO 9
<211> LENGTH: 690
<212> TYPE: PRT
<213> ORGANISM: Homo sapiens
<220> FEATURE:
<221> NAME/KEY: MISC_FEATURE
<222> LOCATION: (1)..(690)
<223> OTHER INFORMATION: CNGA1

<400> SEQUENCE: 9

Met Lys Leu Ser Met Lys Asn Asn Ile Ile Asn Thr Gln Gln Ser Phe
1               5                   10                  15

Val Thr Met Pro Asn Val Ile Val Pro Asp Ile Glu Lys Glu Ile Arg
            20                  25                  30

Arg Met Glu Asn Gly Ala Cys Ser Ser Phe Ser Glu Asp Asp Asp Ser
        35                  40                  45

Ala Tyr Thr Ser Glu Glu Ser Glu Asn Glu Asn Pro His Ala Arg Gly
    50                  55                  60

Ser Phe Ser Tyr Lys Ser Leu Arg Lys Gly Gly Pro Ser Gln Arg Glu
65                  70                  75                  80

Gln Tyr Leu Pro Gly Ala Ile Ala Ile Phe Asn Val Asn Asn Ser Ser
                85                  90                  95

Asn Lys Asp Gln Glu Pro Glu Glu Lys Lys Lys Lys Lys Glu Lys
            100                 105                 110

Lys Ser Lys Ser Asp Asp Lys Asn Glu Asn Lys Asn Asp Pro Glu Lys
        115                 120                 125

Lys Lys Lys Lys Lys Asp Lys Glu Lys Lys Lys Glu Glu Lys Ser
    130                 135                 140

Lys Asp Lys Lys Glu His His Lys Lys Glu Val Val Ile Asp Pro
145                 150                 155                 160

Ser Gly Asn Thr Tyr Tyr Asn Trp Leu Phe Cys Ile Thr Leu Pro Val
                165                 170                 175

Met Tyr Asn Trp Thr Met Val Ile Ala Arg Ala Cys Phe Asp Glu Leu
            180                 185                 190

Gln Ser Asp Tyr Leu Glu Tyr Trp Leu Ile Leu Asp Tyr Val Ser Asp
        195                 200                 205

Ile Val Tyr Leu Ile Asp Met Phe Val Arg Thr Arg Thr Gly Tyr Leu
    210                 215                 220

Glu Gln Gly Leu Leu Val Lys Glu Glu Leu Lys Leu Ile Asn Lys Tyr
225                 230                 235                 240

Lys Ser Asn Leu Gln Phe Lys Leu Asp Val Leu Ser Leu Ile Pro Thr
```

-continued

```
                245                 250                 255
Asp Leu Leu Tyr Phe Lys Leu Gly Trp Asn Tyr Pro Glu Ile Arg Leu
                260                 265                 270
Asn Arg Leu Leu Arg Phe Ser Arg Met Phe Glu Phe Gln Arg Thr
            275                 280                 285
Glu Thr Arg Thr Asn Tyr Pro Asn Ile Phe Arg Ile Ser Asn Leu Val
        290                 295                 300
Met Tyr Ile Val Ile Ile His Trp Asn Ala Cys Val Phe Tyr Ser
305                 310                 315                 320
Ile Ser Lys Ala Ile Gly Phe Gly Asn Asp Thr Trp Val Tyr Pro Asp
                325                 330                 335
Ile Asn Asp Pro Glu Phe Gly Arg Leu Ala Arg Lys Tyr Val Tyr Ser
                340                 345                 350
Leu Tyr Trp Ser Thr Leu Thr Leu Thr Thr Ile Gly Glu Thr Pro Pro
            355                 360                 365
Pro Val Arg Asp Ser Glu Tyr Val Phe Val Val Asp Phe Leu Ile
        370                 375                 380
Gly Val Leu Ile Phe Ala Thr Ile Val Gly Asn Ile Gly Ser Met Ile
385                 390                 395                 400
Ser Asn Met Asn Ala Ala Arg Ala Glu Phe Gln Ala Arg Ile Asp Ala
                405                 410                 415
Ile Lys Gln Tyr Met His Phe Arg Asn Val Ser Lys Asp Met Glu Lys
                420                 425                 430
Arg Val Ile Lys Trp Phe Asp Tyr Leu Trp Thr Asn Lys Lys Thr Val
            435                 440                 445
Asp Glu Lys Glu Val Leu Lys Tyr Leu Pro Asp Lys Leu Arg Ala Glu
        450                 455                 460
Ile Ala Ile Asn Val His Leu Asp Thr Leu Lys Lys Val Arg Ile Phe
465                 470                 475                 480
Ala Asp Cys Glu Ala Gly Leu Leu Val Glu Leu Val Leu Lys Leu Gln
                485                 490                 495
Pro Gln Val Tyr Ser Pro Gly Asp Tyr Ile Cys Lys Lys Gly Asp Ile
            500                 505                 510
Gly Arg Glu Met Tyr Ile Ile Lys Glu Gly Lys Leu Ala Val Val Ala
            515                 520                 525
Asp Asp Gly Val Thr Gln Phe Val Val Leu Ser Asp Gly Ser Thr Phe
        530                 535                 540
Gly Glu Ile Ser Ile Leu Asn Ile Lys Gly Ser Lys Ala Gly Asn Arg
545                 550                 555                 560
Arg Thr Ala Asn Ile Lys Ser Ile Gly Tyr Ser Asp Leu Phe Cys Leu
                565                 570                 575
Ser Lys Asp Asp Leu Met Glu Ala Leu Thr Glu Tyr Pro Asp Ala Lys
            580                 585                 590
Thr Met Leu Glu Glu Lys Gly Lys Gln Ile Leu Met Lys Asp Gly Leu
            595                 600                 605
Leu Asp Leu Asn Ile Ala Asn Ala Gly Ser Asp Pro Lys Asp Leu Glu
        610                 615                 620
Glu Lys Val Thr Arg Met Glu Gly Ser Val Asp Leu Leu Gln Thr Arg
625                 630                 635                 640
Phe Ala Arg Ile Leu Ala Glu Tyr Glu Ser Met Gln Gln Lys Leu Lys
                645                 650                 655
Gln Arg Leu Thr Lys Val Glu Lys Phe Leu Lys Pro Leu Ile Asp Thr
            660                 665                 670
```

```
Glu Phe Ser Ser Ile Glu Gly Pro Trp Ser Glu Ser Gly Pro Ile Asp
        675                 680                 685

Ser Thr
    690

<210> SEQ ID NO 10
<211> LENGTH: 664
<212> TYPE: PRT
<213> ORGANISM: Homo sapiens
<220> FEATURE:
<221> NAME/KEY: MISC_FEATURE
<222> LOCATION: (1)..(664)
<223> OTHER INFORMATION: CNGA2

<400> SEQUENCE: 10

Met Thr Glu Lys Thr Asn Gly Val Lys Ser Ser Pro Ala Asn Asn His
1               5                   10                  15

Asn His His Ala Pro Pro Ala Ile Lys Ala Asn Gly Lys Asp Asp His
                20                  25                  30

Arg Thr Ser Ser Arg Pro His Ser Ala Ala Asp Asp Thr Ser Ser
            35                  40                  45

Glu Leu Gln Arg Leu Ala Asp Val Asp Ala Pro Gln Gln Gly Arg Ser
    50                  55                  60

Gly Phe Arg Arg Ile Val Arg Leu Val Gly Ile Ile Arg Glu Trp Ala
65                  70                  75                  80

Asn Lys Asn Phe Arg Glu Glu Pro Arg Pro Asp Ser Phe Leu Glu
                85                  90                  95

Arg Phe Arg Gly Pro Glu Leu Gln Thr Val Thr Thr Gln Glu Gly Asp
                100                 105                 110

Gly Lys Gly Asp Lys Asp Gly Glu Asp Lys Gly Thr Lys Lys Lys Phe
            115                 120                 125

Glu Leu Phe Val Leu Asp Pro Ala Gly Asp Trp Tyr Tyr Cys Trp Leu
    130                 135                 140

Phe Val Ile Ala Met Pro Val Leu Tyr Asn Trp Cys Leu Leu Val Ala
145                 150                 155                 160

Arg Ala Cys Phe Ser Asp Leu Gln Lys Gly Tyr Tyr Leu Val Trp Leu
                165                 170                 175

Val Leu Asp Tyr Val Ser Asp Val Val Tyr Ile Ala Asp Leu Phe Ile
                180                 185                 190

Arg Leu Arg Thr Gly Phe Leu Glu Gln Gly Leu Leu Val Lys Asp Thr
            195                 200                 205

Lys Lys Leu Arg Asp Asn Tyr Ile His Thr Leu Gln Phe Lys Leu Asp
    210                 215                 220

Val Ala Ser Ile Ile Pro Thr Asp Leu Ile Tyr Phe Ala Val Asp Ile
225                 230                 235                 240

His Ser Pro Glu Val Arg Phe Asn Arg Leu Leu His Phe Ala Arg Met
                245                 250                 255

Phe Glu Phe Phe Asp Arg Thr Glu Thr Arg Thr Asn Tyr Pro Asn Ile
                260                 265                 270

Phe Arg Ile Ser Asn Leu Val Leu Tyr Ile Leu Val Ile Ile His Trp
            275                 280                 285

Asn Ala Cys Ile Tyr Tyr Ala Ile Ser Lys Ser Ile Gly Phe Gly Val
    290                 295                 300

Asp Thr Trp Val Tyr Pro Asn Ile Thr Asp Pro Glu Tyr Gly Tyr Leu
305                 310                 315                 320
```

Ala Arg Glu Tyr Ile Tyr Cys Leu Tyr Trp Ser Thr Leu Thr Leu Thr
            325                 330                 335

Thr Ile Gly Glu Thr Pro Pro Val Lys Asp Glu Tyr Leu Phe
        340                 345                 350

Val Ile Phe Asp Phe Leu Ile Gly Val Leu Ile Phe Ala Thr Ile Val
            355                 360                 365

Gly Asn Val Gly Ser Met Ile Ser Asn Met Asn Ala Thr Arg Ala Glu
        370                 375                 380

Phe Gln Ala Lys Ile Asp Ala Val Lys His Tyr Met Gln Phe Arg Lys
385                 390                 395                 400

Val Ser Lys Gly Met Glu Ala Lys Val Ile Arg Trp Phe Asp Tyr Leu
                405                 410                 415

Trp Thr Asn Lys Lys Thr Val Asp Glu Arg Glu Ile Leu Lys Asn Leu
            420                 425                 430

Pro Ala Lys Leu Arg Ala Glu Ile Ala Ile Asn Val His Leu Ser Thr
        435                 440                 445

Leu Lys Lys Val Arg Ile Phe His Asp Cys Glu Ala Gly Leu Leu Val
450                 455                 460

Glu Leu Val Leu Lys Leu Arg Pro Gln Val Phe Ser Pro Gly Asp Tyr
465                 470                 475                 480

Ile Cys Arg Lys Gly Asp Ile Gly Lys Glu Met Tyr Ile Ile Lys Glu
                485                 490                 495

Gly Lys Leu Ala Val Val Ala Asp Asp Gly Val Thr Gln Tyr Ala Leu
            500                 505                 510

Leu Ser Ala Gly Ser Cys Phe Gly Glu Ile Ser Ile Leu Asn Ile Lys
        515                 520                 525

Gly Ser Lys Met Gly Asn Arg Arg Thr Ala Asn Ile Arg Ser Leu Gly
    530                 535                 540

Tyr Ser Asp Leu Phe Cys Leu Ser Lys Asp Asp Leu Met Glu Ala Val
545                 550                 555                 560

Thr Glu Tyr Pro Asp Ala Lys Lys Val Leu Glu Glu Arg Gly Arg Glu
                565                 570                 575

Ile Leu Met Lys Glu Gly Leu Leu Asp Glu Asn Glu Val Ala Thr Ser
            580                 585                 590

Met Glu Val Asp Val Gln Glu Lys Leu Gly Gln Leu Glu Thr Asn Met
        595                 600                 605

Glu Thr Leu Tyr Thr Arg Phe Gly Arg Leu Leu Ala Glu Tyr Thr Gly
    610                 615                 620

Ala Gln Gln Lys Leu Lys Gln Arg Ile Thr Val Leu Glu Thr Lys Met
625                 630                 635                 640

Lys Gln Asn Asn Glu Asp Asp Tyr Leu Ser Asp Gly Met Asn Ser Pro
                645                 650                 655

Glu Leu Ala Ala Ala Asp Glu Pro
            660

<210> SEQ ID NO 11
<211> LENGTH: 694
<212> TYPE: PRT
<213> ORGANISM: Homo sapiens
<220> FEATURE:
<221> NAME/KEY: MISC_FEATURE
<222> LOCATION: (1)..(694)
<223> OTHER INFORMATION: CNGA3

<400> SEQUENCE: 11

Met Ala Lys Ile Asn Thr Gln Tyr Ser His Pro Ser Arg Thr His Leu

-continued

```
1               5                   10                  15
Lys Val Lys Thr Ser Asp Arg Asp Leu Asn Arg Ala Glu Asn Gly Leu
            20                  25                  30

Ser Arg Ala His Ser Ser Glu Glu Thr Ser Ser Val Leu Gln Pro
            35                  40                  45

Gly Ile Ala Met Glu Thr Arg Gly Leu Ala Asp Ser Gly Gln Gly Ser
            50                  55                  60

Phe Thr Gly Gln Gly Ile Ala Arg Leu Ser Arg Leu Ile Phe Leu Leu
65                      70                  75                  80

Arg Arg Trp Ala Ala Arg His Val His His Gln Asp Gln Gly Pro Asp
                85                  90                  95

Ser Phe Pro Asp Arg Phe Arg Gly Ala Glu Leu Lys Glu Val Ser Ser
            100                 105                 110

Gln Glu Ser Asn Ala Gln Ala Asn Val Gly Ser Gln Glu Pro Ala Asp
            115                 120                 125

Arg Gly Arg Ser Ala Trp Pro Leu Ala Lys Cys Asn Thr Asn Thr Ser
            130                 135                 140

Asn Asn Thr Glu Glu Glu Lys Lys Thr Lys Lys Lys Asp Ala Ile Val
145                 150                 155                 160

Val Asp Pro Ser Asn Leu Tyr Tyr Arg Trp Leu Thr Ala Ile Ala
            165                 170                 175

Leu Pro Val Phe Tyr Asn Trp Tyr Leu Leu Ile Cys Arg Ala Cys Phe
            180                 185                 190

Asp Glu Leu Gln Ser Glu Tyr Leu Met Leu Trp Leu Val Leu Asp Tyr
            195                 200                 205

Ser Ala Asp Val Leu Tyr Val Leu Asp Val Leu Val Arg Ala Arg Thr
            210                 215                 220

Gly Phe Leu Glu Gln Gly Leu Met Val Ser Asp Thr Asn Arg Leu Trp
225                 230                 235                 240

Gln His Tyr Lys Thr Thr Thr Gln Phe Lys Leu Asp Val Leu Ser Leu
            245                 250                 255

Val Pro Thr Asp Leu Ala Tyr Leu Lys Val Gly Thr Asn Tyr Pro Glu
            260                 265                 270

Val Arg Phe Asn Arg Leu Leu Lys Phe Ser Arg Leu Phe Glu Phe Phe
            275                 280                 285

Asp Arg Thr Glu Thr Arg Thr Asn Tyr Pro Asn Met Phe Arg Ile Gly
            290                 295                 300

Asn Leu Val Leu Tyr Ile Leu Ile Ile His Trp Asn Ala Cys Ile
305                 310                 315                 320

Tyr Phe Ala Ile Ser Lys Phe Ile Gly Phe Gly Thr Asp Ser Trp Val
            325                 330                 335

Tyr Pro Asn Ile Ser Ile Pro Glu His Gly Arg Leu Ser Arg Lys Tyr
            340                 345                 350

Ile Tyr Ser Leu Tyr Trp Ser Thr Leu Thr Leu Thr Thr Ile Gly Glu
            355                 360                 365

Thr Pro Pro Pro Val Lys Asp Glu Glu Tyr Leu Phe Val Val Asp
            370                 375                 380

Phe Leu Val Gly Val Leu Ile Phe Ala Thr Ile Val Gly Asn Val Gly
385                 390                 395                 400

Ser Met Ile Ser Asn Met Asn Ala Ser Arg Ala Glu Phe Gln Ala Lys
            405                 410                 415

Ile Asp Ser Ile Lys Gln Tyr Met Gln Phe Arg Lys Val Thr Lys Asp
            420                 425                 430
```

Leu Glu Thr Arg Val Ile Arg Trp Phe Asp Tyr Leu Trp Ala Asn Lys
            435                 440                 445

Lys Thr Val Asp Glu Lys Glu Val Leu Lys Ser Leu Pro Asp Lys Leu
        450                 455                 460

Lys Ala Glu Ile Ala Ile Asn Val His Leu Asp Thr Leu Lys Lys Val
465                 470                 475                 480

Arg Ile Phe Gln Asp Cys Glu Ala Gly Leu Leu Val Glu Leu Val Leu
                485                 490                 495

Lys Leu Arg Pro Thr Val Phe Ser Pro Gly Asp Tyr Ile Cys Lys Lys
            500                 505                 510

Gly Asp Ile Gly Lys Glu Met Tyr Ile Ile Asn Glu Gly Lys Leu Ala
        515                 520                 525

Val Val Ala Asp Asp Gly Val Thr Gln Phe Val Val Leu Ser Asp Gly
530                 535                 540

Ser Tyr Phe Gly Glu Ile Ser Ile Leu Asn Ile Lys Gly Ser Lys Ser
545                 550                 555                 560

Gly Asn Arg Arg Thr Ala Asn Ile Arg Ser Ile Gly Tyr Ser Asp Leu
            565                 570                 575

Phe Cys Leu Ser Lys Asp Asp Leu Met Glu Ala Leu Thr Glu Tyr Pro
        580                 585                 590

Glu Ala Lys Lys Ala Leu Glu Glu Lys Gly Arg Gln Ile Leu Met Lys
    595                 600                 605

Asp Asn Leu Ile Asp Glu Glu Leu Ala Arg Ala Gly Ala Asp Pro Lys
610                 615                 620

Asp Leu Glu Glu Lys Val Glu Gln Leu Gly Ser Ser Leu Asp Thr Leu
625                 630                 635                 640

Gln Thr Arg Phe Ala Arg Leu Leu Ala Glu Tyr Asn Ala Thr Gln Met
            645                 650                 655

Lys Met Lys Gln Arg Leu Ser Gln Leu Glu Ser Gln Val Lys Gly Gly
        660                 665                 670

Gly Asp Lys Pro Leu Ala Asp Gly Glu Val Pro Gly Asp Ala Thr Lys
    675                 680                 685

Thr Glu Asp Lys Gln Gln
    690

<210> SEQ ID NO 12
<211> LENGTH: 1245
<212> TYPE: PRT
<213> ORGANISM: Homo sapiens
<220> FEATURE:
<221> NAME/KEY: MISC_FEATURE
<222> LOCATION: (1)..(1245)
<223> OTHER INFORMATION: CNGB1

<400> SEQUENCE: 12

Met Leu Gly Trp Val Gln Arg Val Leu Pro Gln Pro Gly Thr Pro
1               5                   10                  15

Arg Lys Thr Lys Met Gln Glu Glu Glu Val Glu Pro Glu Pro Glu
            20                  25                  30

Met Glu Ala Glu Val Glu Pro Glu Pro Asn Pro Glu Glu Ala Glu Thr
            35                  40                  45

Glu Ser Glu Ser Met Pro Pro Glu Glu Ser Phe Lys Glu Glu Val
        50                  55                  60

Ala Val Ala Asp Pro Ser Pro Gln Glu Thr Lys Glu Ala Ala Leu Thr
65                  70                  75                  80

-continued

```
Ser Thr Ile Ser Leu Arg Ala Gln Gly Ala Glu Ile Ser Glu Met Asn
                85                  90                  95
Ser Pro Ser His Arg Val Leu Thr Trp Leu Met Lys Gly Val Glu Lys
            100                 105                 110
Val Ile Pro Gln Pro Val His Ser Ile Thr Glu Asp Pro Ala Gln Ile
        115                 120                 125
Leu Gly His Gly Ser Thr Gly Asp Thr Gly Cys Thr Asp Glu Pro Asn
    130                 135                 140
Glu Ala Leu Glu Ala Gln Asp Thr Arg Pro Gly Leu Arg Leu Leu Leu
145                 150                 155                 160
Trp Leu Glu Gln Asn Leu Glu Arg Val Leu Pro Gln Pro Pro Lys Ser
                165                 170                 175
Ser Glu Val Trp Arg Asp Glu Pro Ala Val Ala Thr Ala Pro Pro Gly
            180                 185                 190
Arg Pro Gln Glu Met Gly Pro Lys Leu Gln Ala Arg Glu Thr Pro Ser
        195                 200                 205
Leu Pro Thr Pro Ile Pro Leu Gln Pro Lys Glu Glu Pro Lys Glu Ala
    210                 215                 220
Pro Ala Pro Glu Pro Gln Pro Gly Ser Gln Ala Gln Thr Ser Ser Leu
225                 230                 235                 240
Pro Pro Thr Arg Asp Pro Ala Arg Leu Val Ala Trp Val Leu His Arg
                245                 250                 255
Leu Glu Met Ala Leu Pro Gln Pro Val Leu His Gly Lys Ile Gly Glu
            260                 265                 270
Gln Glu Pro Asp Ser Pro Gly Ile Cys Asp Val Gln Thr Ile Ser Ile
        275                 280                 285
Leu Pro Gly Gly Gln Val Glu Pro Asp Leu Val Leu Glu Glu Val Glu
    290                 295                 300
Pro Pro Trp Glu Asp Ala His Gln Asp Val Ser Thr Ser Pro Gln Gly
305                 310                 315                 320
Thr Glu Val Val Pro Ala Tyr Glu Glu Glu Asn Lys Ala Val Glu Lys
                325                 330                 335
Met Pro Arg Glu Leu Ser Arg Ile Glu Glu Lys Glu Asp Glu Glu
            340                 345                 350
Glu Glu Glu Glu Glu Glu Glu Glu Glu Glu Glu Glu Glu Val Thr Glu
        355                 360                 365
Val Leu Leu Asp Ser Cys Val Val Ser Gln Val Gly Val Gly Gln Ser
    370                 375                 380
Glu Glu Asp Gly Thr Arg Pro Gln Ser Thr Ser Asp Gln Lys Leu Trp
385                 390                 395                 400
Glu Glu Val Gly Glu Glu Ala Lys Lys Glu Ala Glu Glu Lys Ala Lys
                405                 410                 415
Glu Glu Ala Glu Glu Val Ala Glu Glu Ala Glu Lys Glu Pro Gln
        420                     425                     430
Asp Trp Ala Glu Thr Lys Glu Glu Pro Glu Ala Glu Ala Glu Ala Ala
            435                 440                 445
Ser Ser Gly Val Pro Ala Thr Lys Gln His Pro Glu Val Gln Val Glu
    450                 455                 460
Asp Thr Asp Ala Asp Ser Cys Pro Leu Met Ala Glu Glu Asn Pro Pro
465                 470                 475                 480
Ser Thr Val Leu Pro Pro Ser Pro Ala Lys Ser Asp Thr Leu Ile
                485                 490                 495
Val Pro Ser Ser Ala Ser Gly Thr His Arg Lys Lys Leu Pro Ser Glu
```

-continued

```
                500             505             510
Asp Asp Glu Ala Glu Leu Lys Ala Leu Ser Pro Ala Glu Ser Pro
        515                 520                 525
Val Val Ala Trp Ser Asp Pro Thr Thr Pro Lys Asp Thr Asp Gly Gln
        530                 535                 540
Asp Arg Ala Ala Ser Thr Ala Ser Thr Asn Ser Ala Ile Ile Asn Asp
545                 550                 555                 560
Arg Leu Gln Glu Leu Val Lys Leu Phe Lys Glu Arg Thr Glu Lys Val
                565                 570                 575
Lys Glu Lys Leu Ile Asp Pro Asp Val Thr Ser Asp Glu Glu Ser Pro
            580                 585                 590
Lys Pro Ser Pro Ala Lys Lys Ala Pro Glu Pro Ala Pro Asp Thr Lys
            595                 600                 605
Pro Ala Glu Ala Glu Pro Val Glu Glu Glu His Tyr Cys Asp Met Leu
        610                 615                 620
Cys Cys Lys Phe Lys His Arg Pro Trp Lys Lys Tyr Gln Phe Pro Gln
625                 630                 635                 640
Ser Ile Asp Pro Leu Thr Asn Leu Met Tyr Val Leu Trp Leu Phe Phe
                645                 650                 655
Val Val Met Ala Trp Asn Trp Asn Cys Trp Leu Ile Pro Val Arg Trp
            660                 665                 670
Ala Phe Pro Tyr Gln Thr Pro Asp Asn Ile His His Trp Leu Leu Met
            675                 680                 685
Asp Tyr Leu Cys Asp Leu Ile Tyr Phe Leu Asp Ile Thr Val Phe Gln
        690                 695                 700
Thr Arg Leu Gln Phe Val Arg Gly Gly Asp Ile Ile Thr Asp Lys Lys
705                 710                 715                 720
Asp Met Arg Asn Asn Tyr Leu Lys Ser Arg Arg Phe Lys Met Asp Leu
                725                 730                 735
Leu Ser Leu Leu Pro Leu Asp Phe Leu Tyr Leu Lys Val Gly Val Asn
            740                 745                 750
Pro Leu Leu Arg Leu Pro Arg Cys Leu Lys Tyr Met Ala Phe Phe Glu
            755                 760                 765
Phe Asn Ser Arg Leu Glu Ser Ile Leu Ser Lys Ala Tyr Val Tyr Arg
        770                 775                 780
Val Ile Arg Thr Thr Ala Tyr Leu Leu Tyr Ser Leu His Leu Asn Ser
785                 790                 795                 800
Cys Leu Tyr Tyr Trp Ala Ser Ala Tyr Gln Gly Leu Gly Ser Thr His
                805                 810                 815
Trp Val Tyr Asp Gly Val Gly Asn Ser Tyr Ile Arg Cys Tyr Tyr Phe
            820                 825                 830
Ala Val Lys Thr Leu Ile Thr Ile Gly Gly Leu Pro Asp Pro Lys Thr
            835                 840                 845
Leu Phe Glu Ile Val Phe Gln Leu Leu Asn Tyr Phe Thr Gly Val Phe
        850                 855                 860
Ala Phe Ser Val Met Ile Gly Gln Met Arg Asp Val Val Gly Ala Ala
865                 870                 875                 880
Thr Ala Gly Gln Thr Tyr Tyr Arg Ser Cys Met Asp Ser Thr Val Lys
                885                 890                 895
Tyr Met Asn Phe Tyr Lys Ile Pro Lys Ser Val Gln Asn Arg Val Lys
            900                 905                 910
Thr Trp Tyr Glu Tyr Thr Trp His Ser Gln Gly Met Leu Asp Glu Ser
            915                 920                 925
```

```
Glu Leu Met Val Gln Leu Pro Asp Lys Met Arg Leu Asp Leu Ala Ile
    930                 935                 940

Asp Val Asn Tyr Asn Ile Val Ser Lys Val Ala Leu Phe Gln Gly Cys
945                 950                 955                 960

Asp Arg Gln Met Ile Phe Asp Met Leu Lys Arg Leu Arg Ser Val Val
            965                 970                 975

Tyr Leu Pro Asn Asp Tyr Val Cys Lys Lys Gly Glu Ile Gly Arg Glu
            980                 985                 990

Met Tyr Ile Ile Gln Ala Gly Gln  Val Gln Val Leu Gly  Gly Pro Asp
            995             1000                 1005

Gly Lys  Ser Val Leu Val Thr  Leu Lys Ala Gly Ser  Val Phe Gly
    1010                 1015                 1020

Glu Ile  Ser Leu Leu Ala Val  Gly Gly Gly Asn Arg  Arg Thr Ala
    1025                 1030                 1035

Asn Val  Val Ala His Gly Phe  Thr Asn Leu Phe Ile  Leu Asp Lys
    1040                 1045                 1050

Lys Asp  Leu Asn Glu Ile Leu  Val His Tyr Pro Glu  Ser Gln Lys
    1055                 1060                 1065

Leu Leu  Arg Lys Lys Ala Arg  Arg Met Leu Arg Ser  Asn Asn Lys
    1070                 1075                 1080

Pro Lys  Glu Glu Lys Ser Val  Leu Ile Leu Pro Pro  Arg Ala Gly
    1085                 1090                 1095

Thr Pro  Lys Leu Phe Asn Ala  Ala Leu Ala Met Thr  Gly Lys Met
    1100                 1105                 1110

Gly Gly  Lys Gly Ala Lys Gly  Gly Lys Leu Ala His  Leu Arg Ala
    1115                 1120                 1125

Arg Leu  Lys Glu Leu Ala Ala  Leu Glu Ala Ala Ala  Lys Gln Gln
    1130                 1135                 1140

Glu Leu  Val Glu Gln Ala Lys  Ser Ser Gln Asp Val  Lys Gly Glu
    1145                 1150                 1155

Glu Gly  Ser Ala Ala Pro Asp  Gln His Thr His Pro  Lys Glu Ala
    1160                 1165                 1170

Ala Thr  Asp Pro Pro Ala Pro  Arg Thr Pro Glu Pro  Pro Pro Gly
    1175                 1180                 1185

Ser Pro  Pro Ser Ser Pro Pro  Pro Ala Ser Leu Gly  Arg Pro Glu
    1190                 1195                 1200

Gly Glu  Glu Glu Gly Pro Ala  Glu Pro Glu His Ser  Val Arg
    1205                 1210                 1215

Ile Cys  Met Ser Pro Gly Pro  Glu Pro Gly Glu Gln  Ile Leu Ser
    1220                 1225                 1230

Val Lys  Met Pro Glu Glu Arg  Glu Glu Lys Ala Glu
    1235                 1240                 1245

<210> SEQ ID NO 13
<211> LENGTH: 575
<212> TYPE: PRT
<213> ORGANISM: Homo sapiens
<220> FEATURE:
<221> NAME/KEY: MISC_FEATURE
<222> LOCATION: (1)..(575)
<223> OTHER INFORMATION: CNGB2

<400> SEQUENCE: 13

Met Ser Gln Asp Thr Lys Val Lys Thr Thr Glu Ser Ser Pro Pro Ala
1               5                   10                  15
```

Pro Ser Lys Ala Arg Lys Leu Leu Pro Val Leu Asp Pro Ser Gly Asp
            20                  25                  30

Tyr Tyr Tyr Trp Trp Leu Asn Thr Met Val Phe Pro Val Met Tyr Asn
        35                  40                  45

Leu Ile Ile Leu Val Cys Arg Ala Cys Phe Pro Asp Leu Gln His Gly
    50                  55                  60

Tyr Leu Val Ala Trp Leu Val Leu Asp Tyr Thr Ser Asp Leu Leu Tyr
65                  70                  75                  80

Leu Leu Asp Met Val Val Arg Phe His Thr Gly Phe Leu Glu Gln Gly
                85                  90                  95

Ile Leu Val Val Asp Lys Gly Arg Ile Ser Ser Arg Tyr Val Arg Thr
                100                 105                 110

Trp Ser Phe Phe Leu Asp Leu Ala Ser Leu Met Pro Thr Asp Val Val
            115                 120                 125

Tyr Val Arg Leu Gly Pro His Thr Pro Thr Leu Arg Leu Asn Arg Phe
        130                 135                 140

Leu Arg Ala Pro Arg Leu Phe Glu Ala Phe Asp Arg Thr Glu Thr Arg
145                 150                 155                 160

Thr Ala Tyr Pro Asn Ala Phe Arg Ile Ala Lys Leu Met Leu Tyr Ile
                165                 170                 175

Phe Val Val Ile His Trp Asn Ser Cys Leu Tyr Phe Ala Leu Ser Arg
            180                 185                 190

Tyr Leu Gly Phe Gly Arg Asp Ala Trp Val Tyr Pro Asp Pro Ala Gln
        195                 200                 205

Pro Gly Phe Glu Arg Leu Arg Arg Gln Tyr Leu Tyr Ser Phe Tyr Phe
    210                 215                 220

Ser Thr Leu Ile Leu Thr Thr Val Gly Asp Thr Pro Pro Pro Ala Arg
225                 230                 235                 240

Glu Glu Glu Tyr Leu Phe Met Val Gly Asp Phe Leu Leu Ala Val Met
                245                 250                 255

Gly Phe Ala Thr Ile Met Gly Ser Met Ser Ser Val Ile Tyr Asn Met
                260                 265                 270

Asn Thr Ala Asp Ala Ala Phe Tyr Pro Asp His Ala Leu Val Lys Lys
            275                 280                 285

Tyr Met Lys Leu Gln His Val Asn Arg Lys Leu Glu Arg Arg Val Ile
        290                 295                 300

Asp Trp Tyr Gln His Leu Gln Ile Asn Lys Lys Met Thr Asn Glu Val
305                 310                 315                 320

Ala Ile Leu Gln His Leu Pro Glu Arg Leu Arg Ala Glu Val Ala Val
                325                 330                 335

Ser Val His Leu Ser Thr Leu Ser Arg Val Gln Ile Phe Gln Asn Cys
                340                 345                 350

Glu Ala Ser Leu Leu Glu Glu Leu Val Leu Lys Leu Gln Pro Gln Thr
            355                 360                 365

Tyr Ser Pro Gly Glu Tyr Val Cys Arg Lys Gly Asp Ile Gly Gln Glu
        370                 375                 380

Met Tyr Ile Ile Arg Glu Gly Gln Leu Ala Val Val Ala Asp Asp Gly
385                 390                 395                 400

Ile Thr Gln Tyr Ala Val Leu Gly Ala Gly Leu Tyr Phe Gly Glu Ile
                405                 410                 415

Ser Ile Ile Asn Ile Lys Gly Asn Met Ser Gly Asn Arg Arg Thr Ala
                420                 425                 430

Asn Ile Lys Ser Leu Gly Tyr Ser Asp Leu Phe Cys Leu Ser Lys Glu

```
                435                 440                 445
Asp Leu Arg Glu Val Leu Ser Glu Tyr Pro Gln Ala Gln Thr Ile Met
    450                 455                 460

Glu Glu Lys Gly Arg Glu Ile Leu Leu Lys Met Asn Lys Leu Asp Val
465                 470                 475                 480

Asn Ala Glu Ala Ala Glu Ile Ala Leu Gln Glu Ala Thr Glu Ser Arg
                485                 490                 495

Leu Arg Gly Leu Asp Gln Gln Leu Asp Asp Leu Gln Thr Lys Phe Ala
            500                 505                 510

Arg Leu Leu Ala Glu Leu Glu Ser Ser Ala Leu Lys Ile Ala Tyr Arg
        515                 520                 525

Ile Glu Arg Leu Glu Trp Gln Thr Arg Glu Trp Pro Met Pro Glu Asp
    530                 535                 540

Leu Ala Glu Ala Asp Asp Glu Gly Glu Pro Glu Gly Thr Ser Lys
545                 550                 555                 560

Asp Glu Glu Gly Arg Ala Ser Gln Glu Gly Pro Pro Gly Pro Glu
                565                 570                 575

<210> SEQ ID NO 14
<211> LENGTH: 615
<212> TYPE: PRT
<213> ORGANISM: Homo sapiens
<220> FEATURE:
<221> NAME/KEY: MISC_FEATURE
<222> LOCATION: (1)..(615)
<223> OTHER INFORMATION: CNGB3

<400> SEQUENCE: 14

Met Pro Leu Thr Glu Tyr Leu Lys Arg Ile Lys Leu Pro Asn Ser Ile
1               5                   10                  15

Asp Ser Tyr Thr Asp Arg Leu Tyr Leu Leu Trp Leu Leu Leu Val Thr
            20                  25                  30

Leu Ala Tyr Asn Trp Asn Cys Trp Phe Ile Pro Leu Arg Leu Val Phe
        35                  40                  45

Pro Tyr Gln Thr Ala Asp Asn Ile His Tyr Trp Leu Ile Ala Asp Ile
    50                  55                  60

Ile Cys Asp Ile Ile Tyr Leu Tyr Asp Met Leu Phe Ile Gln Pro Arg
65                  70                  75                  80

Leu Gln Phe Val Arg Gly Gly Asp Ile Ile Val Asp Ser Asn Glu Leu
                85                  90                  95

Arg Lys His Tyr Arg Thr Ser Thr Lys Phe Gln Leu Asp Val Ala Ser
            100                 105                 110

Ile Ile Pro Phe Asp Ile Cys Tyr Leu Phe Phe Gly Phe Asn Pro Met
        115                 120                 125

Phe Arg Ala Asn Arg Met Leu Lys Tyr Thr Ser Phe Phe Glu Phe Asn
    130                 135                 140

His His Leu Glu Ser Ile Met Asp Lys Ala Tyr Ile Tyr Arg Val Ile
145                 150                 155                 160

Arg Thr Thr Gly Tyr Leu Leu Phe Ile Leu His Ile Asn Ala Cys Val
                165                 170                 175

Tyr Tyr Trp Ala Ser Asn Tyr Glu Gly Ile Gly Thr Thr Arg Trp Val
            180                 185                 190

Tyr Asp Gly Glu Gly Asn Glu Tyr Leu Arg Cys Tyr Tyr Trp Ala Val
        195                 200                 205

Arg Thr Leu Ile Thr Ile Gly Gly Leu Pro Glu Pro Gln Thr Leu Phe
    210                 215                 220
```

-continued

```
Glu Ile Val Phe Gln Leu Leu Asn Phe Phe Ser Gly Val Phe Val Phe
225                 230                 235                 240

Ser Ser Leu Ile Gly Gln Met Arg Asp Val Ile Gly Ala Ala Thr Ala
            245                 250                 255

Asn Gln Asn Tyr Phe Arg Ala Cys Met Asp Asp Thr Ile Ala Tyr Met
                260                 265                 270

Asn Asn Tyr Ser Ile Pro Lys Leu Val Gln Lys Arg Val Arg Thr Trp
        275                 280                 285

Tyr Glu Tyr Thr Trp Asp Ser Gln Arg Met Leu Asp Glu Ser Asp Leu
290                 295                 300

Leu Lys Thr Leu Pro Thr Thr Val Gln Leu Ala Leu Ala Ile Asp Val
305                 310                 315                 320

Asn Phe Ser Ile Ile Ser Lys Val Asp Leu Phe Lys Gly Cys Asp Thr
                325                 330                 335

Gln Met Ile Tyr Asp Met Leu Leu Arg Leu Lys Ser Val Leu Tyr Leu
                340                 345                 350

Pro Gly Asp Phe Val Cys Lys Lys Gly Glu Ile Gly Lys Glu Met Tyr
            355                 360                 365

Ile Ile Lys His Gly Glu Val Gln Val Leu Gly Gly Pro Asp Gly Thr
370                 375                 380

Lys Val Leu Val Thr Leu Lys Ala Gly Ser Val Phe Gly Glu Ile Ser
385                 390                 395                 400

Leu Leu Ala Ala Gly Gly Gly Asn Arg Arg Thr Ala Asn Val Val Ala
                405                 410                 415

His Gly Phe Ala Asn Leu Leu Thr Leu Asp Lys Lys Thr Leu Gln Glu
                420                 425                 430

Ile Leu Val His Tyr Pro Asp Ser Glu Arg Ile Leu Met Lys Lys Ala
            435                 440                 445

Arg Val Leu Leu Lys Gln Lys Ala Lys Thr Ala Glu Ala Thr Pro Pro
450                 455                 460

Arg Lys Asp Leu Ala Leu Leu Phe Pro Pro Lys Glu Glu Thr Pro Lys
465                 470                 475                 480

Leu Phe Lys Thr Leu Leu Gly Gly Thr Gly Lys Ala Ser Leu Ala Arg
                485                 490                 495

Leu Leu Lys Leu Lys Arg Glu Gln Ala Ala Gln Lys Lys Glu Asn Ser
            500                 505                 510

Glu Gly Gly Glu Glu Glu Gly Lys Glu Asn Glu Asp Lys Gln Lys Glu
            515                 520                 525

Asn Glu Asp Lys Gln Lys Glu Asn Glu Asp Lys Gly Lys Glu Asn Glu
530                 535                 540

Asp Lys Asp Lys Gly Arg Glu Pro Glu Glu Lys Pro Leu Asp Arg Pro
545                 550                 555                 560

Glu Cys Thr Ala Ser Pro Ile Ala Val Glu Glu Pro His Ser Val
                565                 570                 575

Arg Arg Thr Val Leu Pro Arg Gly Thr Ser Arg Gln Ser Leu Ile Ile
            580                 585                 590

Ser Met Ala Pro Ser Ala Glu Gly Gly Glu Glu Val Leu Thr Ile Glu
                595                 600                 605

Val Lys Glu Lys Ala Lys Gln
610                 615

<210> SEQ ID NO 15
<211> LENGTH: 664
```

```
<212> TYPE: PRT
<213> ORGANISM: Mus musculus
<220> FEATURE:
<221> NAME/KEY: MISC_FEATURE
<222> LOCATION: (1)..(664)
<223> OTHER INFORMATION: CNGA2

<400> SEQUENCE: 15
```

Met Met Thr Glu Lys Ser Asn Gly Val Lys Ser Pro Ala Asn Asn
1               5                   10                  15

His Asn His His Pro Pro Ser Ile Lys Ala Asn Gly Lys Asp Asp
            20                  25                  30

His Arg Ala Gly Ser Arg Pro Gln Ser Val Ala Ala Asp Asp Thr
            35                  40                  45

Ser Ser Glu Leu Gln Arg Leu Ala Glu Met Asp Thr Pro Arg Arg Gly
50                      55                  60

Arg Gly Gly Phe Arg Arg Ile Val Arg Leu Val Gly Ile Ile Arg Asp
65                  70                  75                  80

Trp Ala Asn Lys Asn Phe Arg Glu Glu Pro Arg Pro Asp Ser Phe
                85                  90                  95

Leu Glu Arg Phe Arg Gly Pro Glu Leu Gln Thr Val Thr Pro His Gln
                100                 105                 110

Gly Asp Gly Lys Gly Asp Lys Asp Gly Glu Gly Lys Gly Thr Lys Lys
            115                 120                 125

Lys Phe Glu Leu Phe Val Leu Asp Pro Ala Gly Asp Trp Tyr Tyr Arg
130                 135                 140

Trp Leu Phe Val Ile Ala Met Pro Val Leu Tyr Asn Trp Cys Leu Leu
145                 150                 155                 160

Val Ala Arg Ala Cys Phe Ser Asp Leu Gln Arg Asn Tyr Phe Val Val
                165                 170                 175

Trp Leu Val Leu Asp Tyr Phe Ser Asp Thr Val Tyr Ile Ala Asp Leu
                180                 185                 190

Ile Ile Arg Leu Arg Thr Gly Phe Leu Glu Gln Gly Leu Leu Val Lys
            195                 200                 205

Asp Pro Lys Lys Leu Arg Asp Asn Tyr Ile His Thr Leu Gln Phe Lys
210                 215                 220

Leu Asp Val Ala Ser Ile Ile Pro Thr Asp Leu Ile Tyr Phe Ala Val
225                 230                 235                 240

Gly Ile His Ser Pro Glu Val Arg Phe Asn Arg Leu Leu His Phe Ala
                245                 250                 255

Arg Met Phe Glu Phe Phe Asp Arg Thr Glu Thr Arg Thr Ser Tyr Pro
                260                 265                 270

Asn Ile Phe Arg Ile Ser Asn Leu Val Leu Tyr Ile Leu Val Ile Ile
            275                 280                 285

His Trp Asn Ala Cys Ile Tyr Tyr Ala Ile Ser Lys Ser Ile Gly Phe
        290                 295                 300

Gly Val Asp Thr Trp Val Tyr Pro Asn Ile Thr Asp Pro Glu Tyr Gly
305                 310                 315                 320

Tyr Leu Ala Arg Glu Tyr Ile Tyr Cys Leu Tyr Trp Ser Thr Leu Thr
                325                 330                 335

Leu Thr Thr Ile Gly Glu Thr Pro Pro Pro Val Lys Asp Glu Glu Tyr
            340                 345                 350

Leu Phe Phe Ile Phe Asp Phe Leu Ile Gly Val Leu Ile Phe Ala Thr
            355                 360                 365

Ile Val Gly Asn Val Gly Ser Met Ile Ser Asn Met Asn Ala Thr Arg

```
                370             375             380
Ala Glu Phe Gln Ala Lys Ile Asp Ala Lys His Tyr Met Gln Phe
385                 390                 395                 400

Arg Lys Val Ser Lys Asp Met Glu Ala Lys Val Ile Lys Trp Phe Asp
                405                 410                 415

Tyr Leu Trp Thr Asn Lys Lys Thr Val Asp Glu Arg Glu Val Leu Lys
                420                 425                 430

Asn Leu Pro Ala Lys Leu Arg Ala Glu Ile Ala Ile Asn Val His Leu
                435                 440                 445

Ser Thr Leu Lys Lys Val Arg Ile Phe Gln Asp Cys Glu Ala Gly Leu
        450                 455                 460

Leu Val Glu Leu Val Leu Lys Leu Arg Pro Gln Val Phe Ser Pro Gly
465                 470                 475                 480

Asp Tyr Ile Cys Arg Lys Gly Asp Ile Gly Lys Glu Met Tyr Ile Ile
                485                 490                 495

Lys Glu Gly Lys Leu Ala Val Val Ala Asp Asp Gly Val Thr Gln Tyr
                500                 505                 510

Ala Leu Leu Ser Ala Gly Ser Cys Phe Gly Glu Ile Ser Ile Leu Asn
        515                 520                 525

Ile Lys Gly Ser Lys Met Gly Asn Arg Arg Thr Gly Thr Ile Arg Ser
        530                 535                 540

Leu Gly Tyr Ser Asp Leu Phe Cys Leu Ser Lys Asp Asp Leu Met Glu
545                 550                 555                 560

Ala Val Thr Glu Tyr Pro Asp Ala Lys Lys Val Leu Glu Glu Arg Gly
                565                 570                 575

Arg Glu Ile Leu Met Lys Glu Gly Leu Leu Asp Glu Asn Glu Val Ala
                580                 585                 590

Ala Ser Met Glu Val Asp Val Gln Glu Lys Leu Glu Gln Leu Glu Thr
        595                 600                 605

Asn Met Glu Thr Leu Tyr Thr Arg Phe Ala Arg Leu Leu Ala Glu Tyr
610                 615                 620

Thr Gly Ala Gln Gln Lys Leu Lys Gln Arg Ile Thr Val Leu Glu Thr
625                 630                 635                 640

Lys Met Lys Gln Asn His Glu Asp Asp Tyr Leu Ser Asp Gly Ile Asn
                645                 650                 655

Thr Pro Glu Pro Ala Val Ala Glu
            660

<210> SEQ ID NO 16
<211> LENGTH: 732
<212> TYPE: PRT
<213> ORGANISM: Oryctolagus cuniculus
<220> FEATURE:
<221> NAME/KEY: MISC_FEATURE
<222> LOCATION: (1)..(732)
<223> OTHER INFORMATION: CNGA2

<400> SEQUENCE: 16

Met Ser Ser Trp Arg Ser Cys Ala Arg Ala Pro Leu Ser Gly Ser Ala
1               5                   10                  15

Trp Arg Arg Ser Ala Ala Thr Arg Arg Ser Arg Arg Cys Leu Lys Thr
                20                  25                  30

Lys Arg Lys Arg Trp Ser Ser Gly Lys Gly Thr Pro Met Gln Ser Thr
            35                  40                  45

Gln Cys Glu Thr Arg Arg Arg Ala Gln Thr Pro Cys Glu Ser Thr Gly
        50                  55                  60
```

-continued

```
His Thr Trp Arg Met Thr Glu Lys Ser Asn Gly Val Lys Ser Ser Pro
 65                  70                  75                  80

Ala Asn Asn His Asn Asn His Val Pro Ala Thr Ile Lys Ala Asn Gly
                 85                  90                  95

Lys Asp Glu Ser Arg Thr Arg Ser Arg Pro Gln Ser Ala Ala Asp Asp
            100                 105                 110

Asp Thr Ser Ser Glu Leu Gln Arg Leu Ala Glu Met Asp Ala Pro Gln
        115                 120                 125

Gln Arg Arg Gly Gly Phe Arg Arg Ile Val Arg Leu Val Gly Val Ile
    130                 135                 140

Arg Gln Trp Ala Asn Arg Asn Phe Arg Glu Glu Ala Arg Pro Asp
145                 150                 155                 160

Ser Phe Leu Glu Arg Phe Arg Gly Pro Glu Leu Gln Thr Val Thr Thr
                165                 170                 175

Gln Gln Gly Asp Gly Lys Gly Lys Asp Gly Asp Gly Lys Gly Thr
            180                 185                 190

Lys Lys Lys Phe Glu Leu Phe Val Leu Asp Pro Ala Gly Asp Trp Tyr
        195                 200                 205

Tyr Arg Trp Leu Phe Val Ile Ala Met Pro Val Leu Tyr Asn Trp Cys
    210                 215                 220

Leu Leu Val Ala Arg Ala Cys Phe Ser Asp Leu Gln Arg Gly Tyr Phe
225                 230                 235                 240

Leu Val Trp Leu Val Leu Asp Tyr Phe Ser Asp Val Val Tyr Ile Ala
                245                 250                 255

Asp Leu Phe Ile Arg Leu Arg Thr Gly Phe Leu Glu Gln Gly Leu Leu
            260                 265                 270

Val Lys Asp Pro Lys Lys Leu Arg Asp Asn Tyr Ile His Thr Leu Gln
        275                 280                 285

Phe Lys Leu Asp Val Ala Ser Ile Ile Pro Thr Asp Leu Ile Tyr Phe
    290                 295                 300

Ala Val Gly Ile His Asn Pro Glu Leu Arg Phe Asn Arg Leu Leu His
305                 310                 315                 320

Phe Ala Arg Met Phe Glu Phe Phe Asp Arg Thr Glu Thr Arg Thr Ser
                325                 330                 335

Tyr Pro Asn Ile Phe Arg Ile Ser Asn Leu Val Leu Tyr Ile Leu Val
            340                 345                 350

Ile Ile His Trp Asn Ala Cys Ile Tyr Tyr Ala Ile Ser Lys Ser Ile
        355                 360                 365

Gly Phe Gly Val Asp Thr Trp Val Tyr Pro Asn Ile Thr Asp Pro Glu
    370                 375                 380

Tyr Gly Tyr Leu Ala Arg Glu Tyr Ile Tyr Cys Leu Tyr Trp Ser Thr
385                 390                 395                 400

Leu Thr Leu Thr Thr Ile Gly Glu Thr Pro Pro Val Lys Asp Glu
                405                 410                 415

Glu Tyr Leu Phe Val Ile Phe Asp Phe Leu Ile Gly Val Leu Ile Phe
            420                 425                 430

Ala Thr Ile Val Gly Asn Val Gly Ser Met Ile Ser Asn Met Asn Ala
        435                 440                 445

Thr Arg Ala Glu Phe Gln Ala Lys Ile Asp Ala Val Lys His Tyr Met
    450                 455                 460

Gln Phe Arg Lys Val Ser Lys Glu Met Glu Ala Lys Val Ile Lys Trp
465                 470                 475                 480
```

```
Phe Asp Tyr Leu Trp Thr Asn Lys Lys Thr Val Asp Arg Glu Val
                485                 490                 495

Leu Lys Asn Leu Pro Ala Lys Leu Arg Ala Glu Ile Ala Ile Asn Val
            500                 505                 510

His Leu Ser Thr Leu Lys Lys Val Arg Ile Phe Gln Asp Cys Glu Ala
            515                 520                 525

Gly Leu Leu Val Glu Leu Val Leu Lys Leu Arg Pro Gln Val Phe Ser
            530                 535                 540

Pro Gly Asp Tyr Ile Cys Arg Lys Gly Asp Ile Gly Lys Glu Met Tyr
545                 550                 555                 560

Ile Ile Lys Glu Gly Lys Leu Ala Val Val Ala Asp Asp Gly Val Thr
                565                 570                 575

Gln Tyr Ala Leu Leu Ser Ala Gly Ser Cys Phe Gly Glu Ile Ser Ile
            580                 585                 590

Leu Asn Ile Lys Gly Ser Lys Met Gly Asn Arg Arg Thr Ala Asn Ile
            595                 600                 605

Arg Ser Leu Gly Tyr Ser Asp Leu Phe Cys Leu Ser Lys Asp Asp Leu
            610                 615                 620

Met Glu Ala Val Thr Glu Tyr Pro Asp Ala Lys Lys Val Leu Glu Glu
625                 630                 635                 640

Arg Gly Arg Glu Ile Leu Met Lys Glu Gly Leu Leu Asp Glu Asn Glu
                645                 650                 655

Val Ala Ala Ser Met Glu Val Asp Val Gln Glu Lys Leu Lys Gln Leu
            660                 665                 670

Glu Thr Asn Met Glu Thr Leu Tyr Thr Arg Phe Gly Arg Leu Leu Ala
            675                 680                 685

Glu Tyr Thr Gly Ala Gln Gln Lys Leu Lys Gln Arg Ile Thr Val Leu
            690                 695                 700

Glu Val Lys Met Lys Gln Asn Thr Glu Asp Asp Tyr Leu Ser Asp Gly
705                 710                 715                 720

Met Asn Ser Pro Glu Pro Ala Ala Ala Glu Gln Pro
                725                 730

<210> SEQ ID NO 17
<211> LENGTH: 663
<212> TYPE: PRT
<213> ORGANISM: Bos taurus
<220> FEATURE:
<221> NAME/KEY: MISC_FEATURE
<222> LOCATION: (1)..(663)
<223> OTHER INFORMATION: CNGA2

<400> SEQUENCE: 17

Met Thr Glu Lys Ala Asn Gly Val Lys Ser Ser Pro Ala Asn Asn His
1               5                   10                  15

Asn His His Ala Pro Pro Ala Ile Lys Ala Ser Gly Lys Asp Asp His
                20                  25                  30

Arg Ala Ser Ser Arg Pro Gln Ser Ala Ala Ala Asp Asp Thr Ser Ser
            35                  40                  45

Glu Leu Gln Gln Leu Ala Glu Met Asp Ala Pro Gln Arg Arg Gly
        50                  55                  60

Gly Phe Arg Arg Ile Ala Arg Leu Val Gly Val Leu Arg Glu Trp Ala
65                  70                  75                  80

Tyr Arg Asn Phe Arg Glu Glu Pro Arg Pro Asp Ser Phe Leu Glu
                85                  90                  95

Arg Phe Arg Gly Pro Glu Leu His Thr Val Thr Thr Gln Gln Gly Asp
```

-continued

```
                100                 105                 110
Gly Lys Gly Asp Lys Asp Gly Glu Gly Lys Gly Thr Lys Lys Lys Phe
            115                 120                 125
Glu Leu Phe Val Leu Asp Pro Ala Gly Asp Trp Tyr Tyr Arg Trp Leu
        130                 135                 140
Phe Leu Ile Ala Leu Pro Val Leu Tyr Asn Trp Cys Leu Leu Val Ala
145                 150                 155                 160
Arg Ala Cys Phe Ser Asp Leu Gln Lys Gly Tyr Tyr Ile Val Trp Leu
                165                 170                 175
Val Leu Asp Tyr Val Ser Asp Val Val Tyr Ile Ala Asp Leu Phe Ile
            180                 185                 190
Arg Leu Arg Thr Gly Phe Leu Glu Gln Gly Leu Leu Val Lys Asp Thr
        195                 200                 205
Lys Lys Leu Arg Asp Asn Tyr Ile His Thr Met Gln Phe Lys Leu Asp
210                 215                 220
Val Ala Ser Ile Ile Pro Thr Asp Leu Ile Tyr Phe Ala Val Gly Ile
225                 230                 235                 240
His Asn Pro Glu Val Arg Phe Asn Arg Leu Leu His Phe Ala Arg Met
                245                 250                 255
Phe Glu Phe Phe Asp Arg Thr Glu Thr Arg Thr Ser Tyr Pro Asn Ile
            260                 265                 270
Phe Arg Ile Ser Asn Leu Ile Leu Tyr Ile Leu Ile Ile His Trp
        275                 280                 285
Asn Ala Cys Ile Tyr Tyr Ala Ile Ser Lys Ser Ile Gly Phe Gly Val
                290                 295                 300
Asp Thr Trp Val Tyr Pro Asn Ile Thr Asp Pro Glu Tyr Gly Tyr Leu
305                 310                 315                 320
Ser Arg Glu Tyr Ile Tyr Cys Leu Tyr Trp Ser Thr Leu Thr Leu Thr
                325                 330                 335
Thr Ile Gly Glu Thr Pro Pro Pro Val Lys Asp Glu Glu Tyr Leu Phe
            340                 345                 350
Val Ile Phe Asp Phe Leu Ile Gly Val Leu Ile Phe Ala Thr Ile Val
        355                 360                 365
Gly Asn Val Gly Ser Met Ile Ser Asn Met Asn Ala Thr Arg Ala Glu
    370                 375                 380
Phe Gln Ala Lys Ile Asp Ala Val Lys His Tyr Met Gln Phe Arg Lys
385                 390                 395                 400
Val Ser Lys Glu Met Glu Ala Lys Val Ile Arg Trp Phe Asp Tyr Leu
                405                 410                 415
Trp Thr Asn Lys Lys Ser Val Asp Glu Arg Glu Val Leu Lys Asn Leu
            420                 425                 430
Pro Ala Lys Leu Arg Ala Glu Ile Ala Ile Asn Val His Leu Ser Thr
        435                 440                 445
Leu Lys Lys Val Arg Ile Phe Gln Asp Cys Glu Ala Gly Leu Leu Val
    450                 455                 460
Glu Leu Val Leu Lys Leu Arg Pro Gln Val Phe Ser Pro Gly Asp Tyr
465                 470                 475                 480
Ile Cys Arg Lys Gly Asp Ile Gly Lys Glu Met Tyr Ile Ile Lys Glu
                485                 490                 495
Gly Lys Leu Ala Val Val Ala Asp Asp Gly Val Thr Gln Tyr Ala Leu
            500                 505                 510
Leu Ser Ala Gly Ser Cys Phe Gly Glu Ile Ser Ile Leu Asn Ile Lys
        515                 520                 525
```

Gly Ser Lys Met Gly Asn Arg Arg Thr Ala Asn Ile Arg Ser Leu Gly
                530                 535                 540

Tyr Ser Asp Leu Phe Cys Leu Ser Lys Asp Asp Leu Met Glu Ala Val
545                 550                 555                 560

Thr Glu Tyr Pro Asp Ala Lys Arg Val Leu Glu Arg Gly Arg Glu
                565                 570                 575

Ile Leu Met Lys Glu Gly Leu Leu Asp Glu Asn Glu Val Ala Ala Ser
                580                 585                 590

Met Glu Val Asp Val Gln Glu Lys Leu Glu Gln Leu Glu Thr Asn Met
                595                 600                 605

Asp Thr Leu Tyr Thr Arg Phe Ala Arg Leu Leu Ala Glu Tyr Thr Gly
                610                 615                 620

Ala Gln Gln Lys Leu Lys Gln Arg Ile Thr Val Leu Glu Thr Lys Met
625                 630                 635                 640

Lys Gln Asn Asn Glu Asp Asp Ser Leu Ser Asp Gly Met Asn Ser Pro
                645                 650                 655

Glu Pro Pro Ala Glu Lys Pro
                660

<210> SEQ ID NO 18
<211> LENGTH: 664
<212> TYPE: PRT
<213> ORGANISM: Artificial Sequence
<220> FEATURE:
<223> OTHER INFORMATION: mammalian CNGA2 consensus sequence
<220> FEATURE:
<221> NAME/KEY: MISC_FEATURE
<222> LOCATION: (1)..(664)
<223> OTHER INFORMATION: Xaa = any naturally occurring amino acid

<400> SEQUENCE: 18

Met Met Thr Glu Lys Ser Asn Gly Val Lys Ser Ser Pro Ala Asn Asn
1               5                   10                  15

His Asn His His Ala Pro Pro Ala Ile Lys Ala Asn Gly Lys Asp Asp
                20                  25                  30

His Arg Ala Gly Ser Arg Pro Gln Ser Xaa Ala Ala Asp Asp Asp Thr
                35                  40                  45

Ser Ser Glu Leu Gln Arg Leu Ala Glu Met Asp Ala Pro Gln Gln Gly
                50                  55                  60

Arg Gly Gly Phe Arg Arg Ile Val Arg Leu Val Gly Val Ile Arg Asp
65                  70                  75                  80

Trp Ala Asn Lys Asn Phe Arg Glu Glu Pro Arg Pro Asp Ser Phe
                85                  90                  95

Leu Glu Arg Phe Arg Gly Pro Glu Leu Gln Thr Val Thr Thr Gln Gln
                100                 105                 110

Gly Asp Gly Lys Gly Asp Lys Asp Gly Glu Gly Lys Gly Thr Lys Lys
                115                 120                 125

Lys Phe Glu Leu Phe Val Leu Asp Pro Ala Gly Asp Trp Tyr Tyr Arg
                130                 135                 140

Trp Leu Phe Val Ile Ala Met Pro Val Leu Tyr Asn Trp Cys Leu Leu
145                 150                 155                 160

Val Ala Arg Ala Cys Phe Ser Asp Leu Gln Arg Gly Tyr Phe Val Val
                165                 170                 175

Trp Leu Val Leu Asp Tyr Phe Ser Asp Val Val Tyr Ile Ala Asp Leu
                180                 185                 190

Phe Ile Arg Leu Arg Thr Gly Phe Leu Glu Gln Gly Leu Leu Val Lys

-continued

```
              195                 200                 205
Asp Pro Lys Lys Leu Arg Asp Asn Tyr Ile His Thr Leu Gln Phe Lys
    210                 215                 220
Leu Asp Val Ala Ser Ile Ile Pro Thr Asp Leu Ile Tyr Phe Ala Val
225                 230                 235                 240
Gly Ile His Ser Pro Glu Val Arg Phe Asn Arg Leu Leu His Phe Ala
                245                 250                 255
Arg Met Phe Glu Phe Phe Asp Arg Thr Glu Thr Arg Thr Ser Tyr Pro
                260                 265                 270
Asn Ile Phe Arg Ile Ser Asn Leu Val Leu Tyr Ile Leu Val Ile Ile
            275                 280                 285
His Trp Asn Ala Cys Ile Tyr Tyr Ala Ile Ser Lys Ser Ile Gly Phe
        290                 295                 300
Gly Val Asp Thr Trp Val Tyr Pro Asn Ile Thr Asp Pro Glu Tyr Gly
305                 310                 315                 320
Tyr Leu Ala Arg Glu Tyr Ile Tyr Cys Leu Tyr Trp Ser Thr Leu Thr
                325                 330                 335
Leu Thr Thr Ile Gly Glu Thr Pro Pro Pro Val Lys Asp Glu Glu Tyr
            340                 345                 350
Leu Phe Val Ile Phe Asp Phe Leu Ile Gly Val Leu Ile Phe Ala Thr
        355                 360                 365
Ile Val Gly Asn Val Gly Ser Met Ile Ser Asn Met Asn Ala Thr Arg
    370                 375                 380
Ala Glu Phe Gln Ala Lys Ile Asp Ala Val Lys His Tyr Met Gln Phe
385                 390                 395                 400
Arg Lys Val Ser Lys Asp Met Glu Ala Lys Val Ile Lys Trp Phe Asp
                405                 410                 415
Tyr Leu Trp Thr Asn Lys Lys Thr Val Asp Glu Arg Glu Val Leu Lys
                420                 425                 430
Asn Leu Pro Ala Lys Leu Arg Ala Glu Ile Ala Ile Asn Val His Leu
            435                 440                 445
Ser Thr Leu Lys Lys Val Arg Ile Phe Gln Asp Cys Glu Ala Gly Leu
        450                 455                 460
Leu Val Glu Leu Val Leu Lys Leu Arg Pro Gln Val Phe Ser Pro Gly
465                 470                 475                 480
Asp Tyr Ile Cys Arg Lys Gly Asp Ile Gly Lys Glu Met Tyr Ile Ile
                485                 490                 495
Lys Glu Gly Lys Leu Ala Val Val Ala Asp Asp Gly Val Thr Gln Tyr
                500                 505                 510
Ala Leu Leu Ser Ala Gly Ser Cys Phe Gly Glu Ile Ser Ile Leu Asn
            515                 520                 525
Ile Lys Gly Ser Lys Met Gly Asn Arg Arg Thr Ala Asn Ile Arg Ser
        530                 535                 540
Leu Gly Tyr Ser Asp Leu Phe Cys Leu Ser Lys Asp Asp Leu Met Glu
545                 550                 555                 560
Ala Val Thr Glu Tyr Pro Asp Ala Lys Lys Val Leu Glu Glu Arg Gly
                565                 570                 575
Arg Glu Ile Leu Met Lys Glu Gly Leu Leu Asp Glu Asn Glu Val Ala
                580                 585                 590
Ala Ser Met Glu Val Asp Val Gln Glu Lys Leu Glu Gln Leu Glu Thr
            595                 600                 605
Asn Met Glu Thr Leu Tyr Thr Arg Phe Ala Arg Leu Leu Ala Glu Tyr
        610                 615                 620
```

```
Thr Gly Ala Gln Gln Lys Leu Lys Gln Arg Ile Thr Val Leu Glu Thr
625                 630                 635                 640

Lys Met Lys Gln Asn Asn Glu Asp Asp Tyr Leu Ser Asp Gly Met Asn
            645                 650                 655

Ser Pro Phe Pro Ala Ala Ala Glu
            660

<210> SEQ ID NO 19
<211> LENGTH: 821
<212> TYPE: PRT
<213> ORGANISM: Artificial Sequence
<220> FEATURE:
<223> OTHER INFORMATION: human CNGA and CNGB consensus sequence
<220> FEATURE:
<221> NAME/KEY: MISC_FEATURE
<222> LOCATION: (1)..(821)
<223> OTHER INFORMATION: Xaa = any naturally occurring amino acid

<400> SEQUENCE: 19

Met Xaa Xaa Xaa Xaa Ile Gly Thr Gln Xaa Ser Xaa Xaa Ser Xaa Xaa
1               5                   10                  15

Asn Leu Xaa Val Pro Xaa Xaa Glu Lys Ala Xaa Xaa Arg Ala Glu Asn
            20                  25                  30

Xaa Gly Xaa Ser Arg Ala His Ser Xaa Ala Asp Asp Xaa Ala Ser Xaa
        35                  40                  45

Xaa Xaa Xaa Xaa Xaa Xaa Xaa Glu Xaa Glu Xaa Leu Ala Asp Xaa Ala
    50                  55                  60

Xaa Gly Ser Phe Ser Gly Xaa Gly Xaa Arg Lys Xaa Xaa Xaa Xaa Xaa
65              70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Arg Leu
            100                 105                 110

Xaa Xaa Leu Xaa Arg Xaa Trp Ala Xaa Xaa Asn Val Arg Xaa Xaa Xaa
        115                 120                 125

Pro Xaa Pro Asp Ser Glu Pro Glu Glu Phe Lys Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Glu Leu Lys Glu Val Lys Ser Gln Asp Xaa Asp Val Lys Xaa Asp Glu
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Ser Glu Asp Lys Lys Xaa Lys Lys Lys Xaa Xaa Xaa Xaa Xaa Lys
                245                 250                 255

Leu Leu Xaa Val Ile Asp Pro Ser Gly Asp Xaa Leu Tyr Tyr Leu Trp
            260                 265                 270

Leu Phe Xaa Ile Ala Leu Pro Val Asn Tyr Asn Trp Cys Leu Leu Val
        275                 280                 285

Ala Arg Ala Cys Phe Pro Asp Leu Gln Ser Asp Tyr Leu His Tyr Trp
```

```
                290                 295                 300
Leu Val Leu Asp Tyr Val Ser Asp Val Val Tyr Leu Leu Asp Met Xaa
305                 310                 315                 320

Phe Val Arg Thr Arg Thr Gly Phe Leu Glu Gln Gly Leu Leu Val Val
                325                 330                 335

Asp Thr Asn Lys Leu Arg Asn Asn Tyr Lys Thr Thr Leu Gln Phe Lys
                340                 345                 350

Leu Asp Val Ala Ser Leu Ile Pro Thr Asp Leu Leu Tyr Leu Lys Val
                355                 360                 365

Gly Xaa Asn Tyr Pro Glu Val Arg Leu Asn Arg Leu Leu Lys Phe Ser
370                 375                 380

Arg Leu Phe Glu Phe Phe Asp Arg Thr Glu Thr Arg Thr Asn Tyr Pro
385                 390                 395                 400

Asn Ile Phe Arg Ile Ile Asn Leu Val Leu Tyr Ile Leu Val Ile Ile
                405                 410                 415

His Trp Asn Ala Cys Val Tyr Ala Ile Ser Lys Tyr Ile Gly Phe
                420                 425                 430

Gly Thr Asp Thr Trp Val Tyr Pro Gly Ile Gly Asp Pro Glu Phe Gly
                435                 440                 445

Arg Leu Ala Arg Glu Tyr Ile Tyr Ser Leu Tyr Trp Ser Thr Leu Thr
450                 455                 460

Leu Thr Thr Ile Gly Glu Thr Pro Pro Val Thr Asp Glu Glu Tyr
465                 470                 475                 480

Val Phe Val Val Val Asp Phe Leu Ile Gly Val Leu Ile Phe Ala Thr
                485                 490                 495

Ile Val Gly Asn Met Gly Ser Val Ile Ser Asn Met Asn Ala Ala Arg
                500                 505                 510

Ala Glu Phe Gln Ala Lys Ile Asp Ala Val Lys Gln Tyr Met Asn Phe
                515                 520                 525

Arg Lys Val Ser Lys Asp Val Glu Lys Arg Val Ile Thr Trp Phe Asp
                530                 535                 540

Tyr Leu Trp Thr Asn Lys Lys Thr Val Asp Glu Ser Glu Val Leu Lys
545                 550                 555                 560

Xaa Leu Pro Asp Lys Leu Arg Ala Glu Ile Ala Ile Asn Val His Leu
                565                 570                 575

Ser Thr Leu Ser Lys Val Arg Ile Phe Gln Asp Cys Glu Ala Gly Leu
                580                 585                 590

Leu Val Glu Leu Val Leu Lys Leu Arg Pro Gln Val Tyr Ser Pro Gly
                595                 600                 605

Asp Tyr Val Cys Lys Lys Gly Asp Ile Gly Lys Glu Met Tyr Ile Ile
                610                 615                 620

Lys Glu Gly Lys Leu Ala Val Val Ala Asp Xaa Asp Gly Val Thr Gln
625                 630                 635                 640

Leu Val Val Leu Ser Ala Gly Ser Val Phe Gly Glu Ile Ser Ile Leu
                645                 650                 655

Asn Ile Lys Gly Ser Lys Ser Gly Asn Arg Arg Thr Ala Asn Ile Val
                660                 665                 670

Ser Leu Gly Tyr Ser Asp Leu Phe Cys Leu Ser Lys Asp Asp Leu Met
                675                 680                 685

Glu Ala Leu Thr Glu Tyr Pro Asp Ala Lys Lys Ile Leu Glu Glu Lys
                690                 695                 700

Gly Arg Glu Ile Leu Met Lys Asp Asn Leu Leu Asp Glu Asn Xaa Ala
705                 710                 715                 720
```

-continued

```
Xaa Xaa Xaa Xaa Xaa Xaa Xaa Xaa Xaa Ala Gly Xaa Ala Thr Pro
            725                 730                 735

Lys Asp Leu Glu Glu Lys Leu Gly Gly Leu Gly Lys Ser Xaa Xaa Xaa
            740                 745                 750

Xaa Xaa Xaa Xaa Xaa Xaa Leu Asp Thr Leu Gln Thr Arg Phe Ala Arg
            755                 760                 765

Leu Leu Ala Glu Tyr Glu Ala Ala Gln Gln Lys Xaa Xaa Leu Lys Gln
        770                 775                 780

Arg Leu Ser Xaa Leu Glu Lys Gln Xaa Lys Glu Gly Xaa Xaa Xaa Xaa
785                 790                 795                 800

Asp Xaa Glu Xaa Ala Asp Asp Glu Gly Glu Pro Asp Glu Xaa Ala Pro
            805                 810                 815

Xaa Asp Glu Pro Glu
            820

<210> SEQ ID NO 20
<211> LENGTH: 5
<212> TYPE: PRT
<213> ORGANISM: Artificial Sequence
<220> FEATURE:
<223> OTHER INFORMATION: mammalian Gi protein

<400> SEQUENCE: 20

Asp Cys Gly Leu Phe
1               5

<210> SEQ ID NO 21
<211> LENGTH: 5
<212> TYPE: PRT
<213> ORGANISM: Artificial Sequence
<220> FEATURE:
<223> OTHER INFORMATION: mammalian Gi protein

<400> SEQUENCE: 21

Glu Cys Gly Leu Tyr
1               5

<210> SEQ ID NO 22
<211> LENGTH: 5
<212> TYPE: PRT
<213> ORGANISM: Artificial Sequence
<220> FEATURE:
<223> OTHER INFORMATION: mammalian Gi protein

<400> SEQUENCE: 22

Gly Cys Gly Leu Tyr
1               5

<210> SEQ ID NO 23
<211> LENGTH: 5
<212> TYPE: PRT
<213> ORGANISM: Artificial Sequence
<220> FEATURE:
<223> OTHER INFORMATION: mammalian Gi protein

<400> SEQUENCE: 23

Tyr Ile Gly Leu Cys
1               5
```

CELL-BASED ASSAYS EMPLOYING VOLTAGE AND CALCIUM DYES

This application claims the benefit of U.S. Provisional Application Ser. No. 60/515,442, filed Oct. 30, 2003 and U.S. Provisional Application Ser. No. 60/589,012, filed Jul. 20, 2004, both of which are herein incorporated by reference in their entirety for all purposes. This application is also a continuation-in-part of U.S. application Ser. No. 10/087,217, filed Mar. 4, 2002 which claims the benefit of U.S. Provisional Application Ser. No. 60/330,663, filed Oct. 26, 2001, which are herein incorporated by reference in their entirety for all purposes.

FIELD OF THE INVENTION

The invention relates generally to cellular physiology. In particular, the invention relates to novel tools for use in cell-based assays that employ calcium and voltage-based dyes and other indicators, including novel CNG mutants for use in improved cyclic nucleotide assays, and fluorescence quencher molecules for use in novel cell-based assays employing fluorescent voltage dyes. Such tools are useful for measuring the activity of G protein coupled receptors, and in other assays involving changes in intracellular levels of cyclic nucleotides.

BACKGROUND OF THE INVENTION

G-protein-coupled receptors (GPCRs) comprise a large super-family of integral membrane proteins characterized by having 7 hydrophobic alpha helical transmembrane (TM) domains with three intracellular and three extracellular loops (Ji, et al., *J Biol Chem* 273:17299-17302, 1998). In addition all GPCRs contain N-terminal extracellular and C-terminal intracellular domains. Binding of extracellular ligand may be mediated by the transmembrane domains, the N-terminus, or extracellular loops, either in alone or in combination. For example binding of biogenic amines such as epinephrine, norepinephrine, dopamine, and histamine is thought to occur primarily at the TM3 site while TM5 and TM6 provide the sites for generating an intracellular signal. Agonist binding to GPCRs results in activation of one or more intracellular heterotrimeric GTP-binding proteins (G proteins) which, in turn, transduce and amplify the signal by subsequent modulation of down-stream effector molecules (such as enzymes, ion channels and transporters). This in turn results in rapid production of second messengers (such as cAMP, cGMP, inositol phosphates, diacylglycerol, cytosolic ions).

GPCRs mediate signal transduction across a cell membrane upon the binding of a ligand to a GPCR. The intracellular portion of the GPCR interacts with a G protein to modulate signal transduction from outside to inside a cell. A GPCR is thus coupled to a G protein. There are three polypeptide subunits in a G-protein complex: an alpha subunit—which binds and hydrolyzes GTP—and a dimeric beta-gamma subunit. In the inactive state, the G protein exists as a heterotrimer of the alpha and beta-gamma subunits. When the G protein is inactive, guanosine diphosphate (GDP) is associated with the alpha subunit of the G protein. When a GPCR is bound and activated by a ligand, the GPCR binds to the G-protein heterotrimer and decreases the affinity of the G alpha subunit for GDP. In its active state, the G subunit exchanges GDP for guanine triphosphate (GTP) and active G alpha subunit disassociates from both the GPCR and the dimeric beta-gamma subunit. The disassociated, active G alpha subunit transduces signals to effectors that are "downstream" in the G-protein signaling pathway within the cell. Eventually, the G protein's endogenous GTPase activity returns active G subunit to its inactive state, in which it is associated with GDP and the dimeric beta-gamma subunit.

The transduction of the signal results in the production of second messenger molecules. Once produced, the second messengers have a wide variety of effects on cellular activities. One such activity is the activation of cyclic nucleotide-gated (CNG) channels by the cyclic nucleotides cAMP and cGMP. CNG channels are membrane spanning molecules that control the flux of cations through the cellular membrane. The channels are activated—opened—by increased intracellular concentrations of cyclic nucleotide. Once opened the channels conduct mixed cation currents, including ions of $Na^+$, $K^+$, $Mg^{2+}$ and $Ca^{2+}$, for example. The activity of the CNG channels couples electrical excitation and $Ca^{2+}$ signaling to changes in the intracellular concentration of cyclic nucleotides (FIG. 1).

Receptor function is regulated by the G protein itself (GTP-bound form is required for coupling), by phosphorylation (by G-protein-coupled receptor kinases or GRKs) and by binding to inhibitory proteins known as β-arrestins (Lefkowitz, *J Biol Chem*, 273:18677-18680, 1998). It has long been established that many medically significant biological processes are mediated by proteins participating in signal transduction pathways that involve G proteins and/or second messengers (Lefkowitz, *Nature*, 351:353-354, 1991). In fact, nearly one-third of all prescription drugs are GPCR ligands (Kallal et al., *Trends Pharmacol Sci*, 21:175-180, 2000).

GPCRs fall into three major classes (and multiple subclasses) based on their known (or predicted) structural and functional properties (Rana et al., *Ann Rev Pharmacol Toxicol*, 41:593-624, 2001; Marchese et al., *Trends Pharmacol Sci*, 20:370-375, 1999). Most of these receptors fall into class A, including receptors for odorants, light, and biogenic amines, for chemokines and small peptides, and for several glycopeptide/glycoprotein hormones. Class B receptors bind higher molecular weight hormones while class C includes $GABA_B$ receptors, taste receptors, and $Ca^{2+}$-sensing receptors. GPCRs are found in all tissues. However, expression of any individual receptor may be limited and tissue-specific. As such some GPCRs may be used as markers for specific tissue types.

As might be expected from the wide range of GPCRs and GPCR ligands, aberrant function of these molecules has been implicated in a large number of human disease states (Rana et al. and Ji et al., supra). GPCR agonists and antagonists have been developed to treat many of these diseases. For example the important group of receptors for biogenic amines has been the target of a large number of successful drugs. Among the receptors in this group are those for epinephrine and norepinephrine (α- and β-adrenergic receptors), dopamine, histamine, and serotonin. Examples of diseases in which GPCR function has been implicated include, but are by no means limited to: heart disease (e.g. tachycardia, congestive heart failure, etc.), asthma, hypertension, allergic reactions (including anaphylactic shock), gastrointestinal disorders, and a wide range of neurological disorders (e.g. Parkinson's disease, depression, schizophrenia, etc.). Finally, many receptors for drugs of abuse are GPCRs.

In many animals, GPCRs are found throughout the organism and are responsible for the maintenance of normal function as well as for pathological conditions. In other instances, the expression of specific GPCRs or families of GPCRs is very tightly controlled, e.g., being expressed only during early developmental stages, etc. Consequently, it is important to find compounds that can stimulate or activate GPCRs, or inhibit or deactivate GPCRs as needed. Agonists—compounds that stimulate the normal function of the GPCRs—have been used to treat asthma, Parkinson's disease, acute heart failure, osteoporosis, hypotension, etc. Antagonists, compounds that interfere with or block normal function have been used to treat, hypertension, myocardial infarction, ulcers, asthma, allergies, psychiatric and neurological disorders, anorexia and bulimia.

In addition to well-characterized receptors, many "orphan" receptors have been cloned (Marchese et al., supra) which are known from sequence similarities to be part of these families, but for which no function or ligand(s) have been discerned. Given the central role of GPCRs in control of diverse cellular activities, there remains a need in the art for methods to identify the agonists and antagonists of these "orphan" receptors as well as to identify additional antagonists for those receptors whose agonists—ligands—are known.

As the first recognized second messenger, cAMP is synthesized by adenylate cyclase in response to activation of many receptors coupled to G proteins $G_s$ and $G_{olf}$ and cyclase activity is inhibited by activation of receptors coupled to G protein $G_i$. cAMP activates cAMP-dependent protein kinase A (PKA) resulting in profound cellular responses. Physiologically, cAMP mediates such hormonal responses as mobilization of stored energy (e.g., the breakdown of carbohydrates in liver or triglycerides in fat cells, conservation of water by kidney, and $Ca^{2+}$ homeostasis), control of the rate and contraction force of the heart muscle, relaxation of smooth muscle, production of sex hormones, and many other endocrine and neural processes.

There are a number of cAMP assays currently available. They include transcription reporter assay where a luciferase reporter is driven with a cAMP response promoter element CRE, cAMP immunoassay (Applied Biosystems Forster City, Calif.), an in vitro enzymatic assay for adenylyl cyclase (Molecular Devices, Sunnyvale, Calif.) and cAMP fluorescence polarization assay (PerkinElmer Life Sciences, Boston, Mass.). However, all these assays are end point assays where the cells are lysed and extracts are used for the tests. R. Y. Tsien and his colleagues have also developed fluorescent probes that report cAMP levels in single cells. However, the methods of application of these probes to cells makes them not suitable for high throughput screening formats (Adams et al., 1991, *Nature* 349:694-697; Zoccolo et al., 2000, *Nat. Cell Biol.* 2:25-29). There is a need in the art to be able to detect the activation of individual living cells for their cAMP production, particularly in a heterogeneous cell or tissue environment. Such detection capability would further allow the examination of receptor activation and cellular response to complex stimuli, as in the case of induced long-term memory. There also exists in the art a need for the ability to directly examine the cAMP in live cells in order to identify ligands for orphan GPCRs based on the concurrent examination of both $Ca^{2+}$ and cAMP activation in a given cell as well as to identify agents that modulate GPCR-mediated activity. These and other needs are met by the present invention.

SUMMARY OF THE INVENTION

The assays and methods of the present invention provide novel tools for use in cAMP assays. In particular, the invention provides novel CNG mutants for use in CNG-based assays, particularly assays for monitoring the activity of GPCRs and GPCR signaling cascades. The novel CNG mutants contain one or more mutations that remove calcium blockage of the channel pore, resulting in improved sensitivity and specificity to cAMP (vs. cGMP) and significant improvement in CNG-based assays for cAMP activation.

Also provided are quencher molecules for use in CNG-based assays and other assays employing calcium and voltage-based dyes. In such assays, membrane-impermeable quenchers have often been used in combination with fluorescence indicators to reduce background extracellular fluorescence while maintaining intracellular fluorescence intact. However, assays may be negatively effected when such quenchers exhibit pharmacological interference with the biological interaction being measured. The quencher molecules of the present invention are pharmacologically inert and therefore compatible with assaying of peptide, protein, nucleoside lipid and small organic molecules. Therefore, these molecules may be employed in a wide variety of assays employing fluorescent voltage dyes, including the GPCR/CNG assays exemplified herein.

BRIEF DESCRIPTION OF THE DRAWINGS

FIGS. 8A-C provide a sequence alignment of human CNG channels CNGA1 (SEQ ID NO: 0.9), CNGA2 (SEQ ID NO: 10), CNGA3 (SEQ ID NO: 11), CNGB1 (SEQ ID NO: 12), CNGB2 (SEQ ID NO: 13) and CNGB3 (SEQ ID NO: 14). A consensus sequence of this multiple alignment is also shown (SEQ ID NO: 19).

FIGS. 9A-B provide a sequence alignment of CNGA2 channels from the following mammals: human (SEQ ID NO: 10), rat (SEQ ID NO: 2), mouse (SEQ ID NO: 15), rabbit (SEQ ID NO: 16) and bull (SEQ ID NO: 17). A consensus sequence of this multiple alignment is also shown (SEQ ID NO: 18).

FIGS. 10A-D. FIG. 10A depicts the response of HEK293H-CNG cells to 1 µM isoproterenol. FIG. 10B depicts the response of non-transformed parental HEK293H cells to 1 µM isoproterenol. FIG. 10C depicts dose-response curves of HEK293H-CNG cells to 0 (control), 1 nM, 3 mM, 10 nM, 30 nM, 0.1 µM, 0.3 µM and 1 µM isoproterenol. FIG. 10D depicts the well-to-well consistency of the readings for measuring CNG activation.

FIG. 11 depicts calcium uptake by HEK293H-CNG cells in a dose-dependent manner to 0 (control), 0.3, 1, 3, 10, 30 and 300 nM isoproterenol.

FIGS. 12A-B. FIG. 12A shows voltage sensitive fluorescence of the same living cells immediately before the addition of 1 µM isoproterenol and 15, 30 and 45 seconds after addition. FIG. 12B depicts the background corrected average fluorescence of 71 imaged cells.

FIG. 22 is a graph showing glucagon dose-responses in the presence of quencher dyes. Cell line: ASC0089 (GCGR). Glucagon potency increased using nitrazine yellow as a quencher.

FIG. 23 is a graph showing VIP dose-responses in the presence of quencher dyes. Cell line: ASC0145 (VIP2R). VIP potency increased using nitrazine yellow as a quencher by more than one order comparing using a commercial dye kit from Molecular Devices, Corp. (MDC, Cat #R-8034).

FIG. 25 shows the formula of Nitrazine Yellow.

FIG. 26 shows the formula of Nitro Red.

DETAILED DESCRIPTION OF THE PREFERRED EMBODIMENTS

I. General Description

Figure 1:
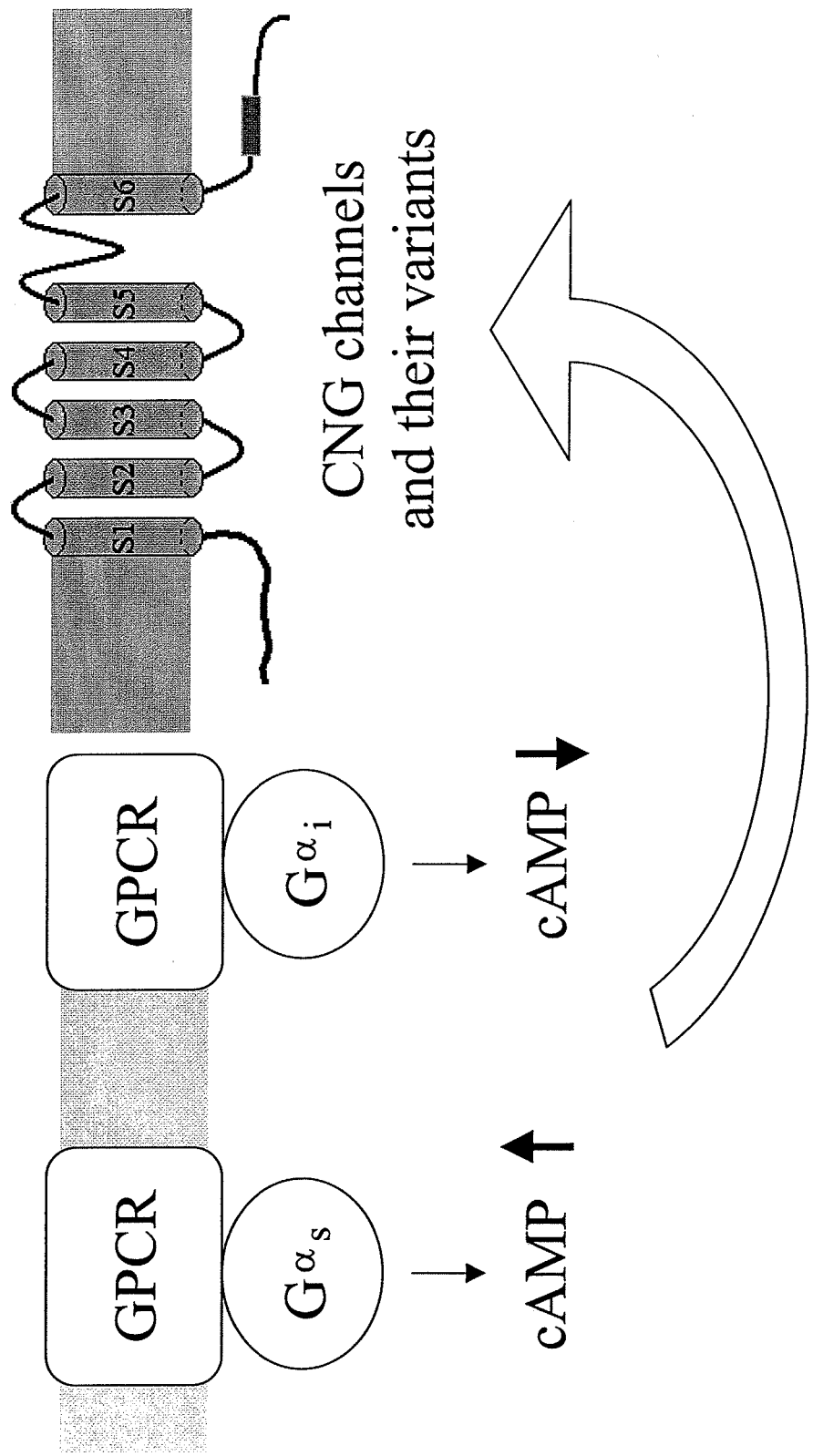
FIG. 1 is a schematic of the signaling pathway from a GPCR to a CNG channel.

The novel dye quencher formulations of the present invention have broad applicability in any cell-based assay that employs a fluorescent detector dye. The CNG mutants of the present invention have broad applicability to any cell based assay for measuring intracellular cAMP levels. These utilities are exemplified by the GPCR/CNG assays described herein, and in application Ser. No. 10/087,217, which is hereby incorporated by reference in its entirety.

Novel Quencher/Dye Formulations

Membrane impermeable fluorescence quenchers are often used in combination with fluorescence indicators to reduce background fluorescence noise and simplify assay procedures. For example, trypan blue was used to reduce extracellular fluorescence background while maintaining intracellular fluorescence intact in assays monitoring internalization of fluorescein conjugates in macrophage cells (Sahlin et al., 1983; Hed et al., 1987; Wan et al., 1993). Metal ion quencher and absorbance dye quencher were used in combination with fluorescent calcium dyes to measure intracellular calcium (Etter et al., 1996; Davies et al., 1997; Mehlin et al., *Biotechniques*, 2003). Collisional quencher I⁻and an absorbance dye quencher were used in combination with fluorescent voltage dyes to monitor membrane potential (Melikyan et al., 1996; Leenhouts & Kruijff, 1995; US Patent application publication No.: US2003/0087332 A1). Absorbance dye quenchers were used in combination with a fluorescent dye to measure gene transcription (U.S. Pat. No. 6,221,612).

Many dyes used as quenchers were developed for the textile industry. Consequently, the pharmacological effects on living cells typically remains unknown. Assay performance can be negatively impacted when quenchers have pharmacological actions on cell signaling pathways, receptors, or interact with ligands resulting, for example, from covalent, electrostatic, hydrogen and Van der Waals interactions. These interactions are particularly problematic when screening ligands comprised of protein, peptide, nucleoside, lipid or small organic molecules. The disclosed invention provides quencher dyes that are compatible with assaying of peptide, protein, nucleoside, lipid and small organic molecules, and methods of identifying the same.

Accordingly, the present invention provides a method of identifying a biologically inert fluorescence quencher comprising (a) providing a collection of candidate quencher molecules;
(b) providing a panel of at least five receptors, said receptors selected from at least three types and distinguished by pharmacophores, said pharmacophores comprising biogenic amines, adenosines, lipids, alkaloids, amino acids, peptides, and proteins,
(c) assaying activity of said receptors in the presence of an activating pharmacophore and in the presence and absence of members of said collection of candidate quencher molecules;

wherein a biologically inert fluorescence quencher has no effect on the activation of said panel of receptors. In such assays, activation of the receptor is typically quantitated in a manner that does not involve the functional use of the quencher.

In particular, it has been found that trypan blue, a commonly used quencher, has tendency to reduce the potency of a peptide ligands such as glucagon. Nitrazine yellow and a structurally similar molecule, nitro red, were identified as useful quenchers for fluorescent voltage dyes, showing little effect on responses of peptides and other small organic molecules. These quencher dyes have broad applicability in formulations for cell-based assays that use a variety of fluorescent detector dyes. In particular, the quencher dyes of the present invention may be used in combination with a voltage dye to monitor activity of CNG channels in a live-cell assay for agonists, antagonists or allosteric modulators. The dye/quencher formulation can also be used for deorphanization of GPCRs and other events that alter intracellular cAMP, calcium, and gene expression levels. Formulations of the quencher dyes of the invention with a variety of fluorescent detector dyes are provided for drug discovery, toxicology and other cell-based studies.

The formulations of the present invention are particularly useful for homogeneous assays employing at least one of a fluorescent plate reader, a single-cell imaging platform a facs sorter, and an electrophysiology platform. The formulations of the invention may be used in any cell-based assay where cellular uptake is mediated by at least one of endocytosis, receptor internalization, viral infection, peptide-mediated uptake and lipid-mediated uptake. Further, it should be understood that the level of fluorescence may increase or decrease in response to the particular activity being measured.

One advantage of the current dye/quencher/buffer formulation is the ability to omit wash steps normally required to remove unbound dye in solution. The newly developed quencher(s) can be used in combination with other fluorescent biomarkers whenever a no-wash format is desirable. Examples include but are not limited to use of cells sensitive to mechanical stress, cells or assays wherein the biological response is dampened or perturbed as a result of medium/buffer changes, assays where the presence of at least one dye or assay component is required throughout the duration of the assay, such as occurs during steadily up-take of specific probes, e.g., vital tracers, or in long-term studies of cell differentiation, motility or division, and in assays in which probes leak out of the cells and washing is not possible/desirable.

Yet another advantage of the present quencher formulations is the ability to use a variety of calcium dyes in combination with the quencher. These include Fluo 3, Fluo 4 and Fura-2. In particular, Fura-2 is a ratio dye, providing higher accuracy measurements by minimizing effects of uneven dye loading between cells, uneven dye loading within single cells, uneven sample illumination, photobleaching, and artifacts, such as those generated if a ligand is inherently fluorescent.

The quenchers of the present invention have utility in certain FRET or BRET-based assays. Non-fluorescent quenchers such as Dabcyl and QSY dyes (Molecular Probes) are used in FRET combinations where a fluorescent (or luminescent) donor is quenched by a non-fluorescent acceptor (efficient quenchers such as Dabcyl reduce fluorescence emission of most fluorophores by 99%). When FRET is disrupted, the quencher no longer absorbs the donor emission which is then detected as an increase in the specific fluorescence emission of the fluorochrome present in the donor.

Non-fluorescent quenchers have the advantage of eliminating the potential problem of background fluorescence resulting from direct (i.e. nonsensitized) acceptor excitation (rather than excitation via the FRET donor molecule). Examples of commercially available probes containing fluorescent donor-non fluorescent acceptor pairs include probes aimed at detecting proteolysis (EDANS fluorophore/Dabcyl pair for HIV protease and renin substrates; FRET is disrupted upon cleavage of the substrate by specific proteases) (Molecular Probes) and nucleic acid hybridization (molecular beacons: hairpin oligonucleotides with a fluorochrome attached to one end and a non-fluorescent quencher attached to the other end; upon hybridization to a complementary sequence, the hairpin unfolds and FRET is disrupted). Because the quenchers of the present invention are relatively inert to peptide or proteins, their use in such assays decreases nonspecific binding of cellular materials or peptide agonists/antagonists.

Novel CNG Mutants for Cell-Based cAMP Assays

Calcium ions present in extracellular media must be chelated in assays applying voltage dyes when using wild-type CNG channels. Otherwise, calcium binds to a glutamate residue at channel pore, thereby blocking ionic currents. The novel CNG mutants of the present invention contain one or more mutations in the channel pore domain, thereby removing calcium blockage of the currents. In addition, these mutations make CNG channels more permeable to calcium. Several combinations of mutations were generated and tested at three positions within the CNG that affect cAMP binding affinity and channel permeability to calcium. Mutations were identified that, alone or in combination, provide significant improvements in the assay that are particularly useful for high-throughput screening. The invention has broad applications, particularly in screening receptors, particularly 7-transmembrane receptors. For instance, the invention provides assays that can be used to detect the binding of agonists, antagonists, or allosteric modulators of 7-transmembrane receptors.

The novel mutants of the present invention may be expressed in combination with other CNG subunits to form heteromeric channels having several advantages. Native CNG channels in olfactory receptor neurons are composed of three subunits: CNGA2, CNGA4 (Bradley J, Li J, Davidson N, Lester H A, Zinn K. (1994). Heteromeric olfactory cyclic nucleotide-gated channels: a subunit that confers increased sensitivity to cAMP. *Proc Natl Acad Sci USA*. 1994 Sep. 13; 91(19):8890-4) and CNG4.3 (Sautter A, Zong X, Hofmann F, Biel M. (1998). An isoform of the rod photoreceptor cyclic nucleotide-gated channel beta subunit expressed in olfactory neurons. *Proc Natl Acad Sci USA*. 1998 Apr. 14; 95(8):4696-701; Bonigk W, Bradley J, Muller F, Sesti F, Boekhoff I, Ronnett G V, Kaupp U B, Frings S. (1999). The native rat olfactory cyclic nucleotide-gated channel is composed of three distinct subunits. *J Neurosci*. 1999 Jul. 1; 19(13):5332-47; Bradley J, Frings S, Yau K W, Reed R. (2001). Nomenclature for ion channel subunits. *Science*. 2001 Dec. 7; 294 (5549):2095-6). The CNGA2 protein can form homomeric channels, whereas CNGA4 and CNG4.3 can not. However, coexpression of CNGA2 and CNGA4 and/or CNG4.3 can form heteromeric channels comprised of either two or three subunits. In comparison with homomeric CNGA2 channels expressed in heterologous cells, the heteromeric channels have several advantages, including: (1) higher sensitivity to cAMP (increase detection sensitivity), (2) weakened outward current rectification (resulting in an increased membrane depolarization signal), and (3) better channel assembly with a consequence of higher expression and lower toxicity to cells.

Overall benefits of the new mutants include (1) increased signals when using voltage or calcium dyes; and (2) assays can now be conducted in physiological calcium-containing media. For instance, the novel calcium-insensitive CNG mutations of the invention enable the loading of the membrane potential/quencher cocktail in a more physiological buffer (such as HBSS, Hank's Balanced Salt Solution) rather than in DPBS (Phosphate Buffer Saline calcium/magnesium-free). Cell morphology is much better retained and cells adhere more tightly to the growth surface because the physiologically balanced divalent cation concentration is maintained during the loading period. Also, EGTA is not required in the compound addition buffer and cell shrinkage previously observed upon compound buffer addition is markedly reduced. Overall, such improvements are associated with greater cell responsiveness leading to enhanced overall sensitivity of the assay (both in cell imaging and whole-well reading formats).

The novel calcium-insensitive CNG mutations of the invention enable the simultaneous measurements of cAMP-dependent changes in calcium and membrane potential in the same cells providing the basis for multiplexed assays for ligands with unknown receptor specificity or for receptor de-orphanization (receptors with unknown signaling pathways) screening in a cell imaging platform. In CNG-bearing cells simultaneously labeled with both calcium and membrane potential dyes, activation of Gs-coupled GPCRs will trigger sustained signals in both calcium and membrane potential read-outs. In contrast, activation of Gq-coupled receptors will induce a rapid and transient calcium rise (due to release of intracellular calcium stores) with no effect on the membrane potential. Gi-coupled GPCRs will induce neither signal. Hence, Gs and Gq receptors can be easily distinguished.

Addition of a first compound known to increase cAMP levels, such as isoproterenol (a known Gs-coupled GPCR agonist) or forskolin (a known activator of adenylate cyclase, AC, the enzyme synthesizing cAMP) will result in a sustained signal measurable by at least one of a membrane potential dye, or an ion-sensitive dye (such as calcium a calcium sensitive dye). However, such cells in which a Gi-coupled GPCRs has also been activated will exhibit a reduced response (due to inhibition of AC by Gi) which is reflected in at least one of the membrane potential dye, or the ion-sensitive dye. Hence, the present invention provides for a single assay in which Gs, Gq or Gi receptors can be detected. Such an assay further allows for identification of the coupling specificity of a receptor.

Assays of the present invention also provide for the sequential screening of at least a second receptor. For example, a first compound may be found to induce a Gq-coupled receptor as indicated by transient increase in intracellular calcium. Subsequent addition of a second ligand may be seen to induce prolonged responses in both calcium and membrane potential, indicative of a Gs receptor. In yet a further addition, a third ligand-could be seen to have no effect. However, simultaneous addition of forskolin and the third ligand also fails to induce an increase in at least one of membrane potential or calcium signals, whereas addition of forskolin alone does increase in at least one of membrane potential or calcium signals, indicative of a Gi receptor. Hence, the present invention enables multiple assays on single samples.

Further still, the present assay can be multiplexed with other assays to substantially increase the information content. This increases the throughput, reduces material requirements, and provides a basis for prioritizing lead compounds. For example, such assays might include, but are not limited to, the simultaneous assay of apoptosis (using the ratio dye JC1 for detection of changes in mitochondrial membrane potential), thereby providing initial information on the toxicity of particular compounds or classes of compounds. Further, the present invention can be performed simultaneously with redistribution assays where a protein of interest could be tagged with a fluorescent protein, luminescent protein, etc.

The components of multiplexed assays can also be performed sequentially in any order. For example, for Gq-GPCRs, the first transient calcium response will be followed by a sustained Gs-mediated calcium and membrane potential signal. For Gs-GPCRs, the first calcium and membrane potential response will be either not affected (in the case that the preceding ligand exhibited maximal potency/efficacy toward the CNG-mediated signaling) or further enhanced.

The novel calcium-insensitive CNG mutations of the invention exhibit high and homogenous expression in engineered cells (virtually 100% of the cells within newly generated clones bearing mutated CNG respond reproducibly to Gs-coupled agonists of endogenous receptors without showing adverse effects). The new mutations provide a long sought means for the measurement of real-time, live cell cAMP responses in experimental models wherein the biological substrate is represented by cells that are few in number and costly to produce, such as primary cell cultures. Primary cells are a highly valuable biological substrate for they are the closest model to in vivo physiological conditions and offer the best environment for the study of a number of critical pathways involved in physiologically relevant processes, such as cell differentiation, diseases, and cancer. However, due to their limited life span in vitro, they need to be originated frequently from animal organs. The limited time frame within which primary cells can be used together with the known resistance that these cells exhibit toward conventional transfection procedures, requires the transient transfection/infection of the gene of interest (in this case, CNG) to be maximally effective. The new mutations offer an advantage in this respect. Thus, relevant primary cells may be engineered to express CNG for the study of live cell cAMP responses mediated by endogenous receptors signaling through cAMP as well as for the study of real time, live cell crosstalk between second messenger pathways (defects in receptor signaling and transduction pathway interplays could be affected in a disease state only reproducible in primary cells).

The use of primary cells as biological substrates provides for the possibility to run cell imaging-based assays with a limited number of cells, without loss of sensitivity and statistical significance. Compared to whole-well plate reader-based assays where a high number of cells are needed to generate a detectable signal (e.g., >50,000 cells in a single well of a 96-well plate), cell imaging requires a much smaller number of cells (<5,000). This is because (a) cell imagers include more sensitive excitation/emission devices than those found in standard plate readers and thus single cell-generated signals are readily detectable, and (b) each and everyone of the cells within the imaging field is considered as a separate entity thus providing a statistically significant pool for data analysis (for example: up to 200-300 cells can be contained in a 20× microscopic field being measured).

With the improved sensitivity of the new CNG cell-line and assay reagents, it should be possible to work with fewer and fewer cells and still generate sufficient signal for visualization. Use of 1536 well plates using the new constructs will further enable this assay format. Microfluidic devices may be used that allow cells to be perfused with an agonist/antagonist/allosteric modulator in a format that generates fluorescence output that is, in turn, read by a fluorescence reader configured to the microfluidic format. Similarly, it should be possible to visualize localized activation of cells harboring specific GPCRs in a lawn of cells arrayed on a solid substrate that is compatible with fluorescence imaging.

The assays of the present invention also provide mutiplexing potential where other dyes are used to monitor different parameters. Optical compatibility among the probes is the only limitation in combining multiple fluorescent probes. Useful combinations could include probes for cytotoxicity detection and apoptosis induction. A variety of probes with various fluorescence properties are available for this purpose. Multiplexing CNG-based GPRC screens with assays that identify in the very early phase of drug discovery unwanted effects of the candidate drug has become a highly desirable approach to accelerate the finding and profiling of potentially successful drugs.

GPCR/CNG Assays

In these assays the GPCRs and CNG channels may be endogenous to the cells or may be exogenously supplied, for instance in the case of the novel CNG mutants described herein. In addition, endogenous or exogenously supplied G proteins, including promiscuous G proteins, may be used in the assays and methods of the invention.

In some embodiments, the present invention provides a host cell that contains a first nucleic acid comprising a first promoter operably linked to a first polynucleotide wherein the polynucleotide comprises a sequence encoding a G protein-coupled receptor (GPCR) protein and a second nucleic acid comprising a promoter operably linked to a second polynucleotide wherein the second polynucleotide comprises a sequence encoding a cyclic nucleotide-gated (CNG) channel. In some embodiments, the cyclic nucleotide-gated channel comprises at least one mutation that makes the channel more sensitive to cAMP than a channel that does not comprise the mutation. In some embodiments, the GPCR and/or the CNG channel is not normally expressed in the cell. The nucleic acids may be part of one molecule or may be parts of different molecules. The nucleic acids may be provided to the cell in any formulation known to those skilled in the art, for example, one or both of the nucleic acids may be part of a virus and/or plasmid and/or may be expressed from the genome of the cell.

In some embodiments, it may be desirable to utilize or create a cell line that expresses one or more of the molecules from the genome of the cell. The creation of stable cell lines for the expression of proteins is within the capability of one ordinarily skilled in the art. Some embodiments of the present invention may include expressing one protein from the genome of the cell and the other from an exogenous nucleic acid, preferably a virus or a plasmid. Cells of the present invention may be any kind of cell but are preferably eukaryotic cells such as mammalian cells. Examples of cells suitable for the practice of the present invention include, but are not limited to, BHK cells, mouse L cells, Jurkat cells, 153DG44 cells, HEK cells, CHO cells, PC12 cells, human T-lymphocyte cells and Cos-7 cells.

The CNG channels used in the present invention may be wildtype channels or may be mutated to make them more responsive to cAMP. The wildtype CNG channels of the present invention may be homomeric or heteromeric. The channels may comprise one or more mutations that make the channel more sensitive to cAMP than a channel that does not comprise the mutations. Channels that comprise two or more mutations that make the channel more sensitive to cAMP than a channel that does not comprise the mutations are also included in the present invention. Channels that comprise three or more mutations that make the channel more sensitive to cAMP than a channel that does not comprise the mutations are also included in the present invention. Nucleic acid molecules encoding CNG channels of the invention may comprise all or part of one or more of the nucleic acid sequences provided as SEQ ID NOS: 1, 5, and 7. Some CNG channel proteins of the present invention may comprise all or part of one or more of the protein sequences provided as SEQ ID NOS: 2, 4, 6, and 8.

In some embodiments, the CNG channels used in the present invention may be responsive to cGMP. In other embodiments, the CNG channels used in the present invention may be responsive to analog or derivative cyclic purine monophosphates (cPuMP) or cyclic nucleotide monophosphates (cNMP). In still other embodiments, a CNG channel used in the present invention may be responsive to only one of cAMP, cGMP, an analog or derivative cPuMP or a cNMP. In a preferred embodiment, a CNG channel used in the present invention may be responsive to at least one of cAMP, cGMP, an analog or derivative cPuMP, or a cNMP. In yet another preferred embodiment, a CNG channel used in the present invention may be responsive to two or more of cAMP, cGMP, an analog or derivative cPuMP, or a cNMP.

The nucleic acid molecules encoding GPCRs according to the present invention may encode a full length wildtype G protein-coupled receptor or may encode a mutant GPCR. Some preferred mutants include N- and C-terminal truncations and insertion and/or deletion mutants. Other preferred mutants may have at least one conservative or non-conservative amino acid base substitution. Still other preferred mutants may have a combination of mutations, comprising at least two selected from the group consisting of N-terminal truncations, C-terminal truncations, insertions, deletions, conservative amino acid base substitutions and non-conservative amino acid base substitutions. A mutant GPCR is suitable for use in the present invention if it is capable of inducing a GPCR-mediated activity when contacted with an agonist.

In some embodiments, cells of the present invention may contain a third nucleic acid comprising a third promoter operably linked to a third polynucleotide wherein the third polynucleotide comprises a sequence encoding a G protein. The G protein may be a promiscuous G protein. The G protein may be normally expressed in the cell but may be expressed at a higher level when the cell contains the third nucleic acid. Alternatively, the G protein may not be naturally expressed in the cell.

In some embodiments of the invention, the G protein-coupled receptor is substantially coupled to at least one G protein selected from the group consisting of $G\alpha_s$, $G\alpha_i$, $G\alpha_{16}$ or $G\alpha_q$, and promiscuous G proteins. Alternatively, the G protein-coupled receptor may be substantially coupled to a hybrid G protein, such as $G\alpha_{qs}$, for example.

It has been shown that the C-terminal 4-5 amino acids of Gα proteins encodes the domain mediating interaction with the receptor (Conklin et al 1993. Nature 363:274-276). Chimera Gas proteins in which the C-terminus of Gαi proteins replaces that of a Gαs (Gαs/i) have been shown to couple to Gi receptors, and stimulate the activity of adenylyl cyclase (Komatsuzaki et al., 1997. FEBS Letters 406:165-170). The use of certain chimeric Gα proteins in screening orphan G-protein coupled receptors is known in the art. In particular, assays are available that utilize chimeric Gαqs to direct the coupling of a Gs receptor through a Gq pathway, allowing a Gs receptor to be monitored by release of intracellular calcium. Similar assays exist for converting Gi receptors to Gq using chimeric Gαqi. A major limitation to the use of chimeric Gαq is that such assays provide only transient release of calcium. This restricts the throughput potential, and limits the extent of miniaturization possible. The use of Gαsi chimeras for screening GPCRs is also known. In radioimmunoassays, increases in cAMP levels can be detected, however, these show relatively low signal to noise ratios. Both radioimmunoassays and transcription reporter assays often required prolonged incubation with ligand. (Drew et. al., 2002. BBA 1592:185-192).

In contrast, the current invention enables efficient use of Gαsi chimeras. In particular, the current invention provides a prolonged signal that allows for either kinetic or end point assays. In a preferred embodiment, the described invention is practiced in a multi-well plate. Standard formats include 96 well, 384 wells or 1536 wells. The disclosed invention, using intact live cells and examining cAMP levels at a single-cell level, is particularly suited for 1536 well formats. Said assays can be miniaturized to plates containing at least 1536 wells, thereby substantially reducing reagent cost, the number of cells necessary to perform the assay, and increases the throughput speed.

In standard cAMP assays, cells are lysed and total cAMP is measured by antibodies, or any of a number of other methods known well to those skilled in the art. The signal and dose-response characteristics of lysed-cell assays are dependent on cell number in each well. The assay sensitivity decreases with decreasing cell number. In contrast, because the current invention measures cAMP levels within single live cells, the signal (F/Fb, fluorescence fold-change) and dose-response characteristics vary little with decreasing cell number, providing detector settings are optimized. Intracellular concentration of free cAMP is independent of cell number in the CNG channel-based cAMP assay. This capability has substantial value, particularly when the invention is used in screening of libraries of pharmaceutical compounds, as it substantially increases the throughput, and decreases the amount of materials required for each assay (cost). This is particularly true when the cells being examined are difficult to obtain, such as in primary cells or tissue.

It will be apparent to those skilled in the art that it is of great utility and value that the current invention enables further reduction in the number of cells being examined, down to the single cell, and it is envisioned that screening formats with larger numbers of wells, including volumes permitting at least one cell per well, are possible. Further, the cells need not be confined to wells, rather arrays of at least one cell per feature, are envisioned. Consequently, screening formats are envisioned wherein arrays comprising hundreds, thousands, or tens of thousands of features, each feature comprising at least one cell, wherein the at least one cell expresses at least one endogeneous or heterologous receptor, and wherein the receptors expressed at each feature can be the same or different.

Moreover, the cells need not be arrayed. It is further envisioned that single cells positioned randomly, wherein the at least one cell expresses at least one endogeneous or heterologous receptor, and wherein the receptors expressed at each feature can be the same or different, are identified as having altered cAMP levels as a result of a perturbation. In certain instances, it is sufficient to know that at least one cell, in a mixture of cells, is responding to a particular perturbation. As used herein, the term "perturbation" refers to any environmental change that can alter the biological activity of a cell. Exemplary perturbations include, but are not limited to, any combination of one or more of chemical, biological, mechanical, thermal (e.g., heat shock, and the like), electromagnetic, gravitational, nuclear, or temporal factors, for example. It will be appreciated that the format in which the cells are assayed by the present invention is flexible regardless of the type of perturbation. In particular, for screening compounds in the pharmaceutical industry, any of the described formats can be used for agonists, antagonists, allosteric modulators, partial agonists, partial antagonists and the like.

In cases where the identity of a receptor in a responding cell within a population of nonresponding cells is of interest, the responding cells can be examined directly for the identity of the receptor using antibodies, PCR or other methods known to those in the art, or the cells can be isolated, using lasers for example, further propagated and characterized for the identity of the responding receptor. The assays of the invention are suitable for characterizing any unknown proteins that participate in the signaling pathway of interest, providing means for deorphanizing G-protein linkages and identifying cyclases that are activated or inhibited by particular G proteins, for example. For instance, using RNA interference and specifically small interfering RNAs (siRNAs) corresponding to candidate G proteins and cyclases, the different G proteins and cyclases may be selectively inhibited within cells during the assay, thereby permitting one to characterize the effects of up or down regulation of these and other players, on cAMP production.

Further still, the present invention allows for detection of either cation influx (e.g., calcium) or membrane potential changes, providing methods of monitoring that are compatible with existing pharmaceutical screens. Therefore, in a preferred embodiment, among others, the present invention enables the high-throughput screening of cAMP concentration changes in cells that also express a chimeric G alpha protein. Such chimeric alpha proteins can include, but are not limited to, Gαsi proteins. In another preferred embodiment, at least one of the chimeric alpha, and the CNG of the current invention is stably integrated into the chromosome of the host cell. Said host cell expressing at least one of an endogeneous and a heterologous GPCR. In yet another preferred embodiment, the chimeric alpha protein is covalently linked to the GPCR.

In another aspect, the present invention provides a method of detecting activity of a GPCR by expressing the GPCR in a cell-optionally from an exogenous or heterologous GPCR-encoding nucleic acid molecule-expressing a cyclic nucleotide-gated channel that may comprise one or more mutations that make the channel more sensitive to cAMP; and measuring activity of the channel wherein activity of the channel indicates activity of the GPCR. The CNG channel may be expressed from an exogenous nucleic acid or from the genome of the cell.

In some embodiments, measuring may entail the use of a dye, for example, a fluorescent dye that can be detected by fluorescence imaging systems. Some preferred dyes include, but are not limited to, $Ca^{2+}$ sensitive dyes and voltage sensitive dyes, in formats involving small organic molecules and genetic encoded protein molecules. In some embodiments, measuring may entail determination of activation of CNG channel activity in a single cell. This may be accomplished using any means known to persons skilled in the art such as by fluorescence detection using a microscope or FACS (Fluorescence Activated Cell Sorting). When a microscope is used it may be desirable to couple the microscope to a computer system. The computer system may be used to track individual cells and perform statistical analysis.

Non-dye indicators may also be employed in any of the assays described herein. For example, GFP-based indicators exist for measuring membrane potential. Aequroin proteins produce light as an indication of calcium influx. Other indicators are known and available for measuring other cations, such as sodium and potassium. Accordingly, the present invention may be performed using any appropriate indicator substance, including, for example, fluorescent and luminescent indicators.

In some embodiments, the method may be configured to be conducted in a multiwell plate—96 well, 384 well etc.—and measuring may be performed with a multiwell microplate reader. Examples of suitable readers include those that are fluorometric-based readers with a CCD camera and fluorometric-based scanning microplate readers.

In some embodiments, it may be desirable to attach the cells to a solid surface before, during or after performing the methods of the invention. Suitable solid surfaces include, but are not limited to, slides and multiwell plates.

In some instances it may be desirable to increase the sensitivity of the methods of the invention. This may be accomplished by, for example, pretreating the cells with a cAMP analogue before measuring. Suitable analogues include caged photoactivatable analogues.

The methods of the invention may be practiced with cells expressing a promiscuous G protein. The promiscuous G protein may be expressed from the genome of the cell and/or may be expressed from an exogenous nucleic acid.

In some embodiments of the invention, the GPCR-mediated activity to be measured may be ion flux. In these cases, ion flux may be measured by any method known to those skilled in the art including, but not limited to, by determining a change in spectral characteristic of a dye or by patch clamp.

In another aspect, the present invention provides a method of identifying a ligand for a receptor by contacting a cell with a compound wherein the cell expresses the receptor and at least one cyclic nucleotide-gated (CNG) channel and measuring activation of the CNG channel, wherein activation of the CNG channel indicates that the compound is a ligand for the receptor. In some embodiments, the receptor may not be endogenous to the cell and/or the CNG channel may be engineered to increase the channel sensitivity to cAMP. The CNG and/or the GPCR channel may be expressed from an exogenous nucleic acid and/or from the genome of the cell. Measuring of the CNG channel activation may be by any means known to those skilled in the art including, but not limited to, by the use of a dye. An example of a suitable dye is a fluorescent dye that can be detected by imaging systems. Preferably a dye may be a $Ca^{2+}$ sensitive dye and/or a voltage sensitive dye.

The methods of identifying a ligand may be used on a single cell by measuring activation of CNG channel activity in a single cell. Methods of this type may employ the use of fluorescence detection using a microscope. When a microscope is used, it may be desirable to couple the microscope to a computer system. The computer system may be used to track individual cells and perform statistical analysis.

The methods of identifying a ligand may be used in a multiwell—96 well, 384 well, 1536 well, etc—format and measuring may be performed with a microplate reader. A suitable reader may be a fluorometric-based reader with a CCD camera and/or a fluorometric-based scanning microplate reader.

The methods of identifying a ligand may be used with cells attached to a solid surface. The cells may be attached before, during or after performing one or more of the method steps. Suitable solid surfaces include, but are not limited to, slides and multiwell plates.

The methods of the invention may also be performed on non-adherent cells, for instance using fluorescence activated cell sorting (FACS) analysis. Protocols using FACS to monitor $[Ca^{2+}]i$ and membrane potential of cells are well established and can be easily adopted to monitor CNG channel activity (Lazzar et al., 1986, *J Biol Chem,* 261:9710-9713; Shapiro, 2000, *Methods,* 21:271-279).

The methods of identifying a ligand may be used with cells that have been pretreated with a cAMP analogue before being contacted with the ligand, for example, with a caged, photo-activatable analogue.

The methods of identifying a ligand may be used with one or more cells that express a promiscuous G protein.

In some embodiments, the methods of identifying a ligand may include a measuring step that comprises determining ion flux. Ion flux may be determined by any means known to those skilled in the art such as by a change in spectral characteristic of a dye and/or by patch clamp.

In another aspect, the present invention provides a method of identifying an agent that modulates an activity mediated by a GPC receptor by contacting a cell with the agent and a ligand for the receptor wherein the cell expresses the receptor and at least one cyclic nucleotide-gated (CNG) channel including wildtype or CNGs engineered to increase the channel sensitivity to cAMP and measuring activation of the CNG channel. In some embodiments, it may be desirable to compare activation of the CNG channel in the presence of the agent to activation of the channel in the absence of the agent. Typically, a difference in activation of the CNG channel indicates the agent modulates the activity. The CNG channel may be expressed from an exogenous nucleic acid and/or from the genome of the cell. Measuring the activation of the CNG channel may entail the use of a dye. An example of a suitable dye is one that is a fluorescent dye that can be detected by UV-based imaging systems. Dyes may be $Ca^{2+}$ sensitive dyes and/or voltage sensitive dyes. Dyes of the present invention may be added exogenously to the cells either before or during the assay. Alternatively, dyes of the present invention may be expressed exogenously by the cells as probes. Said probes may be introduced into said cells for transient expression or for stable expression.

The methods of identifying an agent that modulates an activity mediated by a GPC receptor may be practiced on a single cell by determination of activation of CNG channel activity in a single cell. Methods of making such a determination are known to those skilled in the art and include by UV-based fluorescence using a microscope. When a microscope is used it may be coupled to a computer system. The computer system may be one that tracks individual cells and performs statistical analysis.

The methods of identifying an agent that modulates an activity mediated by a GPC receptor may be configured to use a multiwell—96 well, 384 well etc—format. Configurations of this type may employ a multiwell microplate reader, for example, a fluorometric-based reader with a CCD camera and/or a fluorometric-based scanning microplate reader.

The methods of identifying an agent that modulates an activity mediated by a GPC receptor may be practiced on cells attached to a solid support. The cells may be attached before, during or after performing one or more method steps. Suitable solid supports include slides and multiwell plates.

The methods of identifying an agent that modulates an activity mediated by a GPC receptor may be performed using cells pretreated with a cyclic nucleotide analogue. Suitable analogues include caged, photoactivatable analogues.

Any of the methods of identifying an agent that modulates an activity mediated by a GPC receptor may be practiced using cells that express a promiscuous G protein.

The present invention further provides kits adapted to perform the methods of the invention. Such kits will typically include one or more cells of the invention in a suitable container. Kits may optionally comprise one or more reagents such as buffers and/or salts and/or dyes. When dyes are included, they will typically be voltage sensitive dyes and/or $Ca^{2+}$ sensitive dyes.

A. Definitions

In the description that follows, numerous terms and phrases known to those skilled in the art are used. In the interest of clarity and consistency of interpretation, the definitions of certain terms and phrases are provided.

As used herein, "fluorescence quenching" refers to any process which decreases the fluorescence intensity of a sample. General teaching can be found, e.g., in "Principles of Fluorescence Spectroscopy" (Joseph R. Lakowicz, 1983, $1^{st}$ edition, Kluwer Academic/Plenum Publishers, New York). Several ways have been described to quench fluorescence as follows:

1. Collisional quenching involving collisions with other molecules that result in the loss of excitation energy as heat instead of as emitted light. This process is always present to some extent in solution samples; species that are particularly efficient in inducing the process are referred to as collisional quenchers (e.g. iodide ions, molecular oxygen, nitroxide radical).
2. Static quenching. Interaction of the fluorophore with the quencher forms a stable non-fluorescent complex. Since this complex typically has a different absorption spectrum from the fluorophore, the presence of an absorption change is diagnostic of this type of quenching (by comparison, collisional quenching is a transient excited state interaction and so does not affect the absorption spectrum). A special case of static quenching is self-quenching, where fluorophore and quencher are the same species. Self-quenching is particularly evident in concentrated solutions of tracer dyes.
3. Resonance energy transfer. Like collisional quenching, this is an excited state interaction but the two participating molecules do not have to collide—it can occur over distances of 100 angstroms or more. One dye (the donor) is excited by absorption of a photon, but instead of emitting a fluorescence photon, the excitation is transferred by electronic coupling to an acceptor molecule. The result of this exchange is an excited acceptor and a ground state donor. In signal terms the result is either fluorescence at longer wavelength (compared to the spectrum of the donor alone) or no fluorescence, depending on whether the acceptor is itself fluorescent or non-fluorescent.
4. Inner filter effect. This is a measurement artifact as opposed to a quenching process. It occurs in samples with very high absorbance (the absorbance can be due to the fluorophore itself or other absorbing components of the sample—it doesn't matter which). Under these conditions, all of the incident exciting light is absorbed at the front face of the sample. In a conventional 90 degree detection geometry, the excitation light cannot penetrate deeply enough to the point at which the detection optics are focused. The result is the detected fluorescence decreases as the sample absorbance increases. As implied, the magnitude of inner filter effect depends on the geometrical relationship between the excitation and emission detection paths and on the thickness of the sample. To avoid inner filter effects (and other artifacts), it is generally advisable for the sample absorbance measured at the excitation wavelength to not exceed 0.1.

As used herein, "substantially interacts" refers to the amount of an effect one molecule has on another, for example, the effect of a GPCR on a G protein. An interaction is substantial if it results in a detectable response of an amplitude capable of having a physiological effect.

As used herein, the "genome" of a cell refers to the genetic material contained on the chromosomes of the cell.

As used herein, "GPCR-mediated activity" refers to any cellular process that can be affected by signal transduction mediated by a GPCR. This phrase is seen to include, but is not limited to cyclic nucleotide production, $Ca^{2+}$ influx, inositol triphosphate ($IP_3$) and diacylglycerol production and the like.

In some instances, putative GPCRs may be identified by homology to other known GPCRs. Homology or identity at the nucleotide or amino acid sequence level is determined by BLAST (Basic Local Alignment Search Tool) analysis using the algorithm employed by the programs blastp, blastn, blastx, tblastn and tblastx (Altschul et al., *Nucleic Acids Res* 25: 3389-3402, 1997 and Karlin et al., *Proc Natl Acad Sci USA* 87:2264-2268, 1990, both fully incorporated by reference) which are tailored for sequence similarity searching. The approach used by the BLAST program is first to consider similar segments, with and without gaps, between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al. (*Nature Genetics* 6:119-129, 1994) which is fully incorporated by reference. The search parameters for histogram, descriptions, alignments, expect (i.e., the statistical significance threshold for reporting matches against database sequences), cutoff, matrix and filter (low complexity) are at the default settings. The default scoring matrix used by blastp, blastx, tblastn, and tblastx is the BLOSUM62 matrix (Henikoff et al., *Proc Natl Acad Sci USA* 89:10915-10919, 1992, fully incorporated by reference), recommended for query sequences over 85 in length (nucleotide bases or amino acids).

For blastn, the scoring matrix is set by the ratios of M (i.e., the reward score for a pair of matching residues) to N (i.e., the penalty score for mismatching residues), wherein the default values for M and N are +5 and −4, respectively. Four blastn parameters were adjusted as follows: Q=10 (gap creation penalty); R=10 (gap extension penalty); wink=1 (generates word hits at every $wink^{th}$ position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

As used herein, "stringent conditions" are those that (1) employ low ionic strength and high temperature for washing, for example, 0.015 M NaCl/0.0015 M sodium citrate/0.1% SDS at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is hybridization in 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC and 0.1% SDS. A skilled artisan can readily determine and vary the stringency conditions appropriately to obtain a clear and detectable hybridization signal. Preferred molecules are those that hybridize under the above conditions to the complement of SEQ ID NO: 1, 3, and which encode a functional protein. Even more preferred hybridizing molecules are those that hybridize under the above conditions to the complement strand of the open reading frame of SEQ ID NO: 1, 3.

As used herein, a nucleic acid molecule is said to be "isolated" when the nucleic acid molecule is substantially separated from contaminant nucleic acid molecules encoding other polypeptides.

The present invention further provides fragments of the encoding nucleic acid molecule. As used herein, a fragment of an encoding nucleic acid molecule refers to a small portion of the entire protein coding sequence. The size of the fragment will be determined by the intended use. For example, if the fragment is chosen so as to encode an active portion of the protein, the fragment will need to be large enough to encode the functional region(s) of the protein. For instance, fragments that encode peptides corresponding to predicted antigenic regions may be prepared. If the fragment is to be used as a nucleic acid probe or PCR primer, then the fragment length is chosen so as to obtain a relatively small number of false positives during probing/priming.

Fragments of the encoding nucleic acid molecules of the present invention (i.e., synthetic oligonucleotides) that are used as probes or specific primers for the polymerase chain reaction (PCR), or to synthesize gene sequences encoding proteins of the invention, can easily be synthesized by chemical techniques, for example, the phosphotriester method of Matteucci et al. (*J Am Chem Soc* 103, 3185-3191, 1981) or using automated synthesis methods. In addition, larger DNA segments can readily be prepared by well-known methods, such as synthesis of a group of oligonucleotides that define various modular segments of the gene, followed by ligation of oligonucleotides to build the complete modified gene.

Cyclic nucleotide-gated (activated) ion channels are most well known for mediating visual and olfactory signal transductions, but they are also expressed in other cell types and tissues. In native tissues, these channels are heteromultimers, with different heteromers showing distinct nucleotide sensitivity, ion conductance (selectivity), and $Ca^{2+}$ modulation. Molecular cloning and genome sequencing efforts have revealed the presence of six genes coding for subunits of cyclic nucleotide-gated channels in human and mouse. The adopted nomenclature for these channel subunits recognizes two phylogenetically distinct subfamilies, CNGA and CNGB, defined by their sequence relationships. The CNGA subfamily comprises CNGA1 (CNG1/CNGα1/RCNC1); CNGA2 (CNG2/CNGα3/OCNC1); CNGA3 (CNG3/CNGα2/CCNC1); CNGA4 (CNG5/CNGα4/OCNC2/CNGB2). In the CNGB subfamily, the member expressed in rod photoreceptors, olfactory neurons and other tissues is designated CNGB1 (CNG4/CNGβ1/RCNC2 and a splice variant CNG4.3), whereas that found in cone photoreceptors and possibly other tissues is CNGB3 (CNG6/CNGβ2/CCNC2) (Bradley, J. et al., Nomenclature for ion channel subunits. Science. 2001 Dec. 7; 294:2095-6). It will be appreciated by those skilled in the art that channels derived from other organisms can be placed into the described subfamilies based on homology, and such channels are anticipated as applicable to the present invention.

As used herein, "mutant" or "mutated" CNG channels are those comprising subunits that have an altered amino acid sequence. Alterations of the amino acid sequence may include, but are not limited to, N-terminal truncations, C-terminal truncations, amino acid residue deletions or additions, conservative or non-conservative amino acid residue substitutions. A mutant CNG channel subunit may comprise one or more, two or more or three or more alterations to its amino acid sequence. A mutant CNG channel may be heteromeric, being composed of at least two different subunit types, such as α and β. A mutant CNG channel may be heteromeric in comprising subunits that have different mutations. A mutant CNG channel may be heteromeric in comprising at least one mutant subunit and at least one wildtype subunit. A mutant CNG channel may also be a heteromer comprising subunits corresponding to all of the wildtype subunits it is normally composed of when expressed in its native cell source, wherein at least one of those subunits comprises at least one alteration of its amino acid sequence. A mutant CNG channel may be composed of subunits derived from the same species as the recombinant cell transformed to express the CNG channel. A mutant CNG channel may be composed of subunits derived from a different species as the recombinant cell transformed to express the CNG channel. A mutant CNG channel may be composed of subunits derived different species. Mutant CNG channels may comprise subunits derived from any species, including, but not limited to, rat, murine, human, bovine, canine, feline, any other mammal or vertebrate, *Drosophila* and other insects, and *C. elegans*, for example.

As used herein, "wildtype" CNG channels are those composed of subunits that have not had mutations made to the amino acid sequence of those subunits as isolated from natural sources or subunits with mutations as compared to the subunit isolated from natural sources, wherein the mutations do not substantially alter channel function or activity. A wildtype CNG channel is preferably heteromeric, being composed of at least two different subunit types, such as α and β. A wildtype CNG channel may also include, in some preferred embodiments, a third different subunit. A wildtype CNG channel may also be a heteromer comprising all of the subunits it is normally composed of when expressed in its native cell source. A wildtype CNG channel may be composed of subunits derived from the same species as the recombinant cell transformed to express the CNG channel. A wildtype CNG channel may be composed of subunits derived from a different species as the recombinant cell transformed to express the CNG channel. A wildtype CNG channel may be composed of subunits derived different species. Wildtype CNG channels may also comprise subunits derived from any species, including, but not limited to, rat, murine, human, bovine, canine, feline, any other mammal or vertebrate, *Drosophila* and other insects, and *C. elegans*, for example. CNG channel subunits of the present invention may be present on a single or on multiple vectors for introduction into a host cell. For example, in the case of a wildtype α/β heteromeric CNG channel, the coding sequences for the α and β subunits may be contained on a single vector which is introduced into the host cell, or they may on separate vectors which are introduced into the host cell either separately or at the same time.

As used herein, "voltage sensitive dyes" or "membrane potential dyes" include those dyes that enter depolarized cells, bind to intracellular proteins or membranes and exhibit enhanced fluorescence. Voltage sensitive dyes include, but are not limited to, carbocyanine, rhodamine, oxonols, and merocyanine bis-barbituric acid oxonols. Voltage sensitive and membrane potential dyes also include probes which are encoded by nucleic acid sequences that can be incorporated into a vector for expression by a host cell.

As used herein, "calcium-sensitive dyes" include those dyes which exhibit enhanced fluorescence in response to increased levels of intracellular calcium. Calcium-sensitive dyes include, but are not limited to, Fura-2, Fluo-3, Fluo-4, and Calcium Green-1. Calcium-sensitive dyes also include probes which are encoded by nucleic acid sequences that can be incorporated into a vector for expression by a host cell and include, but are not limited to, Aeuorin (Euroscreen) and green fluorescent protein (GFP)-based calcium sensors such as Cameleon, for example.

B. Techniques

The present invention further provides recombinant DNA molecules (rDNAs) that contain a coding sequence. Preferred coding sequences are those that encode wildtype or mutant forms of one or more of GPCRs and/or G proteins and/or CNG channels. As used herein, a rDNA molecule is a DNA molecule that has been subjected to molecular manipulation in situ. Methods for generating rDNA molecules are well known in the art, for example, see Sambrook et al., (Molecular Cloning—A Laboratory Manual, Cold Spring Harbor Laboratory Press, Cold Spring Harbor, N.Y., 1989). In the preferred rDNA molecules, a coding DNA sequence is operably linked to expression control sequences and/or vector sequences.

The choice of vector and/or expression control sequences to which one of the protein encoding sequences of the present invention is operably linked depends directly, as is well known in the art, on the functional properties desired, e.g., protein expression, and the host cell to be transformed. A vector contemplated by the present invention is at least capable of directing the replication or insertion into the host chromosome, and preferably also expression, of the structural gene included in the rDNA molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

Expression vectors compatible with eukaryotic cells, preferably those compatible with mammalian cells, can be used to form rDNA molecules that contain a coding sequence. Eukaryotic cell expression vectors, including but not limited to viral vectors and plasmids, are well known in the art and are available from several commercial sources. Typically, such vectors are provided containing convenient restriction sites for insertion of the desired DNA segment. Typical of such vectors are pSVL and pKSV-10 (Pharmacia), pBPV-1/ pML2d (International Biotechnologies, Inc.), pTDT1 (ATCC, #31255), and the like eukaryotic expression vectors.

Eukaryotic cell expression vectors used to construct the rDNA molecules used in the present invention may further include a selectable marker that is effective in an eukaryotic cell, preferably a drug resistance selection marker. An example of a drug resistance marker is the gene whose expression results in neomycin resistance, i.e., the neomycin phosphotransferase (neo) gene (Southern et al., *J Mol Anal Genet* 1:327-341, 1982). Alternatively, the selectable marker can be present on a separate plasmid, and the two vectors are introduced by co-transfection of the host cell, and selected by culturing in the appropriate drug for the selectable marker.

The nucleic acid molecule is then preferably placed in operable linkage with suitable control sequences, as described above, to form an expression unit containing the protein open reading frame. The expression unit is used to transform a suitable host and the transformed host is cultured under conditions that allow the production of the recombinant protein.

Various mammalian cell culture systems can also be employed to express recombinant protein. Examples of mammalian expression systems include the COS-7 lines of monkey kidney fibroblasts, described by Gluzman (*Cell* 23:175, 1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements. Each of the foregoing steps can be done in a variety of ways. For example, the desired coding sequences may be obtained from genomic fragments and used directly in appropriate hosts. The construction of expression vectors that are operable in a variety of hosts is accomplished using appropriate replicons and control sequences, as set forth above. The control sequences, expression vectors, and transformation methods are dependent on the type of host cell used to express the gene and were discussed in detail earlier. Suitable restriction sites can, if not normally available, be added to the ends of the coding sequence so as to provide an excisable gene to insert into these vectors.

Other variants on expression vectors include fusion proteins between the gene of interest and other polypeptides. Applications include but are not limited to means of visualization (such as green fluorescent protein, GFP, and variants) or for protein purification (such as polyhistidine, or glutathione-S-transferase, GST).

Specifically contemplated are genomic DNA, cDNA, mRNA and antisense molecules, as well as nucleic acids based on alternative backbones or including alternative bases whether derived from natural sources or synthesized. Such nucleic acids, however, are defined further as being novel and unobvious over any prior art nucleic acid including that which encodes, hybridizes under appropriate stringency conditions, or is complementary to a nucleic acid encoding a protein according to the present invention.

The encoding nucleic acid molecules of the present invention may further be modified so as to contain a detectable label for diagnostic and probe purposes. A variety of such labels are known in the art and can readily be employed with the encoding molecules herein described. Suitable labels include, but are not limited to, biotin, radiolabeled nucleotides and the like. A skilled artisan can readily employ any such label to obtain labeled variants of the nucleic acid molecules of the invention.

Modifications to the primary structure of the nucleic acid molecules by deletion, addition, or alteration of the nucleotide sequence can be made without destroying the activity of the encoded proteins. Such substitutions or other alterations result in proteins having an amino acid sequence falling within the contemplated scope of the present invention.

II. Specific Embodiments

A. G Protein Coupled Receptors

At present, there are about 400 GPCR genes that can be identified from genomic databases, excluding odorant and taste receptors. Ligands for about 200 of these have been identified, leaving the rest as "orphan receptors". The key to uncover the potential of therapeutic benefits of agonists and/or antagonists of these orphan GPCRs is in the ability to identify the natural biological ligands for them to elucidate their biological functions and disease associations. For GPCRs whose ligand is known, the identification of agents that modulate a GPCR-mediated activity allows the development of pharmaceuticals with high affinity and desirable functionality against these receptors for the evaluation of their clinical potential (for a review, see, Debouck and Metcalf, 2000, *Annu. Rev. Pharmacol. Toxicol.* 40:193-208; Howard et al., 2001, *Trends Pharmacol. Sci.* 22:132-140).

B. Cyclic Nucleotide-Gated Channels

Cyclic nucleotide-gated (CNG) channels of vertebrates are cation channels controlled by the cytosolic concentration of cGMP and cAMP (for reviews, see Kaupp, 1995, *Curr. Opin. Neurobiol.* 5:434-442; Finn et al., 1996, *Annu. Rev. Physio.* 58:395-426; Zogotta and Siegelbaum, 1996, *Annu. Rev. Neurosci.* 19:235-263; Li et al., 1997, *Q. Rev. Biophys.* 30:177-193). These channels conduct cation currents, carried by mixed ions—$Na^+$, K+ and $Ca^{2+}$—and serve to couple both electrical excitation and $Ca^{2+}$ signaling to changes of intracellular cyclic nucleotide concentration. In vertebrate photoreceptors and olfactory sensory receptors, CNG channels depolarize the membrane voltage and determine the activity of a number of $Ca^{2+}$-regulated proteins involved in cell excitation and adaptation (for reviews, see Kaupp and Koch, 1992, *Annu. Rev. Physiol.* 54:153-175; Koch, 1995, *Cell Calcium* 18:314-321).

Figure 8A:
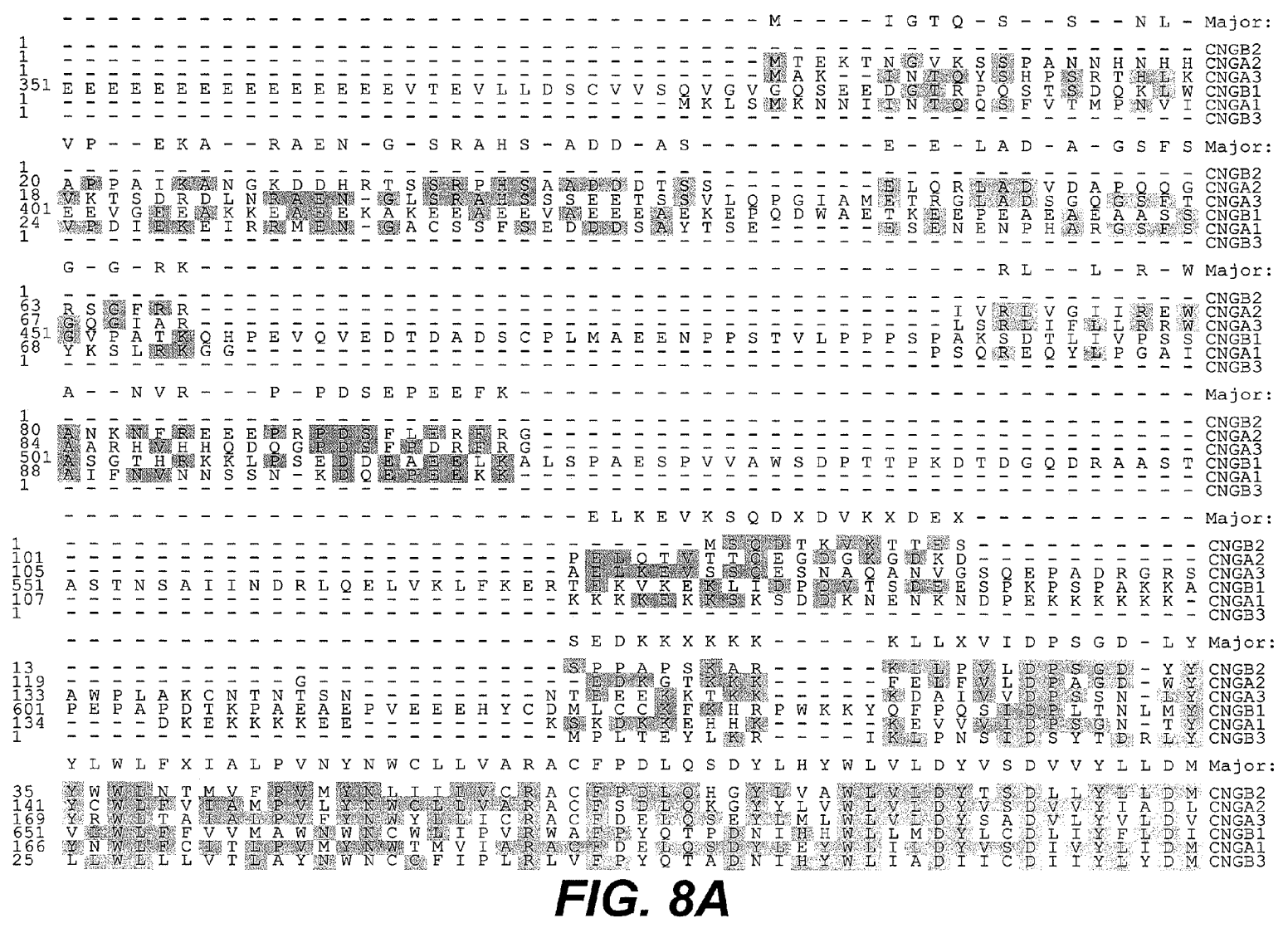
Figure 8B:
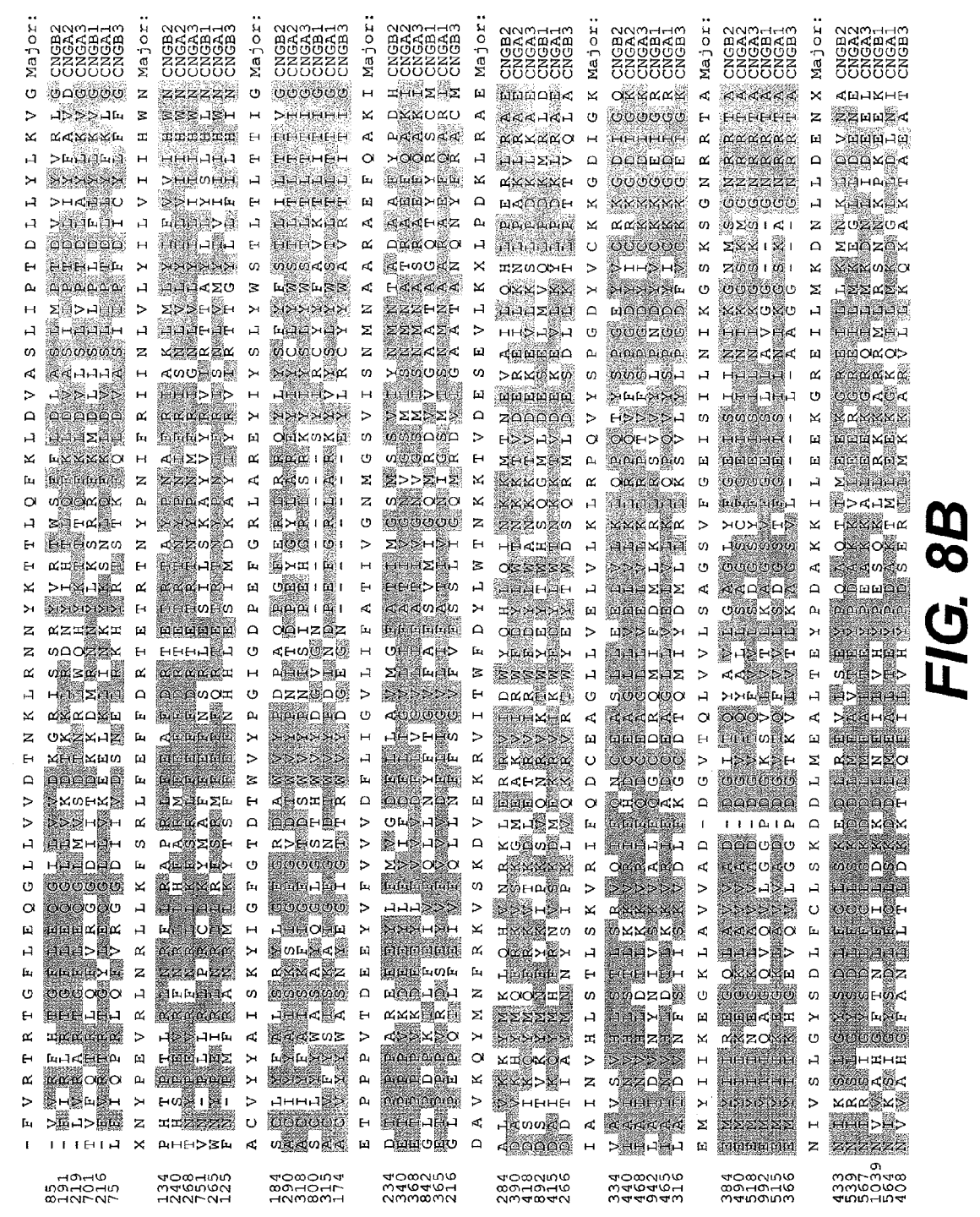
Figure 9A:
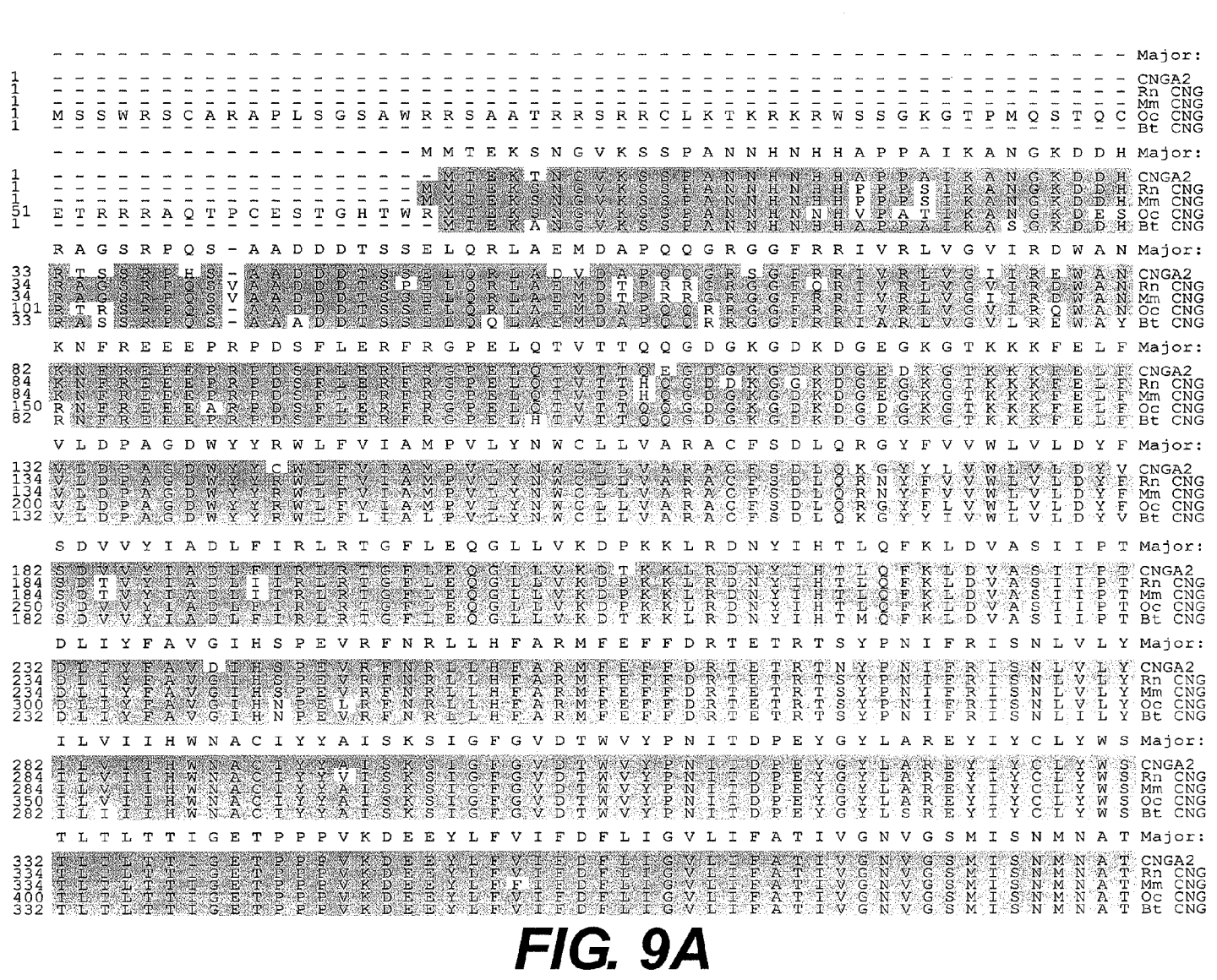
Figure 9B:
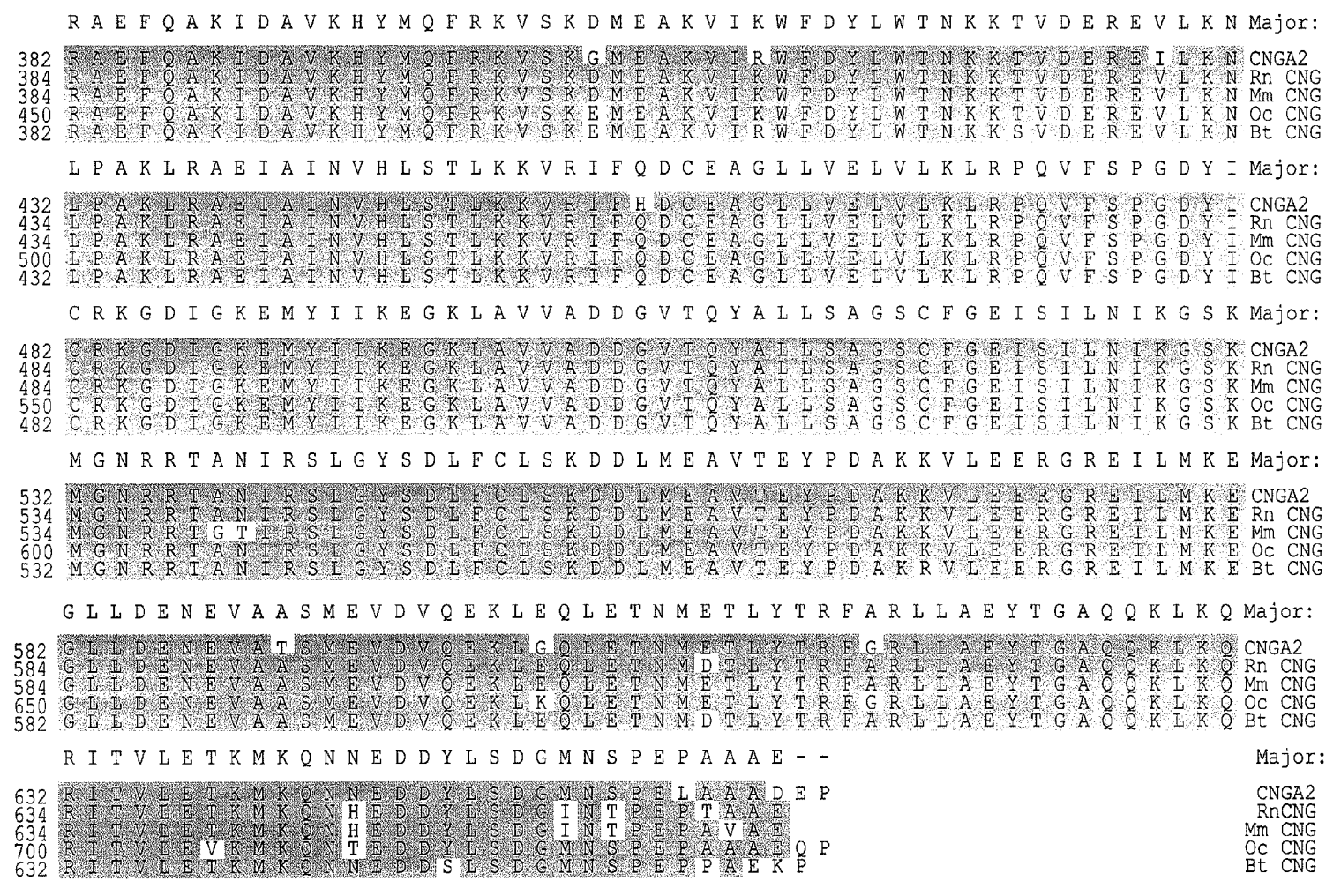

CNG channels are typically heteromultimers containing homologous $\alpha$ and $\beta$ subunits. Some CNG channels also have a third subunit as well. For example, a third subunit has been described for the rat olfactory CNG channel (GenBank Acc. No. AF068572). Although they are members of the voltage gated channel superfamily, they are not voltage sensitive, instead responding to changes in cyclic nucleotide concentration. Presently, six human genes have been identified that encode CNG channel subunits. An alignment of the human CNG channels is provided in FIG. 8 panels A-C. An alignment of several mammalian CNG channels is provided in FIG. 9 panels A and B.

CNG channel subunits typically consist of a cytoplasmic N-terminus, six membrane spanning segments and a cytoplasmic C-terminus. Between the fifth and sixth membrane spanning segments, a domain critical for pore lining—the P domain—has been identified. Various amino acid residues have been implicated in ion specificity and activation characteristics (see Gavazzo, et al., 2000, *J. Gen. Phys.* 116:311-15, Varnum, et al. 1995, *Neuron.* 15:619-625).

The rat olfactory CNG channel (CNGA2) forms cAMP-activated channels when heterologously expressed in mammalian cells with a half-maximally effective concentration (EC50) for cAMP of 68 µM (Dhallan et al 1990). When co-expressed with CNGB2, or CNGB2 and CNC$\beta$1b (GenBank accession number AF068572) EC50 for cAMP is reduced to 10.3 and 4 µM (Boenigk et al 1999). These wild type CNG channels can be used directly for monitoring activation of GPCRs by applying the methods disclosed herein. Wildtype CNG channels of the present invention may also include a third subunit, e.g., the third subunit of rat olfactory CNG channel (GenBank AF06572) or its equivalents in the rat or other species. However, mutants and chimeric constructs of the CNG channels can be used to further increase detectability of GPCR activation. Accordingly, the present invention includes both wildtype and CNG channels having one or more mutations in the following three regions: the cyclic nucleotide binding domain, the C-linker region and the $NH_2$ terminus that enhance the efficacy of cyclic nucleotide to open CNG channels (Altenhofen et al, 1991; Gordon & Zagotta, 1995; Varnum et al 1995; Zong et al, 1998; Paoletti et al 1999; Li & Lester, 1999; Shapiro et al, 2000; Scott et al 2000; Rich et al. 2001; Möttig et al 2001; and disclosed herein).

CNG channel subunits of the present invention may be present on a single or on multiple vectors for introduction into a host cell. For example, in the case of a wildtype α/β heteromeric CNG channel, the coding sequences for the α and β subunits may be contained on a single vector which is introduced into the host cell, or they may on separate vectors which are introduced into the host cell either separately or at the same time.

C. G Proteins

Many heterotrimeric G proteins have been cloned, including more than 20 genes encoding various G alpha subunits. The various G subunits have been categorized into six families, on the basis of amino acid sequences and functional homology. These six families are termed $G_s$, $G_i$, $G_q$, $G_{olf}$, $G_o$, and $G_{12}$. With the exception of $G_q$ that results in the release of cytoplasmic $Ca^{2+}$, all other G proteins mediate their signals through cyclic nucleotides, primarily cAMP (Watson and Arkinstall, The G-Protein-Linked Receptor Facts Book, Academic Press, London, 1994).

Certain G proteins are considered "promiscuous" G proteins because their G subunits allow them to couple with GPCRs that normally couple with G proteins of other families. For example, two members of the $G\alpha_q$ family, human $G\alpha_{16}$ and its murine homolog $G\alpha_{15}$ are promiscuous G proteins. Although G proteins having these G subunits interact with a variety of GPCRs, they still specifically activate their downstream effector. See U.S. Pat. No. 6,004,808 issued to Negulescu et al.

D. Adenylyl Cyclase

3',5' cyclic adenosine monophosphate (cAMP) is the archetypal second messenger in species from bacteria to man. cAMP is produced in mammals by a family of at least nine adenylyl cyclase (AC) isozymes. The mammalian ACs differ from one another in their activation or inhibition by Ca2+/calmodulin, phosphorylation by protein kinases A and C, the inhibitory G protein α subunit (Giα) and the G protein β and γ subunits (Gβγ). All mammalian ACs are activated by the GTP-bound stimulatory G protein α subunit (Gsα) and all but AC9 are activated by the hypotensive drug forskolin. The known mammalian ACs consist of 12 transmembrane helices and two cytoplasmic catalytic domains (Hurley, J. H., *Curr Opin Struct Biol*. 1998 December; 8(6):770-7).

In addition to their regulation by Gsα and forskolin, mammalian adenylyl cyclases are subjected to complex regulation by other G proteins, $Ca^{+2}$ signals, and phosphorylation. It is known that members of the Gi family (Gi, Go, Gz) that can be activated by diverse hormones and neurotransmitters (i.e., adenosine, epinephrine, and cannabinoid). On activation, the Gi family of proteins releases two potential regulators, Gα and Gβγ. Inhibition of adenylyl cyclase can be mediated through the α subunit of Gi, Go, or Gz or through Gβγ. For certain subtypes of adenylyl cyclases, such as type V and VI enzymes (predominantly expressed in heart), enzyme activity is inhibited by Giα and not altered by Gβγ.

The amount of a particular class of AC will vary between cell types. For this reason, and the above described differences in activation or inhibition, it will be appreciated that the properties of the present invention can be modified by further altering expression of at least a first adenylyl cyclase. Such alterations can include, but are not limited to, introduction of one or more heterologous ACs (both transiently expressed or integrated stably into the host genome; utilizing plasmid or viral vectors), or the up or down regulation of one or more endogeneous ACs. Methods for achieving said up or down regulation are many and known to those skilled in the art. The choice of the specific modulation is dependent upon the cell type, the G-protein linkage, the regulatory effects of various inhibitors or activators, and the means in which the present invention is to be applied.

E. Host Cells

The present invention further provides host cells that may be transformed with a nucleic acid molecule encoding one or more of a GPCR and/or G protein and/or CNG channel. Host cells can also include cells or cell lines which have an endogenous GPCR and/or G protein which can be used for methods of the present invention in combination with recombinant CNG channel expression. Preferred cells are eukaryotic cells. Eukaryotic cells useful for practicing the present invention include, but are not limited to, mammalian cells. Any cell may be used so long as the cell line is compatible with cell culture methods and compatible with the propagation of the expression vector and expression of the gene product. Preferred eukaryotic host cells include, but are not limited to, yeast, insect and mammalian cells, preferably vertebrate cells such as those from a mouse, rat, monkey or human cell line. Preferred eukaryotic host cells include Chinese hamster ovary (CHO) cells, for example those available from the ATCC as CCL61, NIH Swiss mouse embryo cells (NIH/3T3) available from the ATCC as CRL 1658, baby hamster kidney cells (BHK), mouse L cells, Jurkat cells, SF9, *Xenopus* oocytes, 153DG44 cells, HEK cells, PC12 cells, human T-lymphocyte cells and Cos-7 cells, and the like eukaryotic host cells.

Transfection of appropriate cell hosts with a rDNA molecule of the present invention is accomplished by well-known methods that typically depend on the type of vector used and host system employed. With regard to transformation of vertebrate cells with vectors containing rDNAs, electroporation, cationic lipid or salt treatment methods are typically employed, see, for example, Graham et al. (*Virol* 52:456, 1973) and Wigler et al., (*Proc Natl Acad Sci USA* 76: 1373-1376, 1979). Similarly, a number of options are commercially available including from Invitrogen/Life Technologies, Promega, Qiagen, etc.

Successfully transformed cells, i.e., cells that contain a rDNA molecule of the present invention, can be identified by well known techniques including the selection for a selectable marker. For example, cells resulting from the introduction of an rDNA of the present invention can be cloned to produce single colonies. Cells from those colonies can be harvested, lysed and their-DNA content examined for the presence of the rDNA using a method such as that described by Southern (*J Mol Biol* 98:503, 1975) or Berent et al. (*Biotech* 3:208, 1985) or the proteins produced from the cell assayed via an immunological method.

F. Assay Formats

The present invention provides various methods to assay for the presence and/or modulation of GPCR-mediated activity. In preferred embodiments, this may entail the detection of cAMP production by the activation of a CNG channel. In some embodiments, host cells of the present invention are assayed for the influx of $Ca^{2+}$ as a result of their activation by cAMP produced as the result of activation of a GPCR and transduction of the signal through the intermediacy of G proteins and adenyl cyclase to the production of cAMP.

In some embodiments, cells of the present invention may be loaded with a dye that responds to the influx of $Ca^{2+}$ with a change in one or more spectral qualities of the dye. In some embodiments, the dye binds $Ca^{2+}$ directly resulting in an observable change in spectral quality. One example of a dye of this type is fura-2.

In other embodiments, cells may be loaded with dyes that respond to the change in membrane-potential that results from the ion flux produced by the activation of the CNG channel. Dyes of this type are known to those skilled in the art (see, Zochowski, et al., 2000, *Biological Bulletin* 198:1-21) and are commercially available, for example, from Molecular Devices, Inc.

CNG channels were proposed as sensors for cAMP in assays aiming to detect $Ca^{2+}$ levels with the calcium sensitive dye Fura-2 (Rich et al, 2000, *J. Gen. Physiol.* 116:147-161). A large number of mutants of a CNG channel alpha subunit have been identified that include C460W (Gordon et al., 1997, *Neuron* 19:431-441), E583M (Varnum et al., *Neuron* 15, 619-925), and Y565A change (Li and Lester, 1998, *Mol. Pharmacol.* 55:873-882). While the mutants enhanced the CNG channel's sensitivity to cAMP, the improved sensitivities are still not sufficient for use in a multiwell format. In the best case so far reported, it required $3-4\times10^6$ cells for the elevated $Ca^{2+}$ level in response to cAMP induction to be detected by a spectrofluorimeter (Rich et al, 2001, *J. Gen. Physiol.* 118:63-77). In contrast, a typical multiwell assay will involve the use of about 20-50,000 cells per well which is about 100 fold fewer cells than required for $Ca^{2+}$ sensitive fluorescence dyes.

Voltage sensitive dyes that may be used in the assays and methods of the invention have been long used to address cellular membrane potentials (for review, see Zochowski et al., *Biol. Bull.* 198:1-21). Several classes of fluorescent dyes were developed that include carbocyanine, rhodamine, oxonols and merocyanine that can be obtained from Molecular Probes (Eugene, Oreg.). The three bis-barbituric acid oxonols, often referred to as DiBAC dyes, form a family of spectrally distinct potentiometric probes with excitation maxima at approximately 490 nm (DiBAC4(3)), 530 nm (DiSBAC2(3)) and 590 nm (DiBAC4(5)). The dyes enter depolarized cells where they bind to intracellular proteins or membranes and exhibit enhanced fluorescence and red spectral shifts (Epps et al., 1994, *Chem. Phys. Lipids* 69:137-150). Increased depolarization results in more influx of the anionic dye and thus an increase in fluorescence. DiBAC4(3) reportedly has the highest voltage sensitivity (Brauner et al., *Biochim. Biophys. Acta.* 771:208-216). Similar assays were developed for membrane potential assays in high throughput platforms such as FLIPR (Molecular Devices, Sunnyvale, Calif.). As cAMP also induces Na+ and K+ flux in addition to $Ca^{2+}$ changes of membrane potential as the result of Na+ and K+ flux in the presence of CNG channels can be used as the indicators of intracellular cAMP accumulation.

Detection of the alteration in the spectral characteristics of the dye may be performed by any means known to those skilled in the art. In preferred embodiments, the assays of the present invention are performed either on single cells using microscopic imaging to detect changes in spectral—i.e., fluorescent—properties or are performed in a multiwell format and spectral characteristics are determined using a microplate reader.

One suitable configuration for single cell imaging involves the use of a microscope equipped with a computer system. ATTO's Attofluor® RatioVision® real-time digital fluorescence analyzer from Carl Zeiss is a completely integrated work station for the analysis of fluorescent probes in living cells and prepared specimens (ATTO, Rockville, Md.). Calcium can be visualized in real time. The system can observe these ions either individually or simultaneously in combinations limited only by the optical properties of the probes in use. The standard imaging system is capable of performing multiple dye experiments such as Fura-2 (for calcium) combined with GFP (for transfection) in the same cells over the same period of time. Ratio images and graphical data from multiple dyes are displayed on line.

When the assays of the invention are performed in a multiwell format, a suitable device for detecting changes in spectral qualities of the dyes used is multiwell microplate reader. Suitable devices are commercially available, for example, from Molecular Devices (FLEXstation™ microplate reader and fluid transfer system or FLIPR® system). These systems can be used with commercially available dyes such as Fluo-3, Fluo-4, and Calcium Green-1. All of these indicators excite in the visible wavelength range.

The Molecular Devices' FLIPR Fluorometric Imaging Plate Reader (Molecular Devices, Sunnyvale, Calif.) has been used in a high throughput screening assay to detect transient calcium release from intracellular with a calcium sensitive fluorescent dye in response to the activation of the Gq coupled subclass of receptors that activate the phopholipase signaling pathway. Promiscuous G proteins were used for other GPCRs with mixed results. Until the present invention, there was no comparable assay for cAMP that produces real-time, kinetic information on GPCR receptor activation. Furthermore, there was no easy way to directly examine cAMP accumulation in single cell activated by GPCR ligand in live cells in an imaging platform.

In some embodiments of the present invention, the cells of the invention may be treated with compounds designed to increase the intracellular level of cAMP. For example, the cell may be treated with a "caged" cAMP analogue that can be released in response to photons of light. (see Corrie, et al. *Bioorganic Photochemistry* vol 2 pp 243-305, Wiley and Sons, Chichester, UK, and Hagen, et al, 1996, *Biochemistry* 35:7762-7771)

G. Methods to Identify Agents that Modulate GPCR-Mediated Activity

An additional embodiment of the present invention provides methods for identifying agents that modulate a GPCR-mediated activity. Agents that bind to the proteins involved in the activity or that affect the expression of these proteins may or may not affect the function of said proteins. Investigation of functional effects of agents includes but is not limited to: 1) effects on ligand binding, 2) effects on G protein coupled signaling pathways, 3) activation or inhibition of receptor down regulation/desensitization.

In one embodiment of the invention, the materials and methods described may be used to identify ligands for a GPCR. This embodiment will be useful to identify ligands for "orphan receptors" i.e., those receptors for which a ligand has yet to be identified. Ligands may be identified by contacting a cell of the invention with a compound that is a putative ligand. The cell may be transfected with a nucleic acid that expresses a GPCR of interest and optionally at least a nucleic acid that expresses a CNG channel, including one that has been mutated to increase its sensitivity to cAMP. Activation of the GPCR is assayed by measuring activation of the CNG channel. For example, a cell may be loaded with a calcium sensitive dye and/or a voltage sensitive dye and changes in the spectral characteristics of the dye in the presence and absence of the putative ligand may be determined. A compound is identified as a ligand if it induces opening of the CNG channel and a concomitant change in the spectral characteristics of the dye.

In another embodiment of the invention, the ability of an agent to modulate GPCR-mediated activity by, for example, altering ligand binding, may be determined. Alteration of ligand binding may be assessed by the ability of the agent being tested to modulate the binding of a known ligand for the target GPCR. This may be accomplished using the assays described above wherein the GPCR transfected into the cell has a previously identified ligand. Alternatively, an endogenous GPCR with an identified ligand may be used. The ability of the previously identified ligand to induce activity is assayed in the presence and absence of the agent. An agent modulates a GPCR-mediated activity when the activity in the presence of the agent differs—is greater, lesser or of differing kinetic characteristics—from the activity in the absence of the agent. Standard methods of data analysis such as inhibition curves are employed to analyze effects of the agents being tested.

Alteration of activation of G protein coupled signaling pathways requires the presence of an active receptor coupled to a G protein-dependent signaling system. As an example, this may be accomplished by preparing cell lines co-transfected with the GPCR along with a promiscuous G protein such as Gα16. This G protein acts as a universal adapter and, when activated by a GPCR partner, results in calcium mobilization (Marchese et al., *Trends Pharmacol Sci*, 20:370-375, 1999). Calcium mobilization, in turn is easily assessed by use of the assays described above. For example, a number of fluorescent intracellular calcium probes are available from Molecular Probes, Inc. Changes in intracellular calcium concentration result in changes in fluorescence intensity and/or characteristics of the probe and may be detected using a fluorescence plate reader according to the manufacturer's instructions. Confirmation that an agent affects G protein-coupled signaling by the receptor is then obtained by incubating cells in the presence of the agent of interest at a suitable concentration—typically between about 10 pM and 1 mM—and determining the resultant changes in intracellular calcium concentration. Standard dose-response curves are generated and analyzed.

H. Uses for Agents that Modulate GPCR-Mediated Activity

Agents that modulate one or more GPCR-mediated activities, such as agonists or antagonists of a GPCR, may be used to modulate processes associated with GPCR function and activity. In some embodiments, agents that modulate a GPCR-mediated activity—increase, decrease, or change the kinetic characteristics of the activity—may be used to modulate biological and pathologic processes associated with one or more GPCR-mediated activity.

As used herein, a subject can be any vertebrate, preferably a mammal, so long as the vertebrate or mammal is in need of modulation of a pathological or biological process mediated by a GPCR protein of the invention. The term "mammal" is defined as an individual belonging to the class Mammalia. The invention is particularly useful in the treatment of human subjects.

Pathological processes refer to a category of biological processes that produce a deleterious effect. For example, a particular GPCR-mediated activity or level of activity may be associated with a disease or other pathological condition. As used herein, an agent is said to modulate a pathological process when the agent reduces the degree or severity of the process. For example, a GPCR-mediated activity may be associated with a G-protein signaling disorder, such as those associated with other receptors for biogenic amines (see Background section above for examples).

The agents of the present invention can be provided alone, or in combination with other agents that modulate a particular pathological process. For example, an agent of the present invention can be administered in combination with other known drugs. As used herein, two agents are said to be administered in combination when the two agents are administered simultaneously or are administered independently in a fashion such that the agents will act at the same time.

The agents of the present invention can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

I. Agents that Modulate GPCR-Mediated Activity

Potential agents can be screened to determine if application of the agent modulates a GPCR-mediated activity. This may be useful, for example, in determining whether a particular drug is effective in treating a particular patient with a disease characterized by an aberrant GPCR-mediated activity. In the case where the activity is affected by the potential agent such that the activity returns to normal or is altered to be more like normal, the agent may be indicated in the treatment of the disease. Similarly, an agent that induces an activity that is similar to that expressed in a disease state may be contraindicated.

According to the present inventions a GPCR with an identified ligand may be used as the basis of an assay to evaluate the effects of a candidate drug or agent on a cell, for example on a diseased cell. A candidate drug or agent can be screened for the ability to modulate an activity mediated by the GPCR, for example $Ca^{2+}$ influx.

Assays to monitor the modulation of a GPCR-mediated activity may utilize any available means of monitoring for changes in CNG activity, but is preferably accomplished using one or more of the assay formats described above.

Agents that are assayed in the above methods can be randomly selected or rationally selected or designed. As used herein, an agent is said to be randomly selected when the agent is chosen randomly without considering the specific sequences involved in the association of the a protein of the invention alone or with its associated substrates, binding partners, etc. An example of randomly selected agents is the use a chemical library or a peptide combinatorial library, or a growth broth of an organism.

As used herein, an agent is said to be rationally selected or designed when the agent is chosen on a nonrandom basis which takes into account the sequence of the target site and/or its conformation in connection with the agent's action. Agents can be rationally selected or rationally designed by utilizing the peptide sequences that make up these sites. For example, a rationally selected peptide agent can be a peptide whose amino acid sequence is identical to or a derivative of any functional consensus site.

The agents of the present invention can be, as examples, peptides, small molecules, vitamin derivatives, as well as carbohydrates, lipids, oligonucleotides and covalent and non-covalent combinations thereof. Dominant negative proteins, DNA encoding these proteins, antibodies to these proteins, peptide fragments of these proteins or mimics of these proteins may be introduced into cells to affect function. "Mimic" as used herein refers to the modification of a region or several regions of a peptide molecule to provide a structure chemically different from the parent peptide but topographically and functionally similar to the parent peptide (see Grant, (1995) in Molecular Biology and Biotechnology Meyers (editor) VCH Publishers). A skilled artisan can readily recognize that there is no limit as to the structural nature of the agents of the present invention.

J. Compositions Comprising Agents that Modulate GPCR-Mediated Activity

Compositions comprising the agents of the present invention can be provided alone, or in combination with other compositions and/or agents that modulate a particular pathological process. For example, an agent of the present invention can be administered in combination with other known drugs. As used herein, two agents are said to be administered in combination when the two compositions and/or agents are administered simultaneously or are administered independently in a fashion such that the agents will act at the same time.

Compositions comprising the agents of the present invention can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The present invention further provides compositions containing one or more agents that modulate a GPCR-mediated activity. While individual needs vary, determination of optimal ranges of effective amounts of each component is within the skill of the art. Typical dosages comprise 0.1 to 100 µg/kg body wt. The preferred dosages comprise 0.1 to 10 µg/kg body wt. The most preferred dosages comprise 0.1 to 1 µg/kg body wt.

In addition to the pharmacologically active agent, the compositions of the present invention may contain suitable pharmaceutically acceptable carriers comprising excipients and auxiliaries that facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulations may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

The compositions of the present invention can be utilized in vivo, ordinarily in mammals, such as humans, sheep, horses, cattle, pigs, dogs, cats, rats and mice, or in vitro.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXAMPLES

Example 1

Single Cell Imaging Assay

Figure 2:
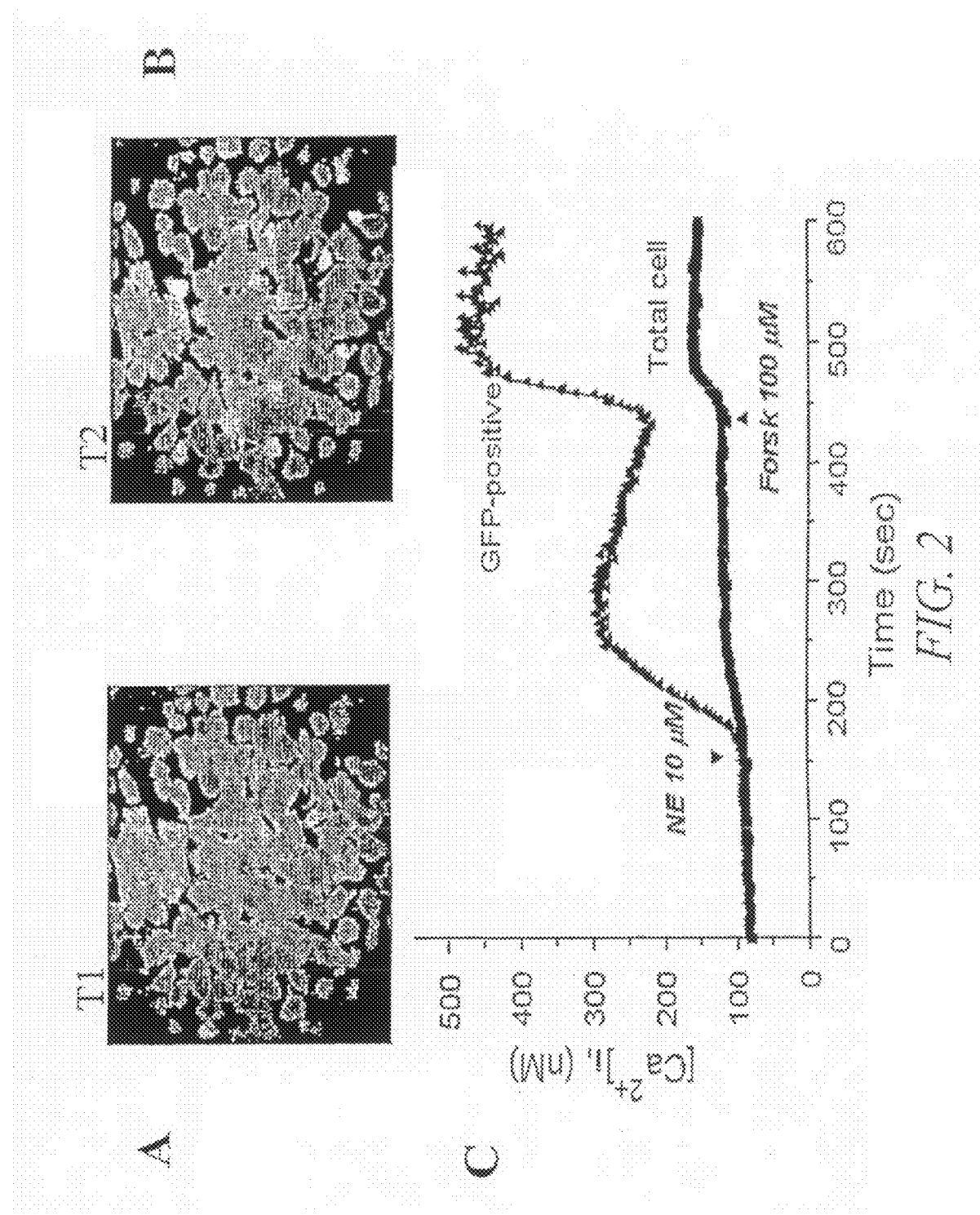
FIG. 2A is a photograph of HEK239 cells transfected with a mutated rat CNG channel gene (SEQ ID NO: 3) prior to their being stimulated with a ligand for an endogenous GPCR.
FIG. 2B shows the cells after stimulation with norepinephrine (NE) that activates endogenous β2-adrenoceptor, a Gs coupled receptor. The signal is detected with a calcium sensitive fluorescence dye, Fura-2 (Molecular Probes, Eugene, Oreg.) by using a fluorescence microscope.
FIG. 2C illustrated an integrated result on intracellular $Ca^{2+}$ concentration of 100 individual cells by using ATTO Graph (ATTO, Rockville, Md.) as a function of time. A plasmid expressing a green fluorescence protein (GFP) was co-transfected with the CNG gene in the host cells.

FIG. 2 shows the results of a single cell imaging assay. In this example, HEK293 cells transiently transfected with a CNG channel (SEQ ID NO: 3) for two days were loaded with a calcium fluorescent dye prior to the recordings. Specifically, cells were cultured on a microscope Fisher brand cover glass #1 pre-coated with MATRIGEL (Becton Dickinson, San Jose, Calif.) incubated in culture medium (DMEM with 10% fetal bovine serum) containing 5 µM fura-2 AM (Molecular Probes, Sunnyvale, Calif.) for 0.5 hour at 37° C. Calcium fluorescence recordings were made on Attofluor® RatioVision® a real-time fluorescence imaging device (ATTO, Rockville, Md.). This system is capable of performing experiments using multiple fluorescent probes such as Fura-2 (for calcium) combined with GFP (transfection marker) in the same cells over the same period of time. Ratio images and graphical data from multiple dyes are displayed on line. This example demonstrates that activation of Gs-coupled GPCR and adenylyl cyclase can be detected by monitoring a change in cytosolic free calcium concentration in a single cell expressing of CNG channels in real time. Upon addition of norepinephrine (NE) and forskolin (forsk) at the times indicated by arrows in FIG. 2, cytosolic calcium concentration started to rise in GFP-positive—i.e., transfected—cells. Two representative images were taken before (Panel A) and after (Panel B) adding NE showing individual cell responses. Calcium fluorescence changes are averaged respectively in GFP-positive cell population and whole cell population and displayed graphically (Panel C).

Example 2

Figure 3:
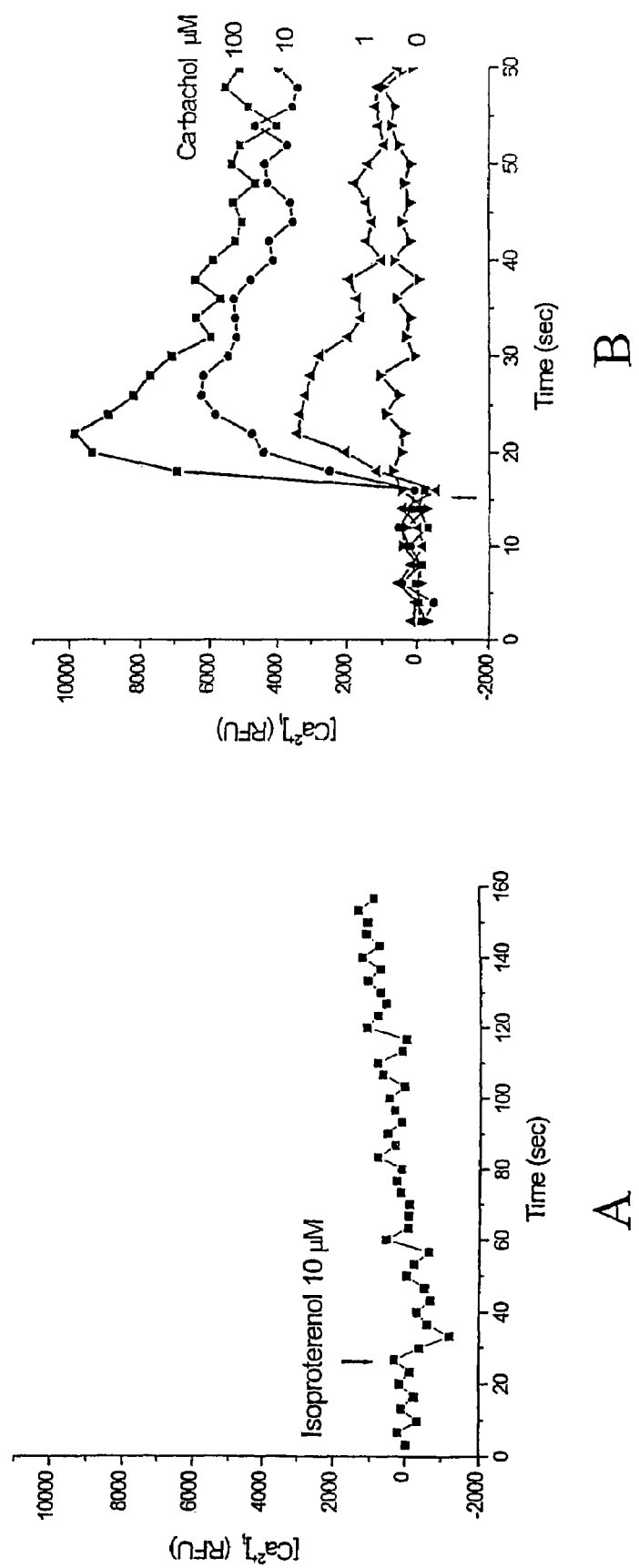
FIG. 3A is a graph of intracellular $Ca^{2+}$ concentration as a function of time in cells transfected with a mutated CNG channel gene (SEQ ID NO: 5) and stimulated with a ligand to Gs coupled endogenous β2-adrenoceptor that results in the accumulation of cAMP and the activation of the CNG channel. The determination of concentration was made by fluorescence of an intracellular dye (Fura-2) as measured by a commercially available microplate reader.
FIG. 3B is a graph of intracellular $Ca^{2+}$ concentration as a function of time in cells transfected with a CNG channel and stimulated with a ligand activating a Gq coupled GPCR, resulting in the mobilization of intracellular $Ca^{2+}$ stores.

Comparison of Calcium Sensitive Dyes and Voltage Sensitive Dyes in a Multiwell Format In this example, recordings were made using a microplate reader FLEXstation (Molecular Devices, Sunnyvale, Calif.) and the protocols provided with the assay kit were adopted for both the calcium assay and the membrane potential assay. FIG. 3 shows the results of a multiwell assay using a mutated CNG channel (SEQ ID NO: 5), which is reported to have a lower value EC50 value for cAMP (Rich, et al. 2001, *J. Gen. Phys.* 118:63-77) than that of SEQ ID NO:3, and therefore expected to be more sensitive to cAMP change. FIG. 3A shows the response to isoproterenol (agonist of β2 adrenergic receptor) determined using a $Ca^{2+}$ sensitive dye, fluo-4 in cells transiently transfected with the CNG channel. There was no significant change in fluorescence of the dye after stimulating cells with a saturating dose of isoproterenol of 10 µM. FIG. 3B shows the results of activation with carbachol, a muscarinic receptor agonist, as a positive control for mobilization of intracellular calcium stores via the Gq pathway. The changes in intracellular $Ca^{2+}$ concentration as a result of this treatment were observable.

Figure 4:
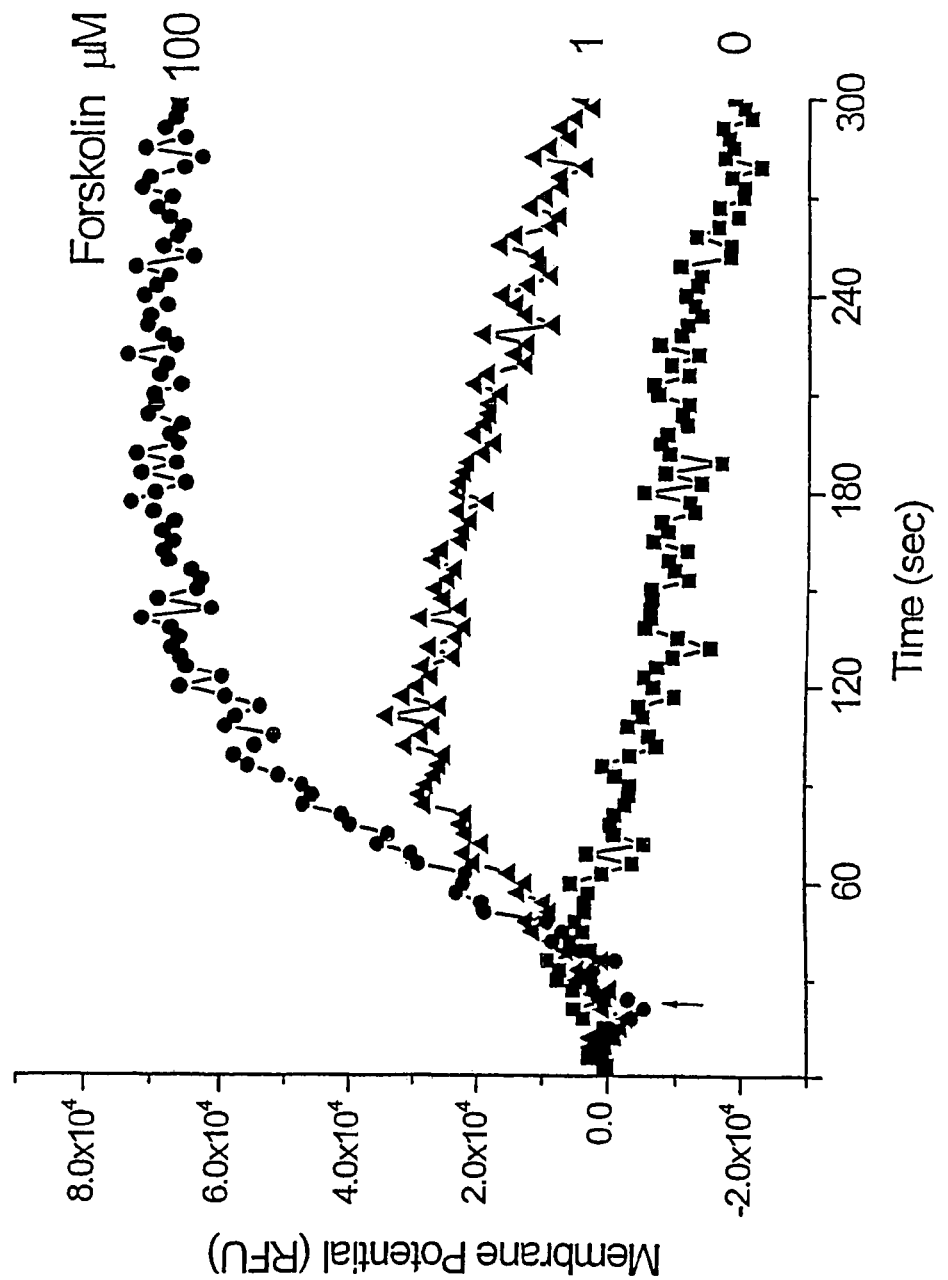
FIG. 4 is a graph of membrane potential as a function of time in cells transfected with a mutated CNG channel gene (SEQ ID NO: 7) and stimulated with forskolin, a direct adenylyl cyclase activator, resulting in the activation of the CNG. The determination of membrane potential was made using a commercially available voltage sensitive dye kit in a multiwell plate reader.

To establish the utility of CNG channels and membrane potential dyes in detecting intracellular cAMP, forskolin, an adenylyl cyclase activator, was used to generate intracellular cAMP. HEK293 cells transiently transfected with a CNG channel (SEQ ID NO: 5) were loaded with the voltage-sensitive dye at room temperature for about 0.5 hour. FIG. 4 shows that upon the addition of forskolin, the intracellular cAMP can be readily detected in the presence of a voltage-sensitive dye by using a microplate reader.

Example 3

Figure 5:
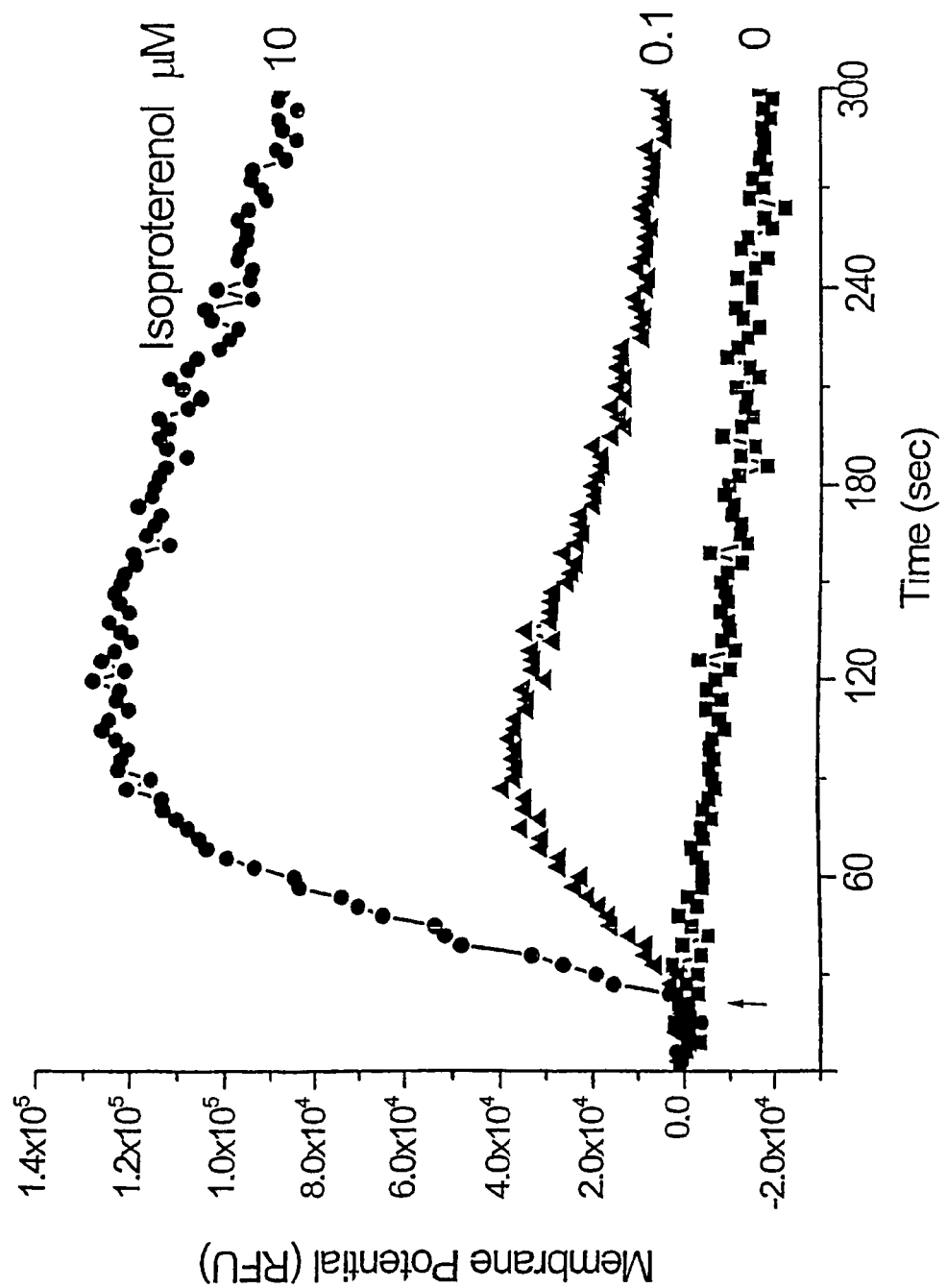
FIG. 5 is a graph of membrane potential as a function of time in cells transfected with a mutated CNG channel gene (SEQ ID NO: 5) and stimulated with a ligand for Gs coupled endogenous β2-adrenoceptor that results in the production of cAMP and activation of the CNG channel. The determination of membrane potential was made using a commercially available voltage sensitive dye kit in a multiwell plate reader.
Figure 6:
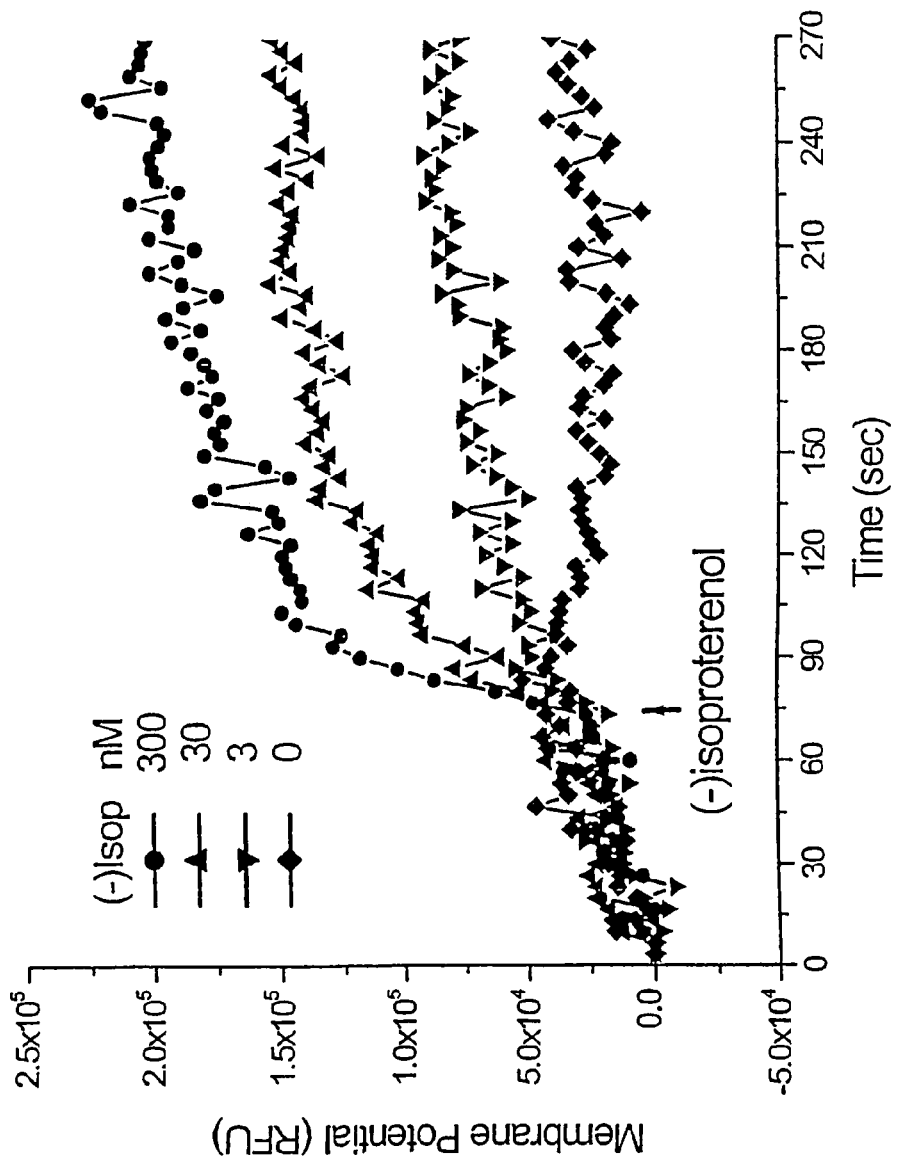
FIG. 6 is a graph of membrane potential as a function of time in cells transfected with a triple mutant CNG channel gene (SEQ ID NO: 7) and stimulated with the indicated concentrations of a ligand to an endogenous Gs coupled β2-adrenoceptor that results in activation of the CNG channel. The determination of membrane potential was made using a commercially available voltage sensitive dye kit in a multiwell plate reader.

Assay for Intracellular cAMP in Response to GPCR Activation Using Mutant CNG Channel with a Membrane Potential Dye FIG. 5 shows the results of a similar assay in which the voltage-sensitive dye of the membrane potential assay kit was used (Molecular Probes, Sunnyvale, Calif.). DPBS (divalent-free Dulbecco's Phosphate Buffer Salts) supplemented with 0.1 mM $MgCl_2$, 1 mM EGTA and titrated to pH 7.3 was used to reconstitute the voltage-sensitive dye instead of the buffer solution supplied in the commercial kit. HEK293 cells transiently transfected with a CNG channel (SEQ ID NO: 5) were loaded with the voltage-sensitive dye at room temperature for about 0.5 hour. A readily detectable change in fluorescence signal was seen at concentrations as low as 0.1 µM isoproterenol that activate β adrenoceptor, as compared to no detectable change with 10 µM isoproterenol using calcium-sensitive dye shown in FIG. 3A. Similarly, FIG. 6 shows the results with membrane potential dye with a different CNG channel mutant (SEQ ID NO: 7).

Example 4

Figure 7:
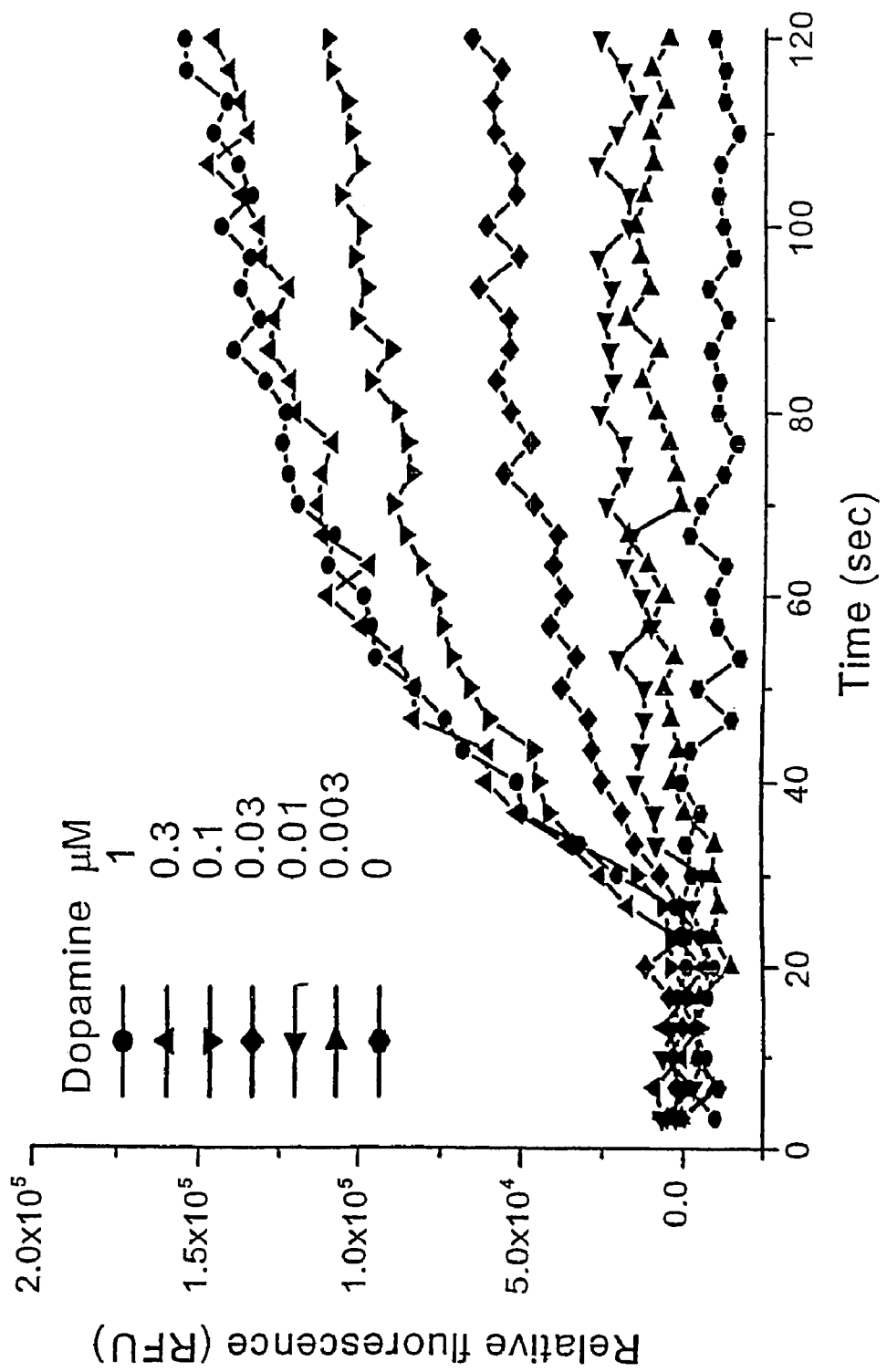
FIG. 7 is a graph of membrane potential as a function of time in cells transfected with both a mutated CNG channel gene (SEQ ID NO: 7) and an heterologous Gs coupled GPCR, dopamine receptor D1, and stimulated with a dopamine. The determination of membrane potential was made using a commercially available voltage sensitive dye kit in a multiwell plate reader.

Assay for Intracellular cAMP with Co-Expressing GPCR and CNG Channel with a Membrane Potential Dye The assays of the present invention can be conducted using an exogenous introduced GPCR. DNA encoding a dopamine type I receptor was co-transfected into cells with a mutated CNG channel (SEQ ID NO: 7) into HEK273 cells. FIG. 7 shows the results of activation of the receptor with its natural ligand, dopamine. Dosage dependent fluorescence signals are obtained immediately following the additional of dopamine in the presence of a membrane potential dye (Molecular Probes, Sunnyvale, Calif.).

Example 5

Identification of Ligands for an Orphan GPCR in Transiently Transfected Cells

Genes encoding for a wild type or mutated CNG channel protein and a GPCR of interest can be transfected into target cell using standard transfection techniques (Ausuebl et al., Current Protocols in Molecular Biology, (2001) John Wiley & Sons). Two days after transfection, approximately 50,000 cells/well for a 96-well plate and 10,000 cells/well for a 384-well plate may be used to create a confluent cell monolayer with a plating volume of 100 µL/well for 96-well plates or 25 µL/well for 384-well plates.

Cell plates may be removed from the incubator after overnight incubation. An equal volume of Loading Buffer with a membrane potential dye (Molecular Devices, Sunnyvale, Calif.) can be added to each well (100 µL per well for 96-well plates, 25 µL for 384-well plates) and the cell plates further incubated for 30 minutes at 37° C. After incubation, the plates can be directly assayed using a FLIPR or FlexStation.

Candidate natural synthetic ligand collections can be obtained and diluted to concentrations ranging from 1 nM to 10 µM for testing. Membrane potential assays will be performed immediately following the addition of the compounds as described in the FLIPR system manual for membrane potential assay (Molecular Devices, Sunnyvale, Calif.). Such assays can also be performed in the presence of $Ca^{++}$ sensitive dye (Molecular Devices, Sunnyvale, Calif.).

Example 6

Identification of Agents that Modulate GPCR-Mediated Activity

Compounds may be screened for their ability to function as agents for the modulation of one or more GPCR-mediated activities. A cell prepared according to the present invention may be contacted with a compound and one or more GPCR-mediated activities may be assayed. As an example, stable cell lines expressing a genes encoding for a CNG channel protein and a GPCR of interest can be obtained (Ausuebl et al., Current Protocols in Molecular Biology, (2001) John Wiley & Sons). The GPCR gene can be of either endogenous or exogenous sources. Approximately 50,000 cells/well for a 96-well plate and 10,000 cells/well for a 384-well plate can be used to create a confluent cell monolayer with a plating volume of 100 µL/well for 96-well plates or 25 µL/well for 384-well plates.

Cell plates can be removed from the incubator after overnight incubation. An equal volume of Loading Buffer with a membrane potential dye (Molecular Devices, Sunnyvale, Calif.) is then added to each well (100 µL per well for 96-well plates, 25 µL for 384-well plates) and the cell plates further incubated for 30 minutes at 37° C. After incubation, the plates can be directly assayed using the FLIPR. Libraries of compounds can be obtained and diluted to concentrations ranging from 1 nM to 10 µM for testing. Membrane potential assays are performed immediately following the addition of the compounds as described in the FLIPR system manual for membrane potential assay (Molecular Devices, Sunnyvale, Calif.). Such assay can also be performed in the presence of both membrane potential and $Ca^{2+}$ sensitive dyes (Molecular Devices, Sunnyvale, Calif.).

Example 7

A Homogeneous, Kinetic Assay with HEK 293-CNG Cells in 384-well Plates with Membrane Potential Dye Populations of cells are stably transformed to express CNG channel and established under either adherent or suspension culture conditions. The cells are harvested and adjusted to $1 \times 10^6$ cells/ml in DMEM (high glucose) comprising 10% FBS. 20 µl of the cell suspension is dispensed per well into 384-well microplates (Corning; 3712) and incubated 16-24 hours prior to assay. Immediately prior to assay, wells of the cell plates are observed microscopically to confirm the presence of confluent lawns of consistently spread cells.

Membrane potential dye stock (Membrane potential reagent kit, Component A, Molecular Devices, R-7056) stock solution is prepared by dissolving one bottle of dye in the kit in 10 ml Dulbecco's Phosphate Buffered Saline (DPBS) supplemented with 20 mM HEPES (pH 7.0), aliquoted into 1 ml portions and stored at −80° C. Dye Loading Buffer is prepared on the day of the assay by diluting 1 ml dye stock with 9 ml of the DPBS supplemented with HEPES at 20 mM, pH 7.0 per 384-well plate. 20 µl Dye Loading Buffer per well is added to the 384-well cell plates. Plates are incubated at room temperature, about 20-25° C., for 1-7 h. During incubation, dilutions of test compounds are prepared in Compound Buffer (10 mM EGTA in Dye Loading Buffer; pH 7.2).

Dye loaded cell plates are then loaded into a FLIPR384, FLEXstation, or other fluorescence microplate reader and assayed per fluorescence microplate reader instructions. For example, in a FLIPR384, 488 nm excitation and 540-590 nm emission filters are used; for FLEXstation and other fluorescence microplate readers, wavelengths close to the maxima of absorption and emission of the dye are used: for example, 540 nm excitation and 560 nm emission for the membrane potential dye of Molecular Devices, R-7056). Ten μl of test compound in Compound Buffer is added per well and the results are recorded.

Figure 10A:
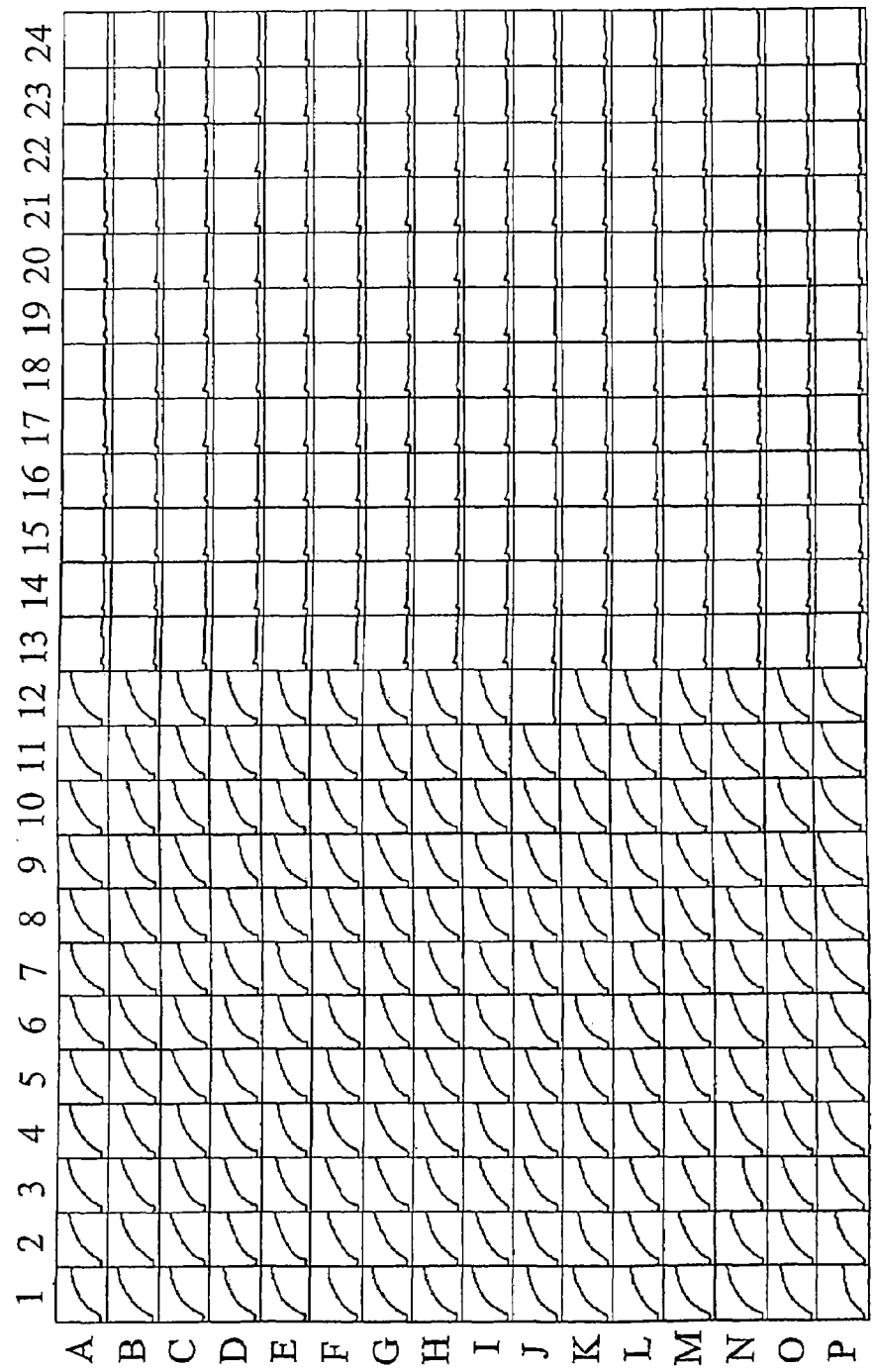
Figure 10B:
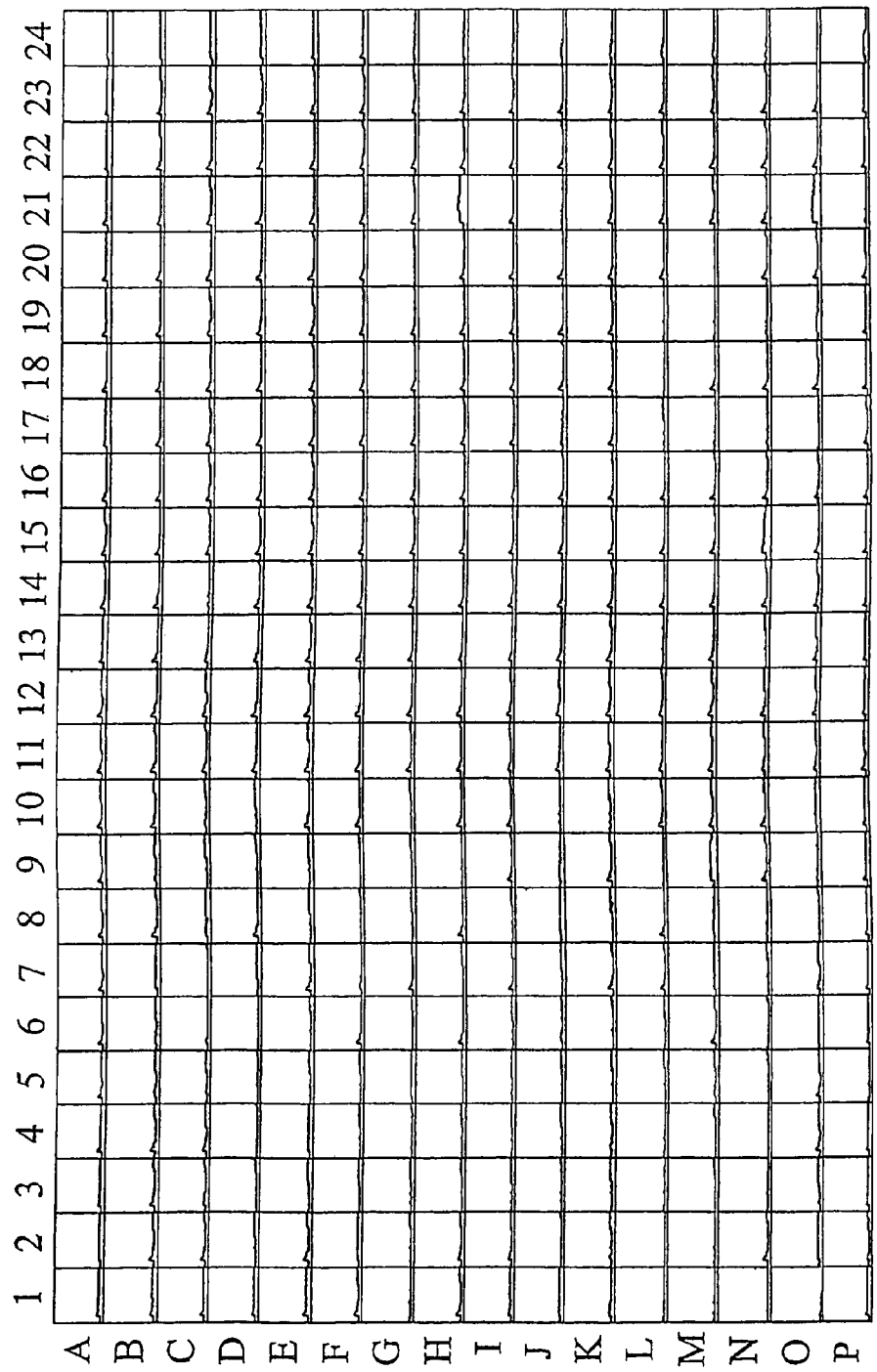
Figure 10C:
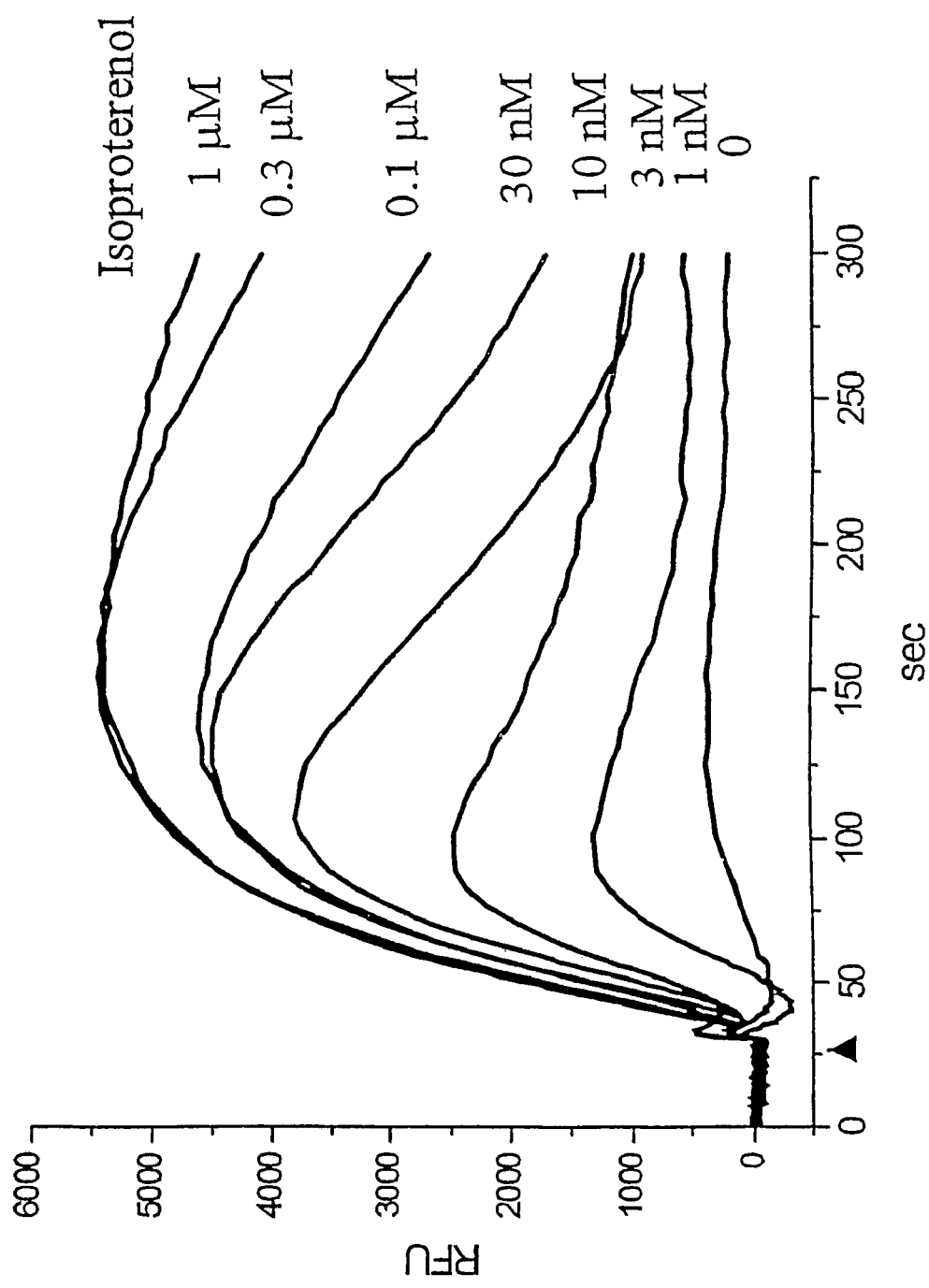

In the present example, the CNG channel assay was adapted to a HTS platform, FLIPR (Molecular Devices). Specifically, a stably transformed HEK 293H cell line expressing CNG channels (SEQ ID NO:: 7) was used for a cAMP assay. Cells were seeded into 384-well plate coated with MATRIGEL (Becton Dickinson, 354234) using a Multidrop 384 dispenser (Titertek Instruments, Inc.). Well-to-well variability of CNG channel assay for cAMP responses was assessed in the recordings of 4 min duration shown in FIG. 10. 30 seconds after beginning the recordings, Isoproterenol (1 μM final) was added to the wells of columns 1-12 while compound buffer was added as a control to the wells of columns 13-24 at time of (FIG. 10). HEK293H-CNG cell line and the parental cell line lacking CNG was used in FIGS. 10A and 10B respectively. Dose-dependent responses to isoproterenol were obtained in separate recordings. Multiple fluorescence traces in response to various doses of isoproterenol were overlaid (FIG. 10C). Data consistency is demonstrated in FIG. 10D by overlaying multiple responsive curves for 1 μM isoproterenol from the plate of FIG. 10A.

Example 8

A Kinetic Assay with HEK 293H-CNG Cells with Calcium-sensitive Dye

Populations of cells, e.g., HEK 293 or HEK 293H, are stably transformed to express CNG channel, e.g., SEQ ID NO: 7, and established under either adherent or suspension culture conditions. The cells are harvested and adjusted to $1 \times 10^6$ cells/ml in DMEM (high glucose) comprising 10% FBS. 20 μl of the cell suspension is dispensed per well into 384-well microplates, or 100 μl of the cell suspension is dispensed per well into 96-well microplates, and incubated 16-24 hours prior to assay. Immediately prior to assay, wells of the cell plates are observed microscopically to confirm the presence of confluent lawns of consistently spread cells.

Calcium-sensitive dye Fluo-4 μM (Molecular Probes, F-14202) is prepared as a 4 mM stock solution in DMSO and stored at –20° C. On the day of assay, stock solution is diluted to a final dye solution concentration of 4 μM cells in Hanks' Balanced Salt Solution (HBSS, pH 7.2). Cells are loaded with the dye by replacing the DMEM+FBS in the wells with the HBSS dye solution and incubation at room temperature for 1 hour. During incubation, prepare compound plates. Test compounds are dissolved in HBS or HBS supplemented with 10 mM $CaCl_2$.

Dye loaded cell plates are then loaded into a FLIPR384, FLEXstation, or other fluorescence microplate reader and assayed per fluorescence microplate reader instructions.

In the present example, a stably transformed HEK 293H cell line expressing CNG channels (SEQ ID NO: 7) was assayed for calcium uptake. 30 seconds after beginning the recordings, isoproterenol was added to wells at final concentrations of 0.3, 1.0, 3.0, 10.0, 30.0 and 300.0 nM. Buffer solution only was added to control wells. Dose-dependent responses to isoproterenol were recorded and multiple fluorescence traces in response to the various doses of isoproterenol were overlaid as shown in FIG. 11.

Example 9

Single Cell Imaging Assay

In this example, stably transformed HEK 293H cells expressing a CNG gene (SEQ ID NO: 7) were assayed using a voltage-sensitive dye (Molecular Devices, R-7056). Cells were seeded into a 96-well plate pre-coated with MATRIGEL. Membrane potential fluorescence recordings were made on Pathway HT imaging platform (ATTO, Rockville, Md.) in the same cells over the same period of time. Confocal fluorescence intensity images were displayed in FIG. 12 with an arbitrary intensity range of 280-650. The images were obtained before and 15, 30 and 45 seconds after addition of isoproterenol to final 1 μM in a time sequence marked in the FIG. 12A. One imaging area of 50×50 um was displayed in FIG. 12A. Average of fluorescence traces obtained in 71 imaged cells was shown in FIG. 12B. The time of addition of isoproterenol was marked with an arrow.

Example 10

Figure 13:
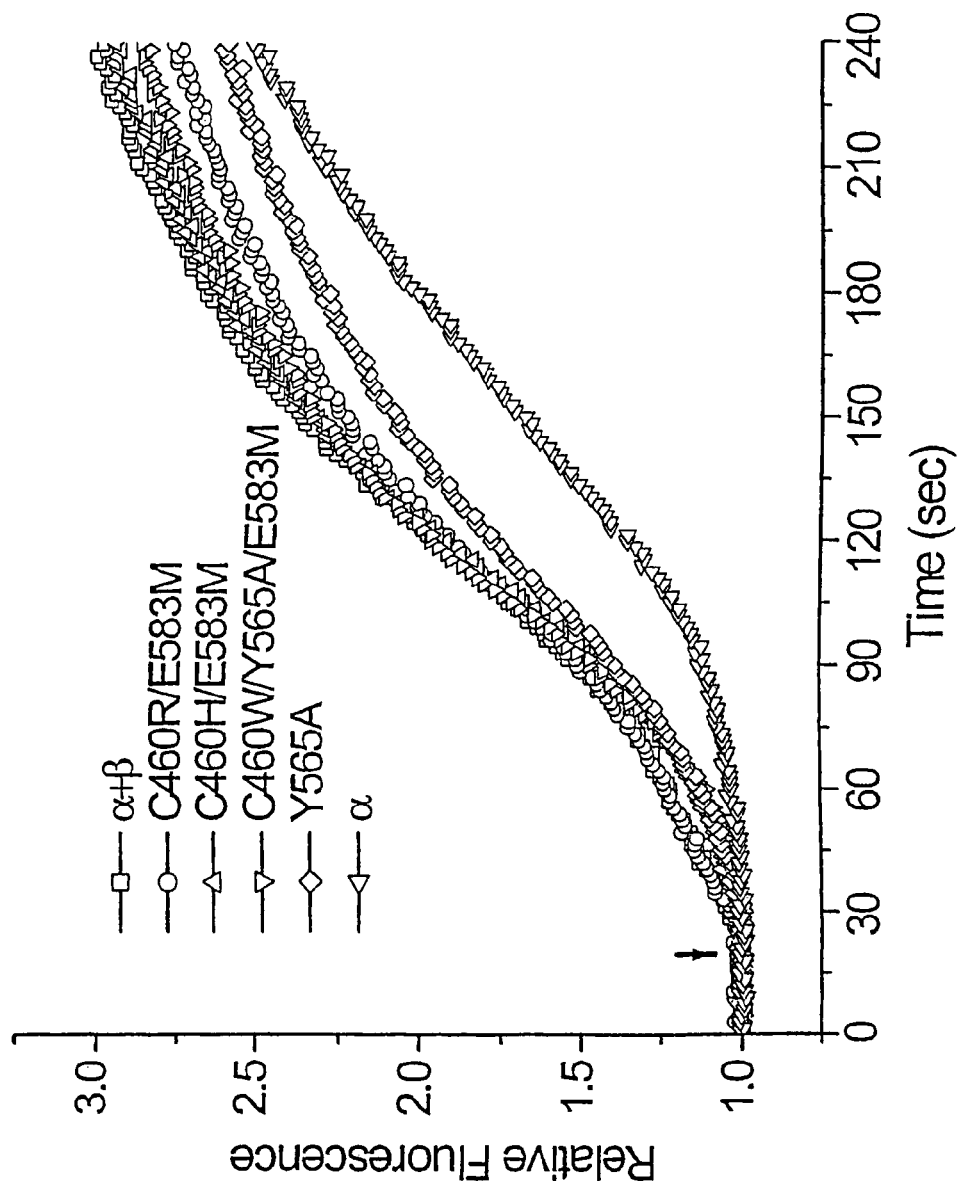
FIG. 13 depicts the sensitivity of CNG channels which are composed of wildtype heteromeric (α+β) subunits, wildtype homomeric (α) subunits, or mutant homomeric CNG channels comprising one (Y565A), two (C460R/E583M and C460H/E583M), or three (C460W/Y565A/E583M) substitution mutations.

Assay for Intracellular cAMP using CNG Channels of Wild Toe Subunits and Subunits Containing Mutations Relative fluorescence responses to cAMP rise of in cells transiently transfected with wild type α+β subunit heteromeric CNG channels, homomeric CNG channel α subunits comprising various mutations, or homomers of CNG channel wild-type α subunit alone was explored. In this example, HEK293 cells were transfected two days prior to the recordings with rat olfactory wild type CNG channel α subunit (NCBI LocusID 25411, SEQ ID NO: 1) plus β subunit (NCBI LocusID 85258), the rat olfactory CNG channel α subunit containing mutations C460R/E583M, C460H/E583M, C460W/Y565A/E583M (SEQ ID NO: 7), or Y565A (SEQ ID NO: 3), and α subunit alone (NCBI LocusID 25411, SEQ ID NO: 1). The cells were incubated in Dye Loading Buffer containing membrane potential dye (Molecular Devices, R-7056) at room temperature. Isoproterenol was dissolved in Compound Buffer as in Example 8 to a final concentration of 300 nM and added at the time marked with an arrow (FIG. 13). FIG. 13 shows that isoproterenol responses in cells expressing heteromeric CNG channels composed of wild type α and β subunits are larger than or similar to those expressing CNG channels formed by homomeric wild type α subunit or α subunit homomers containing mutations of C460R/E583M, C460H/E583M, C460W/Y565A/E583M, or Y565A (FIG. 13).

Example 11

Sensitivity Comparison between CNG Channel Assay with a Conventional Transcription Assay and a cAMP ELISA Assay A number of cAMP assay technologies have been developed based on the principles of competitive binding of cAMP antibody or transcription of genes regulated by cAMP-response elements (CRE). In assays using cAMP-specific antibodies, cell lysis is required to release cAMP to the assay media. As a result, assay sensitivity is compromised as cell number is reduced. In gene reporter assays, more false positive and negative recordings are expected as CRE transcription can be affected non-specifically by varieties of signaling pathways. In contrast, the CNG channel assay provides a direct physiological readout of cAMP intracellularly to avoid the problems associated with conventional indirect cAMP assay technologies. CNG channels are targeted to the plasma membrane and co-localized with adenylyl cyclase to permit a sensitive detection of a local cAMP rise. Because fluorescence readout in the CNG channel assay derives from activity of single live cells, assay sensitivity is not compromised by reducing cell numbers, as it may be in indirect assays.

Figure 14:
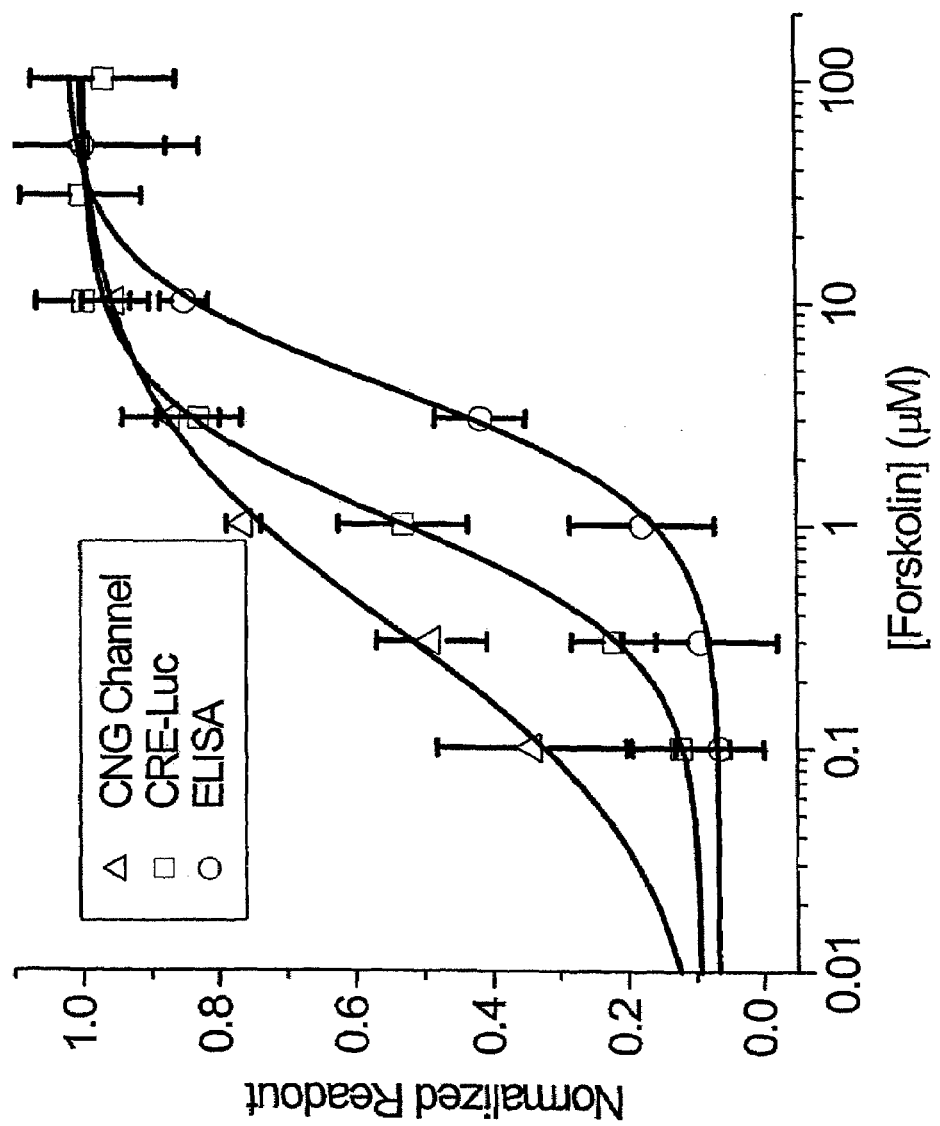
FIG. 14 depicts a comparison between the CNG channel assay and conventional CRE and ELISA assays. Each assay format is depicted as a dose-response to forskolin stimulation.

A comparison of the CNG channel assay was made with an ELISA-based anti-cAMP antibody binding assay (Amersham Biotrak kit, used according to kit directions) and a conventional CRE-Luciferase gene reporter assay in 96-well format. Dose-response curves were generated to forskolin using the same ligand concentrations for all 3 assay formats. FIG. 14 shows that the response curve is left-shifted in general using the CNG Channel assay and demonstrates that low concentrations of forskolin induced a significantly larger response in CNG channel assay than in the ELISA and gene reporter assay formats, indicating that CNG channel assay is more sensitive than these conventional cAMP assays.

Example 12

CNG Channel Assay for Gs-Coupled GPCRs of Different Families

Figure 15:
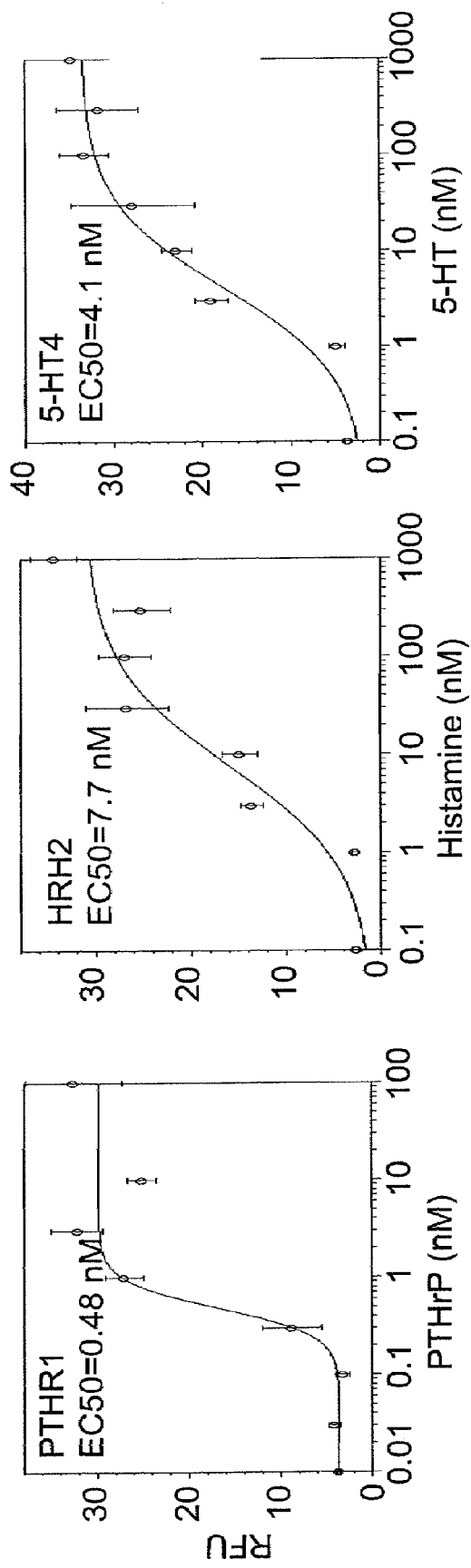
FIG. 15 depicts the sensitivity of the CNG channel assay for activation of GPCRs for various ligands. Representative dose-response curves are depicted for Parathyroid Hormone Receptor 1 (PTHR1), Histamine Receptor H2 (HRH2), and 5-Hydroxytryptamine 4 Receptor (5-HT4) response to the agonists PTHrP (peptide), Histamine (monoamine), and 5-HT (monoamine), respectively.

To show the sensitivity of the CNG channel assay as a kinetic assay for Gs-coupled GPCRs, Gs-coupled GPCRs were randomly chosen from class B (the secretin family) and class A (including, for example, biogenic amines, peptides, prostanoids, and adenosine receptors) for assay. Activation of the GPCRs listed in Table 1 by their cognate agonists was examined applying CNG channel assay. All of these GPCRs were read out successfully by CNG channel assay, demonstrating the ability of the CNG assay to provide accurate kinetic measurements of Gs-coupled CPCR activation, regardless of its ligand family. FIG. 15 showed dose-response curves of three GPCRs tested to illustrate their relevance to the other pharmacological analysis.

TABLE 1

Gs-coupled GPCRs tested with CNG channel assay

| Receptor | Ligand Tested | Ligand Type |
| --- | --- | --- |
| Dopamine D1 | Dopamine | Mono amine |
| Beta-Adrenergic | Isoproterenol, Epinephrine | Mono amine |
| Histamine H2 | Histamine | Mono amine |
| 5-Hydroxytryptamine 4 | 5-Hydroxytryptamine | Mono amine |
| Tyramine | Tyramine | Mono amine |
| Prostaglandin E 2 | Prostaglandin E1 | Lipid |
| Prostaglandin D2 | Prostaglandin D2 | Lipid |
| Calcitonin | Calcitonin | Peptide |
| Glucagon | Glucagon | Peptide |
| Parathyroid Hormone 1 | PTH, PTHrP | Peptide |
| Vasoactive Intestinal Peptide 1 | VIP | Peptide |
| Arginine Vasopressin 2 | Arginine Vasopressin | Peptide |
| Melanocortin 1 | α MSH | Peptide |
| Melanocortin 3 | α MSH | Peptide |
| Melanocortin 4 | α MSH | Peptide |
| Melanocortin 5 | α MSH | Peptide |
| Adenosine A2b | NECA | Nucleotide |

Example 13

Robustness of CNG Channel Assay in Comparison with Assay using Promiscuous G Protein and G Protein Chimera Calcium fluorescence assays using the promiscuous G protein $G\alpha_{16}$ and the G protein chimera $G\alpha_{qs}$ have been previously used to measure intracellular calcium rise. However, measurement of GPCR activation using either $G\alpha_{16}$ or $G\alpha_{qs}$ is indirect, as both re-direct the activity of some Gs-coupled GPCRs to a phospholipase C-mediated intracellular calcium rise. Because the coupling efficiency of $G\alpha_{16}$ and $G\alpha_{qs}$ varies between Gs-coupled GPCRs, the final calcium signal readout varies between receptors.

Figure 16:
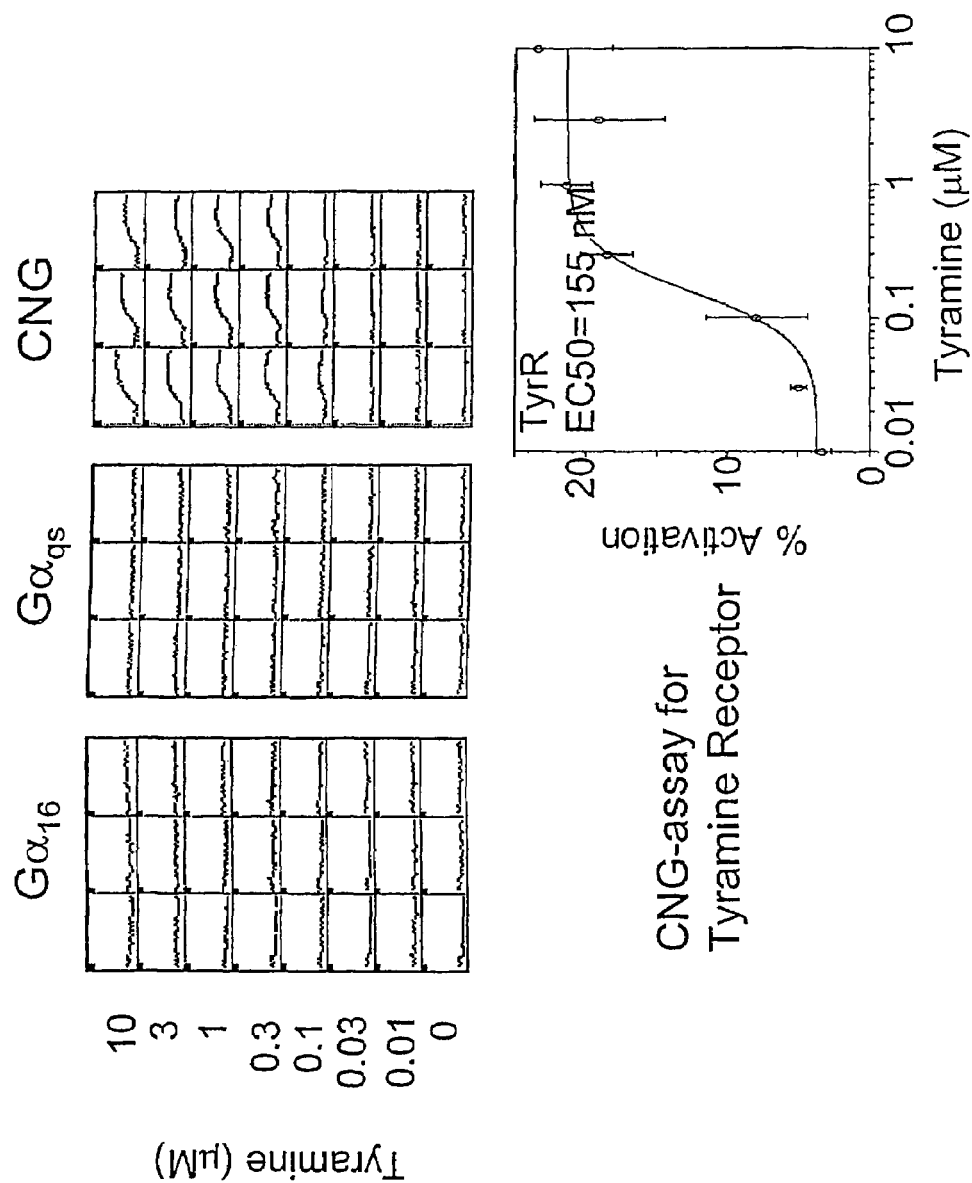
FIG. 16 depicts a dose-response comparison of the CNG channel assay using membrane potential dye to calcium assays using promiscuous G protein ($G\alpha_{16}$) or chimeric G protein ($G\alpha_{qs}$) for detecting activation of the tyramine receptor.

In this example, activation of the tyramine receptor was examined using the CNG channel assay and compared with calcium fluorescence assays using $G\alpha_{16}$ and $G\alpha_{qs}$. Similar amounts of plasmids comprising CNG channel, $G\alpha_{16}$ or $G\alpha_{qs}$ were used for transient expression in HEK293 cells also transiently expressing tyramine receptor. Calcium assays were performed following the protocol provided by Molecular Devices. For each concentration of tyramine, three recordings were made to obtain an average response in cells expressing $G\alpha_{16}$, $G\alpha_{qs}$ and CNG channel respectively. As shown in FIG. 16, tyramine receptor activation is detectable using the CNG channel assay with membrane potential dye, but not by calcium fluorescence assays using $G\alpha_{16}$ or $G\alpha_{qs}$ and calcium dye (FIG. 16).

Example 14

Identification of Agonists and Antagonists of GPCRs Applying CNG Channel Assay

Figure 17:
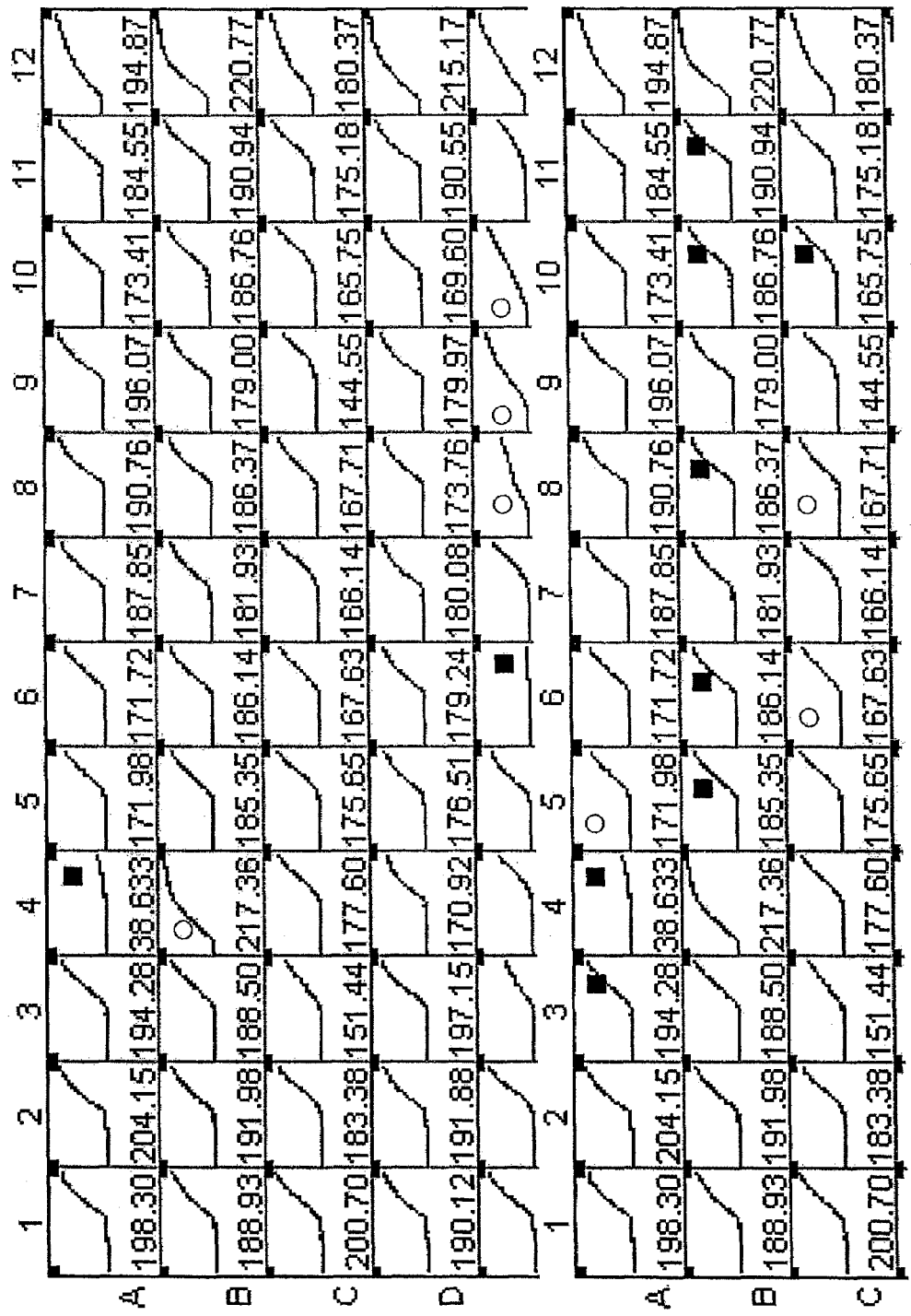
FIG. 17A depicts the response of HEK293H-CNG cells to a panel of adrenergic compounds as depicted in FIGS 17B-D.

The CNG channel assay can be used to identify GPCR ligands. In this example, the CNG channel assay was used to probe a panel of adrenergic compounds for those that are agonists or antagonists of β-adrenoreceptors. Stably transformed HEK293H cells expressing a CNG channel gene (SEQ ID NO: 7) were seeded into 96 well plates and grown as described in previous examples. Test compounds were arrayed in columns 1-11 of a 96-well plate as shown in FIG. 17B-D, with buffer only as a control in column 12. Test compounds were added to the cell plates 20 seconds after the start of recordings to a final concentration of 1 μM. Isoproterenol, 10 μM final concentration, was added at 120 seconds to evoke cAMP rise. Time duration of recordings was 230 seconds. Agonists were identified by the detection of a fluorescence rise immediately following the addition of the test compound, before the addition of isoproterenol and are marked by hollow circles in FIG. 17A. Antagonists were identified by delaying or ablating the response of cells to isoproterenol stimulation, as marked by solid squares in FIG. 17A.

Example 15

Endpoint Assay

The CNG channel assay can also be used to perform endpoint assays. Decay of fluorescence responses results from desensitization of CNG channel was effectively removed by chelating extracellular calcium by EGTA and supplementing inhibitors of phosphodiesterase. Stably transformed cells expressing a CNG channel gene were seeded into 384 well plates and grown as described in previous examples. Forskolin was dissolved at a final concentration of 30 μM in Compound Buffer containing EGTA. Fluorescence intensity values of cells incubated with forskolin or with Compound Buffer only were read using FLEXstation (Molecular Devices) at different time points after forskolin stimulation. Treatment with forskolin resulted in a fluorescence intensity of $5.3 \pm 0.5 \times 10^5$ RFU (30 μM forskolin, n=192) at 90 minutes after stimulation, versus $1.9\pm0.1\times10^5$ RFU (buffer control, n=192), representing a 2.8-fold increase.

Example 16

Identification of Fluorescence Quenchers

Figure 18:
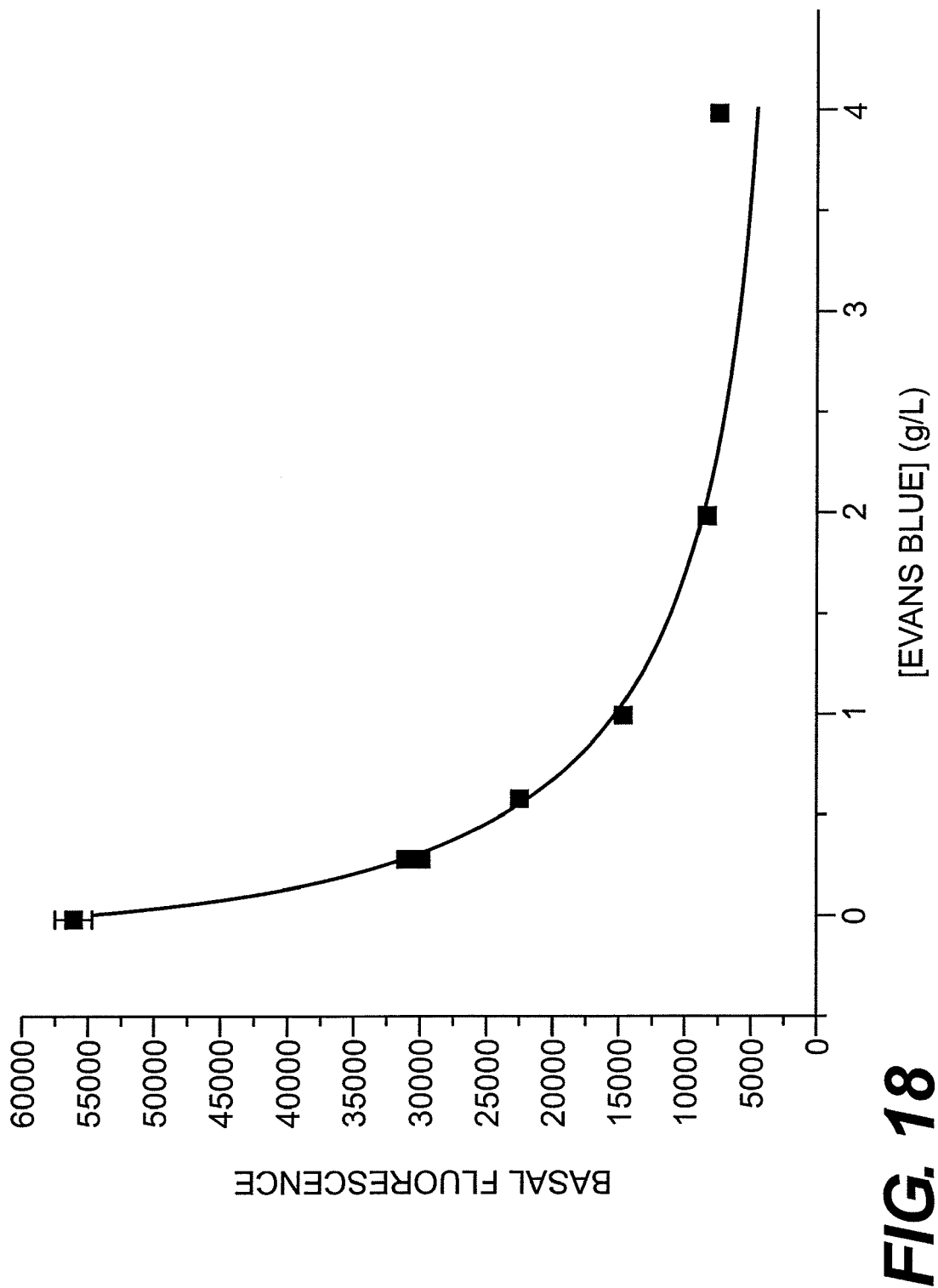
FIG. 18 is a graph showing concentration-dependent quenching of extracellular fluorescence by a membrane impermeable absorbance dye, evans blue. Concentration-dependent fluorescence quenching is fitted to the Stem-Volmer equation. The smooth curve in figure is the best non-linear fit to the total fluorescence, as the most fluorescence readings are contributed by extracellular dye fluorescence. The half-quenching concentration is 0.38 g/L, corresponding to 0.34 mM evans blue.
Figure 19:
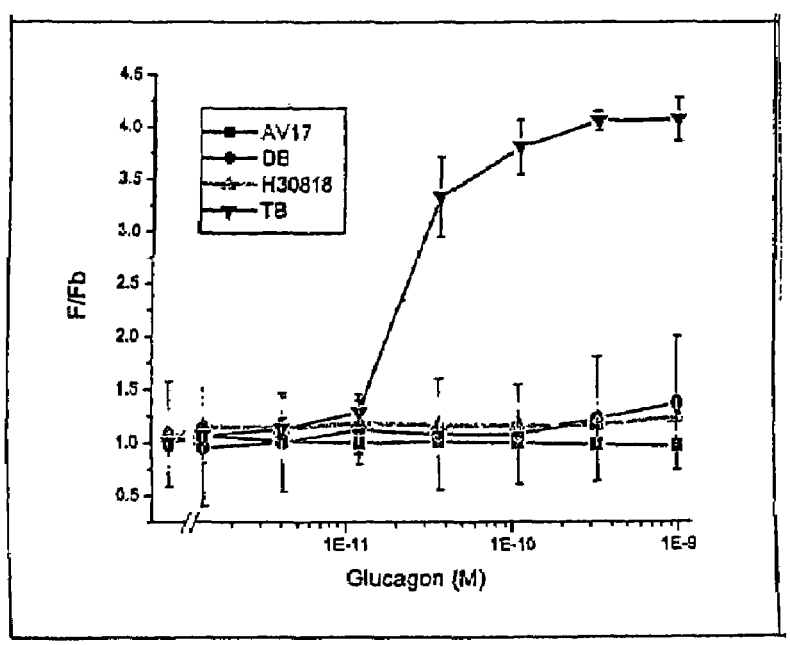
FIG. 19 is a graph showing how dye quenchers containing positive charges may interfere with cell responses. A stable 293H cell line expressing CNG channel and glucagon receptor, ASC0089, was loaded with a voltage dye, HLB30602 of 5 µM in the presence of a quencher dye for 1 h at room temperature. Cell response to glucagon was abolished when using dye quenchers, acid violet 17 (AV17), diazine black (DB), and HLB30818, which contain positive charges. Trypan blue (TB) is a negative-charged dye.

Generally, the pre-selection of dye quenchers (Table 1) is based on their physical chemistry properties: (1) water solubility, (2) absorption spectra overlapping with emission spectra of fluorescent indicators, (3) low autofluorescence, and (4) complete exclusion from cells, i.e. do not affect intracellular fluorescence (Sahlin et al., 1983). Effective quenching of extracellular fluorescence by absorbance dye quenchers is achieved at 0.1-10 mM concentration (FIG. 18) (Sahlin et al., 1983, Differentiation between attached and ingested immune complexes by a fluorescence quenching cytofluorometric assay. *J. Immunol. Methods*. 60:115-124; Wan et al., 1993, A rapid and simple microfluorometric phagocytosis assay. *J. Immunol. Methods*. 162:1-7). Positive-charged dyes have large quenching effects on a negative-charged fluorescent voltage dye, HLB30602, in cell-free solution (Table 2). However, many quenchers are not suitable for use in cell-based assays due to their poor exclusion by cells (Sahlin et al., 1983). For instance, cellular responses were totally lost in the presence of many known positive-charged dye quenchers (FIG. 19). Prior to the present invention, it was not known how to select a quencher dye that will have little or no interference on cell-based assays based on the molecular structure of the dye or its physical chemistry properties.

Figures 20, 21:
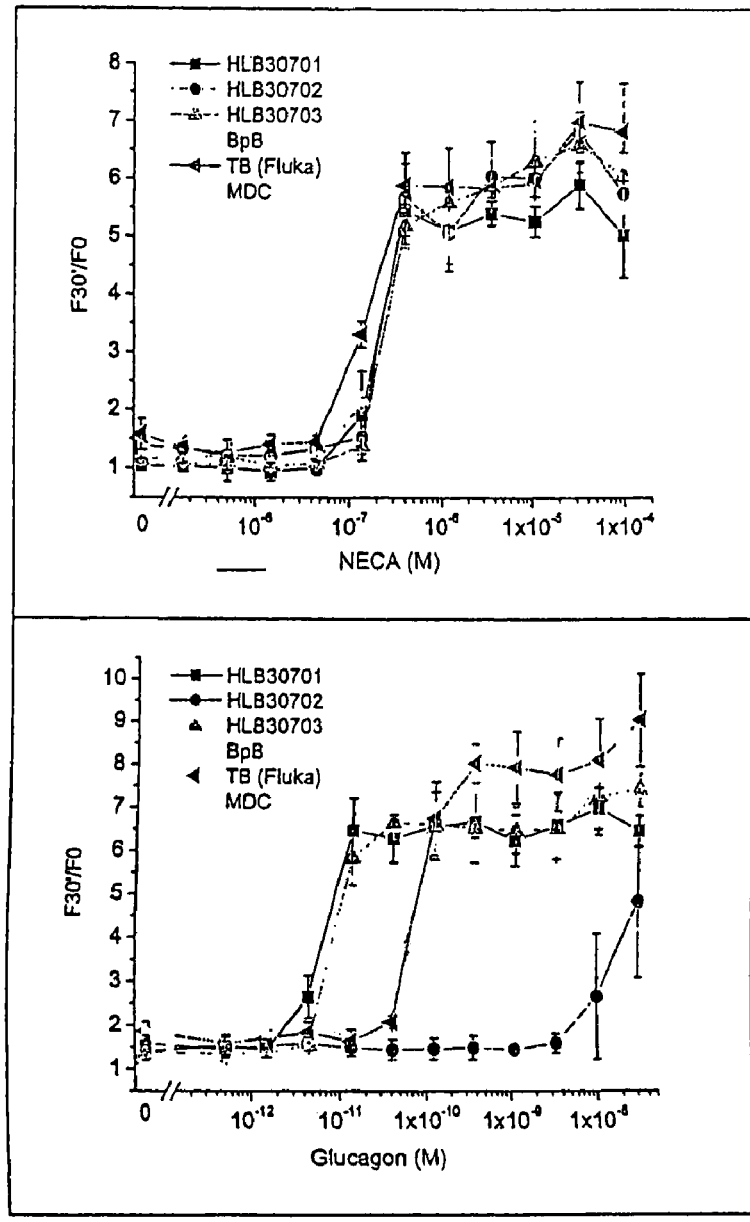
FIG. 20 is a graph showing that most pre-selected negative-charged dye quenchers are suitable for assay of adenosine receptor A2B responses to an agonist, NECA, including HLB30701, HLB30702, HLB30703, and trypan blue. However, a negative-charged dye, bromophenol blue (BpB) reduced NECA response without affecting NECA potency.
FIG. 21 is a graph showing that response to glucagon stimulation was interfered by dye quenchers, HLB30702, trypan blue (TB), and bromophenol blue (BpB). Trypan blue did not inhibit maximal responses but reduced glucagon potency by about one order in comparison with quenchers, HLB30701, HLB30703, and a commercial dye kit from Molecular Devices, Corp. (MDC, Cat #R-8034).

A functional screening of dye quenchers against 20 ligand-receptor pairs was performed in order to identify those candidate quenchers with the least pharmacological interference (Table 3). The chemical composition of the tested ligands include peptides and small organic molecules such as adenosine, lipid, monoamine, etc. Of the quenchers screened using the described invention, many were found to reduce the potency ($EC_{50}$) of the ligands without effecting the maximum responses. Further quenchers were identified that inhibited maximal response in the assay (bromophenol blue, FIGS. 20, 21). Many dye quenchers such as trypan blue, HLB30701, HLB30702, and HLB30703 (FIG. 20, Table 2) are suitable for use in assays in which the ligand is a small organic compound. However, we discovered that several of these quenchers interfered with assay responses to peptide ligands.

Figure 24:
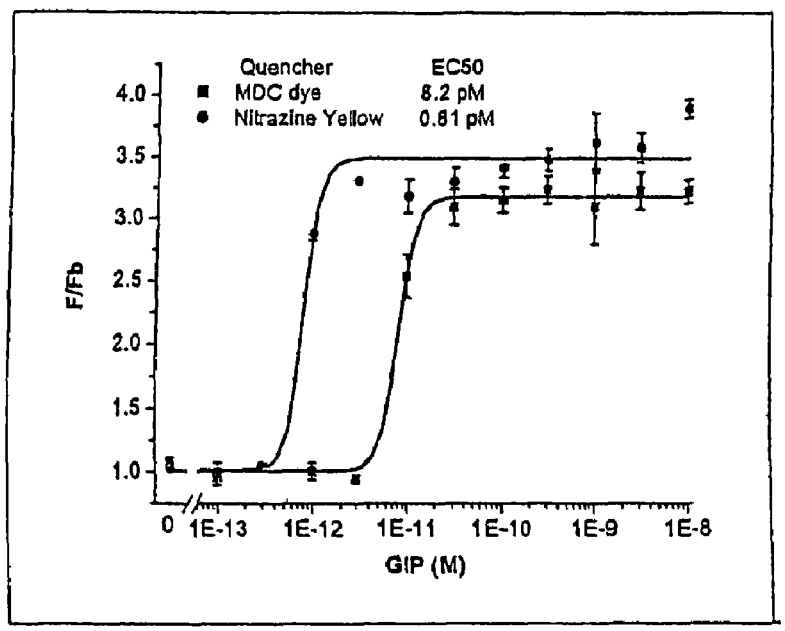
FIG. 24 is a graph showing GIP dose-responses in the presence of quencher dyes. Cell line: ASC0133 (GIPR). GIP potency increased using nitrazine yellow as a quencher by one order comparing using a commercial dye kit from Molecular Devices, Corp. (MDC, Cat #R-8034).

For example, trypan blue significantly reduced glucagon potency (FIGS. 22, 23, Table 3). Nitrazine yellow (FIG. 25) and nitro red (FIG. 26) were identified in the functional screening of the invention. These quenchers were found to provide the most sensitive assay for peptides, and small molecule ligands (Table 3). For example, the dose-response curves of the peptides VIP and GIP, are left-shifted by about one order of magnitude using nitrazine yellow as the quencher in comparison with a non-disclosed quencher in a commercially available voltage dye assay kit (Molecular Devices, Corp., R-8034) (FIGS. 23, 24).

TABLE 2

A list of dye quenchers are pre-selected based on their absorbance spectra. Quenching efficiency was determined by ratioing fluorescence levels of a voltage dye, HLB30602 of 10 μM, in the absence and presence of quencher dyes at concentration of 0.5 g/L (F0/F).

| Dye Quencher | MW | Absorbance Peak (nm) | Dye Charge | Solubility in Water (g/L) | Quenching Efficiency Residual F (k) | F0/F |
|---|---|---|---|---|---|---|
| Acid Blue 92 | 695.59 | 571 | −3 | 40 | 57.60 | 36 |
| Acid Blue 113 | 681.66 | 566 | −2 | 40 | 112.50 | 19 |
| Acid Violet 17 | 761.94 | 545 | −2, +1 | 30 | 6.90 | 304 |
| Alizarin Red S monohydrate | 360.28 | 556 | −1 | 20 | 335.10 | 6 |
| Brilliant Black BN | 867.69 | 570 | −4 | 30 | 19.30 | 109 |
| Bromochlorophenol Blue | 580.07 | 590 | −1 | 20 | 421.00 | 5 |
| Bromocresol Purple | 562.22 | 585 | −1 | 80 | 115.60 | 18 |
| Bromophenol Blue | 598 | 589 | −1 | 30 | 44.90 | 47 |
| Bromopyrogallol Red | 576.18 | 552 | −1 | 5 | 31.60 | 66 |
| Chlorophenol Red | 423.28 | 572 | −1 | 30 | 62.40 | 34 |
| DIAZINE BLACK | 484.01 | 584 | +1 | | 9.30 | 226 |
| Direct Violet 51 | 719.71 | 549 | −2 | 20 | 152.00 | 14 |
| MELDOLA'S BLUE | 378.93 | 570 | +1 | | 2.10 | 1000 |
| Methylene Violet 3Rax | 378.91 | 557 | +1 | 10 | 87.40 | 24 |
| New Fuchsin | 365.91 | 553 | +1 | 20 | 3.40 | 618 |
| Nitrazine Yellow | 542.37 | 586 | −2 | 20 | 59.80 | 35 |
| Nitro Red | 512.39 | 572 | −2 | 40 | 62.10 | 34 |
| Palatine Chrome Black 6BN (Calcon) | 416.39 | 569 | −1 | 30 | 362.00 | 6 |
| Sulfonazo II | 776.57 | 567 | −4 | 40 | 98.70 | 21 |
| Thymol Blue | 488.58 | 590 | −1 | 60 | 699.00 | 3 |
| Trypan Blue (Fluka) | 960.82 | 607 | −4 | ~10 | 26.10 | 80 |
| XYLENOL ORANGE | 760.6 | 580 | | | 164.90 | 13 |
| HLB30701 | 776.58 | 573 | | >20 | 52.20 | 40 |
| HLB30702 (Trypan Blue) | 960.82 | 608 | | >20 | 5.50 | 382 |
| HLB30703 | 867.69 | 571 | | >20 | 17.90 | 117 |
| HLB30401P | 941.01 | 542 | | >20 | 17.70 | 119 |
| HLB30818 | 1,447 | 607 | +1 | | 4.40 | 477 |

TABLE 3

Quencher dyes were screened against 20 ligand-receptor pairs to determine their effect on cell responses characterized by EC50 and maximal responses (Fmax/Fb). Nitrazine yellow and nitro red were screened out because peptide and lipid agonists showed higher potency comparing with using other dye quenchers, such as trypan blue and a commercial dye kit from Molecular Devices, Corp. (MDC, Cat # R-8034).

| Cell Line | Receptor | Ligand | NY & H30602 | | MDC dye | | TB & H30602 | | NR & H30602 | |
|---|---|---|---|---|---|---|---|---|---|---|
| | | | EC50 | Fmax/Fb | EC50 | Fmax/Fb | EC50 | Fmax/Fb | EC50 | Fmax/Fb |
| ASC0089 | GCGR | glucagon | 5.9 pM | 4.9 | 11 pM | 4 | 183 pM | 4.6 | 3.6 pM | 4.2 |
| ASC0089 | Cyclase | forskolin | 0.16 μM | 5.1 | 0.23 μM | 5.3 | | | | |
| ASC0089 | β-adrenoceptor | isoproterenol | 2.6 nM | 5.4 | 2.5 nM | 4.9 | | | | |
| ASC0093 | DP | PGD2 | 7.8 pM | 4.2 | 18 pM | 4.4 | | | | |
| ASC0097 | A2B | NECA | 120 nM | 4.3 | 72 nM | 4.8 | 66 nM | 4.7 | | |
| ASC0097 | EP2 | PGE1 | 40 nM | 5.3 | | | | | | |
| ASC0106 | GLP1R | GLP | 3.0 pM | 3.7 | 9.3 pM | 4.3 | | | | |
| ASC0069 | PTH1R | PTH | 20 pM | 3 | 50 pM | 3.4 | | | 18.8 pM | 2.7 |
| ASC0145 | VIP2R | VIP | 14 pM | 4.2 | 258 pM | 4.2 | | | 14.9 pM | 3.8 |
| ASC0164 | IP | iloprost | 5.7 pM | 4.6 | 13.5 pM | 4.4 | 22.5 pM | 3.8 | 6.9 pM | 4.8 |
| ASC0172 | EP4 | PGE2 | 26.5 pM | 4.6 | 33.1 pM | 4.4 | 88 pM | 4.6 | 32.3 pM | 4.8 |
| ASC0182 | DRD1 | dopamine | 234 pM | 3.1 | 292 pM | 2.9 | | | 312 pM | 2.7 |
| ASC0192 | MC5R | [Nle4-D-Phe7]α-MSH | 0.95 μM | 3.4 | 2.9 μM | 3.6 | | | 1.3 μM | 3.2 |
| ASC0143 | VIP1R | VIP | | | 2.4 pM | 4.9 | 5.0 pM | 5 | | |
| ASC0154 | A2A | CGS21680 | | | 3.2 nm | 3.8 | 3.4 nM | 3.4 | | |
| ASC0169 | AVPR2 | AVP | | | 8.3 pM | 5.1 | 6.7 pM | 4 | | |
| ASC0179 | MC1R | α-MSH | | | 0.82 μM | 5 | 0.77 μM | 5.1 | | |
| ASC0133 | GIPR | GIP | 0.81 pM | 3.8 | 8.2 pM | 3 | | | | |
| ASC0156 | CALCRL | hCGRPb | 16 pM | 4.6 | 18 pM | 4.4 | | | | |
| ASC0177 | CRHR1 | CRF | 28 pM | 4.3 | 28 pM | 4.2 | | | | |

> = 1 order EC50 shift

~0.5 order EC50 shift

Example 17

CNG Channel Pore Mutations

CNG channels from retina and olfactory tissues are highly homologous at the protein level. However, the CNG channels differ significantly in their specificity, responding primarily to cGMP or cAMP, respectively. Several structure-function studies published on retinal CNG channels have disclosed single-site changes that affect these specificities. Other publications have disclosed alternative positions and changes that effect the identity of ions that transit the activated channel, or the sensitivity of the channel toward cyclic nucleotides. These changes provided guidance for introducing a combination of mutations within the rat olfactory channel CNGA2 (formerly designated rOCNC1) in an attempt to increase cAMP specificity, sensitivity, and robustness for application as a cAMP sensor in high-throughput screening. It was not evident that either the site chosen or the identity of the amino acid change would function in the rat CNGA2 channel in a manner similar to those described. Nor was it evident that if mutations were identified with the desired individual effects, that the multiple mutations would function together to provide the cumulative desired effects.

The mutations E342G, and E342N (see SEQ ID NO: 2 for the base sequence of the rat CNGA2) were generated in rat CNGA2 based on electrophysiological data published on rod cGMP-gated channel (Eismann et al., 1994, A single negative charge within the pore region of a cGMP-gated channel controls rectification, Ca blockage, and ionic selectivity. *PNAS*, 91:1109-1113) and bovine olfactory CNGA2 channel (Gavazzo et al., 2000, A point mutation in the pore region alters gating, Ca blockage, and permeation of olfactory cyclic nucleotide-gated channels. *J. Gen. Physiol.*, 116:311-325) as effecting calcium flow through the channel. Using the CNG of the current invention it was shown for the first time that rat CNGA2 containing mutations at this position provide improved signal-to-noise ratios in high-throughput screening assays when using either voltage potential dyes or calcium detector dyes.

Several amino acid changes were made at other two sites, C460 and E583 (see SEQ ID NO: 2 for the base sequence of the rat CNGA2), of rat CNGA2. Mutations or modifications of amino acids at these two sites have been shown to increase sensitivity and selectivity of the channels toward cAMP (Varnum et al., 1995, Molecular mechanism for ligand discrimination of cyclic nucleotide-gated channel. *Neuron*, 15:619-25; Brown et al., 1998, Movement of gating machinery during the activation of rod cyclic nucleotide-gated channels. *Biophys. J*, 75:825-833; Rich et al., 2001, In vivo assessment of local phosphodiesterase activity using tailored cyclic nucleotide-gated channels as cAMP sensors. *J. Gen. Physiol.*, 118: 63-77).

In summary, mutations in the rat CNGA2 channel at several sites were generated and found to increase signal and sensitivity of the assay. The tested mutations include: E342G, E342N, E342D, E342Q, and E342K; C460R, C460L, C460W, and C460H; E583Q, E583M, E583V, E583A, E583L, E583F, and E583K. The rat CNGA2 channels containing these mutations have been functionally tested following transient expression in HEK293 cells. E342G, E342N mutations were identified as providing a robust response when cells expressing the adenosine A2B receptor are treated with the agonist NECA in the presence of extracellular calcium.

Figures 27A, 27B, 27C, 27D:
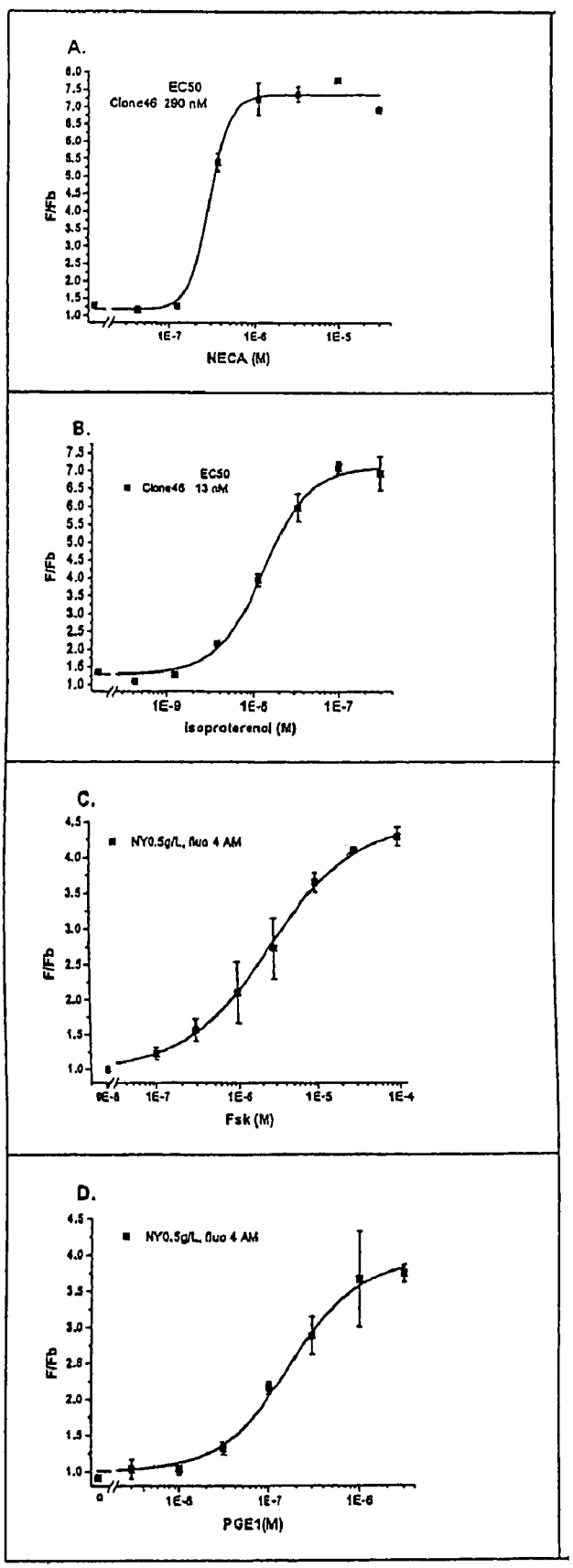
FIG. 27 shows assay results using a stable HEK293 cell line expressing CNGA2 mutant (E342G, C460W, E583M). In assay using voltage dyes with CNG channel containing the pore mutation E342G, EGTA is no more required to be added to remove calcium from extracellular space. Assay using voltage dyes was performed in the presence of extracellular calcium of 0.9-2 mM, compound was dissolved in DPBS (A, B). In assay using calcium dyes with CNG channel containing the pore mutation E342G, compound was dissolved in media containing 30 mM CaCl2 to yield a final CaCl2 concentration around 8 mM (C, D).

A stable cell line has been generated that contains rat CNGA2 with the E342G mutation. In assays using pore mutants, the signal-to-background ratio was found to be significantly improved when using either membrane potential voltage-sensitive dyes or calcium-sensitive dyes (FIG. 27). In the assay using CNG channel without a pore mutation, EGTA has to be included to chelate calcium ions to reveal voltage-change mediated through activation of CNG channels, because extracellular ions block cation currents through the channel pore. We found that addition of EGTA in the extracellular assay solution slightly depolarizes cell membranes causing fluorescence increases over baseline by about 40%. This effect of EGTA might result from activation of store-operated cation current. In assays using a CNG channel, the baseline drift was eliminated so that signal increases by about 40%. Dose-response relations of NECA and isoproterenol were obtained using a CNG triple mutant (E342G, C460W, E583M) cell line and using a membrane potential dye, HLB30602 (FIG. 27, A, B). EGTA exerts other effects including causing morphological changes of cells. Cells became round-up and started to detach from culture substrate in the presence of EGTA. The use of CNG channel pore mutants has solved these problems associated with using EGTA. The pore mutation also contributes to increase in calcium permeability so that the assay is more robust using calcium dye. Dose-response relations of forskolin and PGEI were obtained using a CNG triple mutant (E342G, C460W, E583M) cell line and using a calcium dye, fluo-4 (FIG. 27, A, B).

Rat CNGA2 derivatives containing mutations at sites 342, 460, and 583 were further constructed and tested. One such mutant: E342G, C460R, E583L was found to generate functional homomeric channels with several unique properties, including: (1) better sensitivity; (2) better signal-to-noise performance; (3) more physiological assay conditions that avoid the necessity of using Ca-chelator, EGTA; and (4) facilitating delivery of compounds in HTS operation.

Example 18

Assay of Gi-Coupled GPCRs and Use of Gs-i Chimera

Figures 28A, 28B:
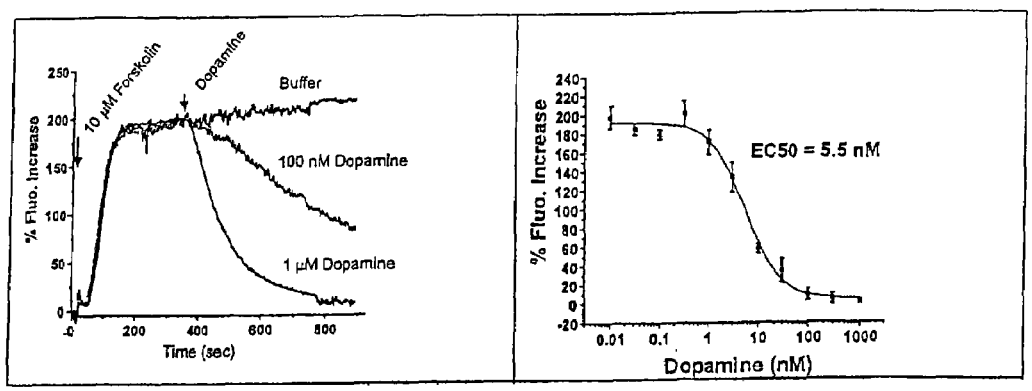
FIG. 28A is a graph showing the kinetic response to dopamine in a CNG-DRD2 cell line measured in 96-well plates with FLEXstation plate reader.
FIG. 28B is a graph showing the results of an Endpoint assay of CNG-DRD2 cells measured in 96-well plates with FLEXstation plate reader.

Gi-coupled receptors comprise approximately 45% of all GPCRs. It is also the most difficult group of receptors for HTS assay development. Because Gi receptors down-regulate cAMP levels, assays detecting their activation are typically based on their inhibition of upregulation of cAMP by forskolin or activation of Gs-coupled receptors. This balance of upregulation/downregulation is both tricky and receptor dependent, and consequently, current cAMP assays often do not provide an adequate detection window for Gi-receptor activation. The traditional functional cAMP assays of Gi-coupled GPCRs are usually carried out by stimulating adenylyl cyclase (AC) with forskolin or by activating a Gs-coupled receptor with its agonist, followed by activating Gi-coupled receptors to decrease the cAMP level. This kind of assay is figuratively dubbed as "upside down assay", as the activation of receptor brings down the fluorescence signal from a highly activated level. Our real-time cAMP assay made it possible to examine the entire process of AC activation, followed by the activation of DRD2 receptor, second by second (FIG. 28 A). Cells were stimulated with forskolin without a PDE inhibitor, followed by the addition of dopamine. The addition of dopamine resulted in an immediate reduction of the forskolin-induced fluorescence signal, nearly returning to the pre-forskolin level within about 7 min (FIG. 28 A). FIG. 28A shows the kinetic response to dopamine in a CNG-DRD2 cell line measured in 96-well plates with FLEX-station plate reader. A maximal response to 1 μM dopamine was reached in about 400 seconds.

In addition to the kinetic analysis, end-point data were obtained by simultaneously incubating the cells with forskolin and dopamine for 15 min, followed by reading the fluorescence signals (FIG. 28 B). FIG. 28B shows the results of an endpoint assay of CNG-DRD2 cells measured in 96-well plates with FLEXstation plate reader. Cells were treated with 10 μM forskolin and different concentrations of dopamine without a PDE inhibitor. Fluorescence readings were obtained before compound addition for baseline and 15 min after compound addition for induction.

As an alternative approach, we redirect Gi-coupled receptors to activate adenylyl cyclase through artificial Gs-i chimera proteins to form a "right-side up assay" as to Gs-coupled receptors (Komatsuzaki et al., 1997, *FEBS Lett.* 406:165-70; Drew et al., 2002, *Biochim Biophys Acta.* 1592:185-92). To accomplish this, we have constructed and introduced a collection of chimeric G-proteins, namely, Gs-i1, Gs-i3, Gs-iz, and Gs-io. This approach, while less physiological, has improved the assay signal and simplified the assay procedures, thereby enable HTS against certain otherwise intractable Gi-targets. The Gs-i approach is an analogous strategy to Gq-i approach that has been widely adopted in HTS (Milligan and Rees, 1999, *TiPS.* 20:118-124). Moreover, the CNG-cAMP technology has several additional advantages over Gq-coupled assays on a FLIPR, including improved signal amplitude and signal stability. Such stable fluorescence signal can be detected with standard fluorescence plate readers, enabling broader adaptation of the technology.

Figures 28C, 28D:
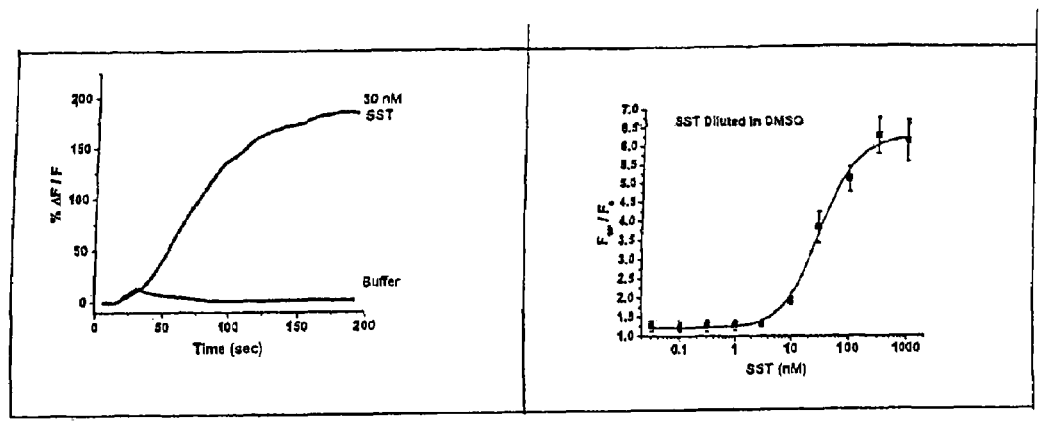
FIG. 28C is a graph showing the kinetic response to somatostatin (SST) in HEK293H-CNG cell line transiently co-transfected with a Gi-coupled SSTR5 receptor and Gs-i3 chimeric G-protein. Recording was made in a 96-well plate with FLEXstation.
FIG. 28D is a graph showing the results of an endpoint assay of responses to somatostatin (SST) in a cell line HEK293H-CNG:SSTR5::Gs-i3 stably expressing CNG, SSTR5 and a chimeric Gs-i3 protein. Recording was made in a 384-well plate with FLEXstation.

The chimeric Gs-i proteins comprise N-terminal Gs with the last C-terminal 5 amino acid residues replaced by those derived from Gi1 (DCGLF; SEQ ID NO: 20), Gi3 (ECGLY; SEQ ID NO: 21), Gio (GCGLY; SEQ ID NO: 22) and Giz (YIGLC; SEQ ID NO: 23) proteins. In experiments designed to assess the potential of this strategy, we constructed Gs-i3 chimeric G-protein. By co-transfecting Gs-i3 and the somatostatin receptor 5 (SSTR5) into the HEK293-CNGA2$^{CE}$ background, we observed SSTR5-dependent increase of fluorescence signal in kinetic study, an indication that the Gi-coupled SSTR5 was redirected to the Gs pathway, resulting in an increase in cellular cAMP (FIG. 28 C). The amplitude of the response for the transiently transfected SSTR5 receptor was similar to that of the Gs-receptors. FIG. 28C shows the kinetic response to somatostatin (SST) in HEK293H-CNG cell line transiently co-transfected with a Gi-coupled SSTR5 receptor and Gs-i3 chimeric G-protein. Recording was made in a 96-well plate with FLEXstation. The cells were labeled with a MP dye. Upon stimulation with somatostatin, the fluorescence intensity was recorded for 3 min with FlexStation.

We also established a SSTR5::Gs-i3 stable cells line in the HEK293H-CNGA2 cells. Assay of this cell line revealed not only that Gs-i3 could redirect Gi-coupled SSTRS through the Gs pathway, but also that the amplitude of the signal is comparable with that of Gs-receptor cell lines (FIG. 28 D). FIG. 28D is a graph showing the results of an endpoint assay of responses to somatostatin (SST) in a cell line HEK293H-

CNG:SSTR5::Gs-i3 stably expressing CNG, SSTR5 and a chimeric Gs-i3 protein. Recording was made in a 384-well plate with FLEXstation. The cells were labeled with a MP dye. The fluorescence intensity was recorded before ($F_0$) and 10 min ($F_{10'}$) after addition of somatostatin at different concentrations. Dose-response curve is created by fitting the data to the Hill equation.

Example 19

Application of the CNG cAMP Assay to Fluorescence Activated Cell Sorter (FACS)

FACS analysis and cell sorting are widely used in both clinical and basic researches. Measurement of the second messenger cAMP can provide a quick functional assay of biological responses of cells to antigens, hormones, and other varieties of chemical and physical stimuli. There are no effective approaches currently available to determine the cAMP level in the living cells with FACS and there are no small molecule indicators for cAMP. Further, the traditional cAMP competitive immunoassay can not be applied to FACS, because it does not provide single-cell sensitivity and requires cell lysis. Therefore a method is described here to combine use of a CNG channel as a cAMP sensor and use of calcium and membrane potential dyes. Protocols using FACS to monitor [$Ca^{2+}$]i and membrane potential of cells are well established and can be easily adopted to monitor CNG channel activity (Lazzar et al., 1986, *J Biol Chem,* 261:9710-9713; Shapiro, 2000, *Methods,* 21:271-279).

To facilitate adaptation of CNG technology to FACS monitoring cAMP in living cells, it is desirable to develop a quick expression protocol of CNG channels in the cells to be assayed. It takes about 2-3 days to express CNG channels using the commercial cDNA liposome transfection kits (e.g. Lipofectamine™ 2000, FuGENE, and etc.). Further, the transfection efficiency using these commercial kits is variable with cell types with these kits. Therefore, these current transfection methods offer very limited use of CNG sensor technology. Using adenovirus to express CNG channel has been explored (Fagan et al., 2001, *FEBS Lett.* 500:85-90). Cells can be assayed at about 24 hr after infection of the adenovirus CNG channels. Methods enabling faster expression of the CNG channels are potentially more useful in FACS analysis of cAMP in living cells, which will not only shorten the assay period but also avoid potential toxigenic and apoptotic effects of CNG expression. A quantitative expression of GFP protein has been established by RNA transfection using an electroporation protocol (Teruel et al., 1999, *J Neurosci Methods,* 93:37-48). This RNA transfection method will allow a quick expression of CNG and cAMP assay in cell samples within 8 hrs. Other gene delivery methods can also be developed and applied to express CNG quickly in cells to be assayed (see Kaneda et al., 2002, *Mol Ther.,* 6:219-226).

Example 20

Simultaneous Screening of Gs, Gi, and Gq GPCR with CNG Channel Technology for Receptor De-orphanization and Compound Profiling Of the greater than 750 human GPCR genes, at least 367 are predicted to bind endogenous ligands. Within this group, ligands have been identified for 224 GPCRs leaving 143 orphan receptors for which neither ligands nor functions are known (Vassilatis et al. 2003 Vassilatis DK, The G protein-coupled receptor repertoires of human and mouse. *Proc Natl Acad Sci USA;* 2003; 100:4903-4908). Because about 40% of all the marketed drugs are directed against only 30 GPCRs, it is reasonable to infer that a substantial number of potentially druggable GPCR targets are still present within the pool of functionally uncharacterized GPCRs. Thus, assays that would allow receptor de-orphanization [identification of a ligand (agonist or antagonist), coupling G-protein, and a function for an orphan receptor] are being actively sought in drug discovery. The CNG-technology described herein represents a novel, advantageous tool that enables orphan GPCR receptors to be screened in a universal calcium read-out format.

As demonstrated below, HEK 293-CNG cells expressing orphan GPCR DNAs (either endogenous receptors, or transiently or stably transfected exogenous receptors) can be directly tested for functional coupling of the receptor with Gq, Gs, or Gi. Based on the response, in particular the kinetics of the response, it is possible to both identify activated orphan receptors, and determine the G-protein coupling. Further, this approach does not require the need to introduce promiscuous G proteins (e.g. $G\alpha16$) that provide "artificial" coupling to Gs/i GPCRs that would not otherwise generate a calcium signal. In a preferred embodiment, this approach can be used to identify and deorphanize and determine the coupling of endogeneous receptors in a broad range of cell types into which a functional CNG can be introduced.

A protocol using HEK 293-CNG (SEQ ID No: 8) cells stably expressing the exogenous Gi-coupled D2 dopamine receptor (LocusID 1813) was designed to test this model. Cells were plated in 96 well plates (15,000 cell/well), grown overnight, and labeled with the fluorescent calcium indicator Fura-2 (5 μM). Single cell kinetic calcium imaging was performed using PathwayHT (Atto Bioscience), an automated imaging platform with liquid dispensing capabilities. Activation of Gq-coupled GPCRs results in release of intracellular calcium stores. In contrast, activation of Gs coupled receptors stimulate adenylyl cyclase, resulting in increasing levels of cyclic AMP (cAMP), while Gi coupled receptors inhibit adenylyl cyclases, reducing levels of cAMP.

Figure 29:
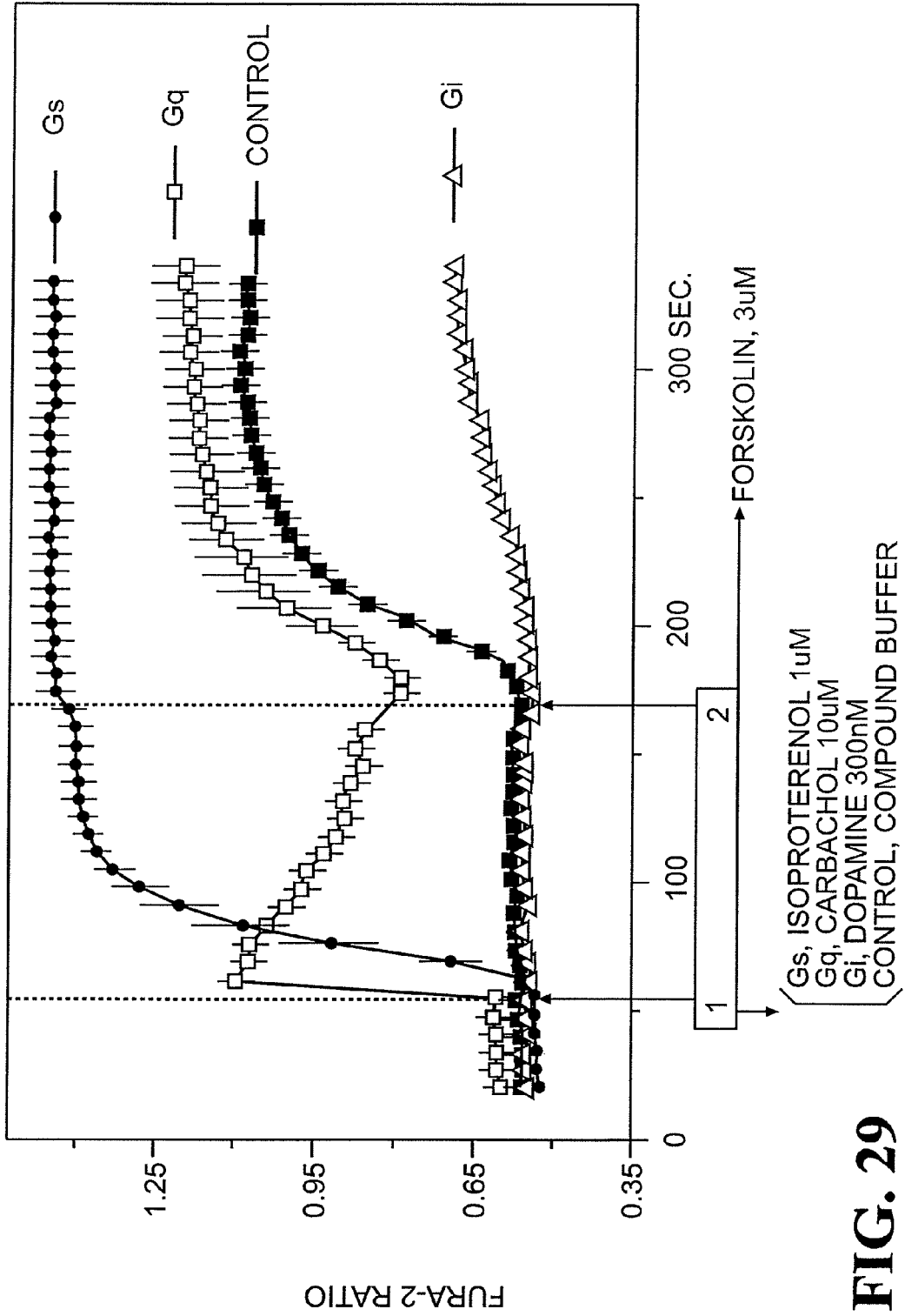
FIG. 29 is a graph comparing calcium responses following Gq, Gs and Gi-GPCR activation.

As shown in FIG. 29, the addition of a first compound (1), in this case carbachol (100 M), that activates the endogenous Gq-coupled muscarinic receptor, induces a rapid and transient calcium rise (characteristic of Gq-mediated internal calcium release); activation of endogenous Gs-coupled GPCR, the β-adrenergic receptor (in this case by isoproterenol, 1 μM) triggers a slower but sustained calcium response (due to calcium influx through the cAMP-activated CNG channel), while activation of Gi-coupled D2 dopamine receptor (in this case, by 300 nM dopamine) or addition of compound buffer alone does not affect calcium levels. A subsequent addition (2) of a known cAMP agonist [in this case 3 μM forskolin, which directly activates adenylyl cyclase (AC)] is observed to increase cAMP levels in the control (compound buffer only), but not if the Gi-coupled D2 receptor is also activated (as would be expected if the activated Gi inhibits adenylyl cyclase). The extent of the signal reduction is expected to be proportional to the potency of the first test compound.

While cAMP levels were induced by directly stimulating AC in this example, it will be apparent to those skilled in the art that activation of any Gs-coupled receptor could also be used in this assay to activate AC. It can be further seen that the first transient calcium increase observed for the Gq-GPCRs is followed by a sustained calcium response (due to increasing levels of cAMP as a result of activating ACs, and subsequent activation of the CNG). For Gs-GPCRs, the first calcium response is either not affected (e.g. first ligand exhibits maximal potency/efficacy toward cAMP activation, as in the case shown) or is further enhanced. We have further shown that calcium imaging is unaffected (signal to noise/sensitivity) by the presence of a quenchers. Consequently, Gs/Gi/Gq screening with CNG-293 cells is feasible as a simple, two-step homogeneous format (dye loading and compound additions, no wash required) substantially increasing ease of use and speed. Hence, the current invention allows a simple two-step deorphanization and determination of receptor coupling.

In another preferred embodiment, the current invention is applicable to ligand profiling screens. In this application, compounds are tested for their effect (agonist/antagonist/ allosteric modulators) on collections of GPCRs, typically receptor families. As described above, agonists, inhibitors of agonists, or modulators of agonists or antagonists can be surveyed by contacting cells expressing receptors of interest with compounds and assessing the response. Because the kinetics of each response is indicative not only of agonist/ antagonist or modulator, but also the coupling, combinatorial assays that in addition generate deorphanization and receptor coupling results can be developed.

In yet another embodiment, imaging-based deorphanization or ligand profiling screens using the current invention can be done in 96 well plates, 384 well plates, 1536 well plates or in implemented on a cell microarray platform (where multiple GPCR genes are introduced in spatially discrete locations, and cells are grown over the DNA to provide an array of cell populations, wherein each population within a spot can contain a different GPCR. Said arrays can be generated within the same well of a microtiter plate). This approach provides unprecedented speed and multiplexing for receptor assays using the current invention, including de-orphanization and ligand profiling screening.

Although the present invention has been described in detail with reference to examples above, it is understood that various modifications can be made without departing from the spirit of the invention. Accordingly, the invention is limited only by the following claims. All cited patents, patent applications and publications referred to in this application are herein incorporated by reference in their entirety.

What is claimed is:

1. An isolated polynucleotide comprising a sequence encoding a mutant cyclic nucleotide-gated (CNG) channel comprising:
   (a) at least one mutation that decreases divalent cation-mediated blockage of cation flux as compared to a channel that does not comprise the mutation; and
   (b) at least one mutation that makes the channel more sensitive to cAMP than a channel that does not comprise the mutation,
   wherein said CNG channel is CNGA2, wherein said at least one mutation that decreases divalent cation-mediated blockage of cation flux comprises a mutation at a position corresponding to E342 of SEQ ID NO:02, and wherein said mutation that makes the channel more sensitive to cAMP comprises a mutation at a position corresponding to C460 and/or E538 of SEQ ID NO:02.

2. The isolated polynucleotide of claim 1, wherein said CNGA2 channel is rat CNGA2.

3. The isolated polynucleotide of claim 2, wherein said at least one mutation that decreases divalent cation-mediated blockage of cations is selected from the group consisting of E342G and E342N.

4. The isolated polynucleotide of claim 2, wherein said at least one mutation that makes the channel more sensitive to cAMP than a channel that does not comprise the mutation is selected from the group consisting of C460R, C460H and E583L.

5. A host cell comprising a first nucleic acid comprising the isolated polynucleotide of claim 1.

6. The host cell of claim 5, wherein said cell is selected from the group consisting of BHK cells, mouse L cells, Jurkat cells, 153DG44 cells, HEK cells, CHO cells, PC12 cells, human T-lymphocyte cells, Cos-7 cells and primary cells.

7. The host cell of claim 5, wherein said isolated polynucleotide is stably integrated into in a host chromosome.

8. The host cell of claim 5, wherein the cell expresses at least a first endogeneous GPCR.

9. The host cell of claim 8, further comprising a second nucleic acid comprising a promoter operably linked to a second polynucleotide wherein the second polynucleotide comprises a sequence encoding an heterologous G protein-coupled receptor (GPCR).

10. A host cell according to claim 8, further comprising a second nucleic acid comprising a promoter operably linked to a second polynucleotide comprising a sequence encoding the endogenous GPCR, wherein the endogenous GPCR is expressed at a higher level in the cell when the cell contains the second nucleic acid.

11. A host cell according to claim 9, wherein at least one of the first and the second nucleic acids is not part of the genome of the cell.

12. A host cell according to claim 8, wherein the host cell is a mammalian cell.

13. A host cell according to claim 12, wherein the cell is selected from the group consisting of BHK cells, mouse L cells, Jurkat cells, 153DG44 cells, HEK cells, CHO cells, PC12 cells, human T-lymphocyte cells, Cos-7 cells and primary cells.

14. A host cell according to claim 8, wherein the mutations that make the channel more sensitive to cAMP comprises mutations at two positions corresponding to C460 and E538 of SEQ ID NO:02.

15. A host cell according to claim 5, wherein said CNGA2 channel is rat CNGA2.

16. A host cell according to claim 15, wherein said at least one mutation that decreases divalent cation-mediated blockage of cations is selected from the group consisting of E342G and E342N.

17. A host cell according to claim 16, wherein said at least one mutation that makes the channel more sensitive to cAMP than a channel that does not comprise the mutation is selected from the group consisting of C460R, C460H and E583L.

18. A host cell according to claim 5, wherein said host cell further expresses at least one additional CNG subunit selected from the group consisting of CNGA4 and CNG4.3.

* * * * *

UNITED STATES PATENT AND TRADEMARK OFFICE
CERTIFICATE OF CORRECTION

| | | |
|---|---|---|
| PATENT NO. | : 7,604,959 B2 | Page 1 of 4 |
| APPLICATION NO. | : 11/783884 | |
| DATED | : October 20, 2009 | |
| INVENTOR(S) | : Yong Yao | |

It is certified that error appears in the above-identified patent and that said Letters Patent is hereby corrected as shown below:

Title Page; In Section 63, line 23, before "Continuation-in-Part" please insert the following text:

--Divisional of application no. 10/978,282, filed on November 1, 2004, now Patent No. 7,238,213, which is a--.

In the Figures Section, please delete Sheets 25 and 26 of the 38 sheets of Figures, (pages 26 and 27 of the issued patent) which reflect "Fig. 17B (Cont'd)", as these sheets were to be replaced with Figures 17C, and 17D (pages 28 and 29 of the issued patent).

Signed and Sealed this

Eighth Day of June, 2010

David J. Kappos
*Director of the United States Patent and Trademark Office*

Adrenergic compound-plate from BIOMOL

| | 1 | 2 | 3 | 4 |
|---|---|---|---|---|
| A | 2-[[beta-(4-HYDROXYPHENYL)ETHYL]AMINO]ETHYL]-1-TETRALONE<br>Alpha 1 adrenergic antagonist | GUANABENZ ACETATE<br>Alpha 2 adrenergic agonist | NICERGOLINE<br>Alpha adrenergic antagonist | CGP 12177 HCl<br>Beta 3 adrenergic agonist; beta 1 & 2 adrenergic antagonist |
| B | 5-METHYLURAPIDIL<br>Alpha 1A adrenergic antagonist | CGP 20712A METHANESULFONATE<br>Beta 1 adrenergic antagonist | CHLOROETHYLCLONIDINE 2HCl<br>Alpha 1B adrenergic alkylating agent | (±)-ISOPROTERENOL HCl<br>Beta adrenergic agonist |
| C | IFENPRODIL<br>Alpha 1 adrenergic antagonist | 2-[[4-(2-METHOXYPHENYL)PIPERAZIN-1-YL]METHYL]-6-METHYL-2,3-DIHYDROIMIDAZO[1,2-C]QUINAZOLIN-5(6H)-ONE<br>Alpha 1 adrenergic antagonist | NAFTOPIDIL 2HCl<br>Alpha 1 adrenergic antagonist | 2-[(4-PHENYLPIPERAZIN-1-YL)METHYL]-2,3-DIHYDROIMIDAZO[1,2-C]QUINAZOLIN-5(6H)-ONE<br>Alpha 1 adrenergic antagonist |
| D | RILMENIDINE HEMIFUMARATE<br>Alpha 2 adrenergic agonist | UK 14,304<br>Alpha 2 adrenergic agonist | ARC 239 2HCl<br>Alpha 2B adrenergic antagonist | BRL 44408 MALEATE<br>Alpha 2A adrenergic antagonist |
| E | (±)-ATENOLOL<br>Beta adrenergic antagonist | R-(+)-ATENOLOL<br>Inactive isomer | S-(-)-ATENOLOL<br>Beta adrenergic antagonist | BETAXOLOL HCl<br>Beta 1 adrenergic antagonist |
| F | ICI 215,001 HCl<br>Active metabolite of ZD 7114 | ZD 7114 HCl<br>Beta 3 adrenergic agonist | PINDOLOL<br>Beta 3 adrenergic partial agonist | (S)-(-)-PINDOLOL<br>Beta 3 adrenergic partial agonist |
| G | PROPRANOLOL GLYCOL<br>Metabolite of propranolol | SOTALOL HCl<br>Beta adrenergic antagonist | MAPROTILINE HCl<br>Norepinephrine uptake inhibitor | NISOXETINE HCl<br>Norepinephrine uptake inhibitor |
| H | TIZANIDINE HCl<br>Alpha 2 adrenergic agonist | AH 11110A<br>Alpha 1B adrenoceptor ligand | EFAROXAN<br>Alpha 2 adrenergic antagonist | IDAZOXAN<br>Alpha 2 adrenergic antagonist |

NOTES:
1. Iso: ISOPROTERENOL
2. All compound concentration is 5 uM

*FIG. 17B*   To FIG. 17C →

Adrenergic compund-plate from BIOMOL

| 5 | 6 | 7 | 8 |
|---|---|---|---|
| R-(+)-PROPRANOLOL<br>*Propranolol enantiomer (less active)* | RAUWOLSCINE HCl<br>*Alpha 2 adrenergic antagonist* | AMOXAPINE<br>*Norepinephrine uptake inhibitor* | Blank |
| PHENTOLAMINE MESYLATE<br>*Alpha adrenergic antagonist* | A 61603 HBr<br>*Alpha 1A adrenergic agonist* | CIRAZOLINE HCl<br>*Alpha 1 adrenergic agonist* | M-6434<br>*Alpha 1 adrenergic agonist* |
| PRAZOSIN HCl<br>*Alpha 1 adrenergic antagonist* | RS 17053 HCl<br>*Alpha 1A adrenergic antagonist* | WB 4101 HCl<br>*Alpha 1A adrenergic antagonist* | 3-[2-[4-(2-CHLOROPHENYL)PIPERAZIN-1-YL]ETHYL]PYRIMIDO[5,4-B]INDOLE-2,4-DIONE<br>*Alpha 1 adrenergic ligand* |
| IMILOXAN HCl<br>*Alpha 2 adrenergic antagonist* | RS 79948 HCl<br>*Alpha 2 adrenergic antagonist* | SPIROXATRINE<br>*Alpha 2 adrenergic ligand* | YOHIMBINE HCl<br>*Alpha 2 adrenergic antagonist* |
| PRACTOLOL<br>*Beta adrenergic antagonist; weak partial agonist* | (S)-TIMOLOL MALEATE<br>*Beta 1 adrenergic antagonist* | XAMOTEROL HEMIFUMARATE<br>*Beta 1 adrenergic partial agonist* | CLENBUTEROL<br>*Beta 2 adrenergic agonist* |
| CIMATEROL<br>*Beta adrenergic agonist* | N-DESISOPROPYL-PROPRANOLOL HCl<br>*Metabolite of propranolol* | DOBUTAMINE HCl<br>*Beta 1 adrenergic agonist* | ICI 89406<br>*Beta adrenergic antagonist* |
| BOPINDOLOL MALONATE<br>*Beta 1 adrenergic antagonist* | (-)-CYANOPINDOLOL HEMIFUMARATE<br>*Beta adrenergic antagonist* | GUANFACINE HCl<br>*Alpha 2 adrenergic agonist* | ICI-118,551<br>*Beta 2 adrenergic antagonist* |
| SPIPERONE<br>*Alpha 1 beta adrenergic antagonist* | L-(-)-EPINEPHRINE-(+)-BITARTRATE<br>*Endogenous alpha, beta adrenergic agonist* | XYLAZINE HCl<br>*Alpha 2 adrenergic agonist* | L-(-)-NOREPINEPHRINE-(+)-BITARTRATE<br>*Endogenous alpha, beta adrenergic agonist* |

← From FIG. 17B    To FIG. 17D →

*FIG. 17C*

| | 9 | 10 | 11 | 12 |
|---|---|---|---|---|
| | | Adrenergic compund-plate from BIOMOL | | |
| | Blank | Blank | Blank | Iso |
| | OXYMETAZOLINE HCl<br>Alpha 2A adrenergic partial agonist; alpha 1A agonist | BMY 7378 2HCl<br>Alpha 1D adrenergic antagonist | CORYNANTHINE HCl<br>Alpha 1 adrenergic antagonist | Iso |
| | 3-[2-[4-(2-METHOXYPHENYL) PIPERAZIN-1-YL]ETHYL]-1,5-DIMETHYLPYRIMIDO [5,4-B]INDOLE-2,4-DIONE<br>Alpha 1 adrenergic ligand | 3-[2-[4-(2-METHOXYPHENYL) PIPERAZIN-1-YL]ETHYL] PYRIMIDO[5,4-B]INDOLE-2,4-DIONE<br>Alpha 1 adrenergic ligand | CLONIDINE HCl<br>Alpha 2 adrenergic agonist | Iso |
| | AGMATINE SULFATE<br>Endogenous Alpha 2 receptor agonist | DIHYDROERGOCRISTINE MESYLATE<br>Alpha adrenergic partial agonist | DIHYDROERGOTAMINE MESYLATE<br>Alpha adrenergic partial agonist | Iso |
| | PROCATEROL HCl<br>Beta 2 adrenergic agonist | SALBUTAMOL SULFATE<br>Beta 2 adrenergic agonist | BRL 37344 SODIUM SALT<br>Beta 3 adrenergic agonist | Iso |
| | 1- NAPHTHOXYACETIC<br>Metabolite of propranolol | 1-NAPHTHOXYLACTIC<br>Metabolite of propranolol | PRONETHALOL HCl<br>Beta adrenergic antagonist | Iso |
| | PHENOXYBENZAMINE HCl<br>Alpha adrenergic antagonist | PROPRANOLOL HCl<br>Beta adrenergic antagonist | S(-)-PROPRANOLOL HCl<br>Beta adrenergic antagonist | Iso |
| | NYLIDRIN HCl<br>Beta adrenergic agonist | ALPRENOLOL HCl<br>Beta adrenergic antagonist | IMIPRAMINE HCl<br>Norepinephrine uptake inhibitor | Iso |

← From FIG. 17C

*FIG. 17D*